United States Patent
McCourt

(10) Patent No.: US 11,737,976 B2
(45) Date of Patent: *Aug. 29, 2023

(54) DRUG DELIVERY MEANS

(71) Applicant: TheraSyn Sensors, Inc., Eggertsville, NY (US)

(72) Inventor: Mary P. McCourt, Amherst, NY (US)

(73) Assignee: THERASYN SENSORS, INC., Eggertsville, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/119,931

(22) Filed: Aug. 31, 2018

(65) Prior Publication Data

US 2019/0060236 A1     Feb. 28, 2019

Related U.S. Application Data

(63) Continuation of application No. 14/741,915, filed on Jun. 17, 2015, now Pat. No. 10,092,516, which is a (Continued)

(51) Int. Cl.
*A61K 9/127*      (2006.01)
*A61K 47/10*      (2017.01)
(Continued)

(52) U.S. Cl.
CPC ............ *A61K 9/1272* (2013.01); *A61K 9/127* (2013.01); *A61K 9/1277* (2013.01);
(Continued)

(58) Field of Classification Search
CPC .... A61K 9/127; A61K 9/1272; A61K 9/1277; A61K 47/10; A61K 47/28;
(Continued)

(56) References Cited

U.S. PATENT DOCUMENTS 4,544,545 A    10/1985    Ryan et al.
5,013,556 A     5/1991    Woodle et al.
(Continued)

FOREIGN PATENT DOCUMENTS

WO        9203123      3/1992
WO     2004098564     11/2004
(Continued)

OTHER PUBLICATIONS

Funakoshi, K., et al. in J. Am. Chem. Soc vol. 129, pp. 12608-12609, 2007.*
(Continued)

*Primary Examiner* — Gollamudi S Kishore
(74) *Attorney, Agent, or Firm* — Henry D. Coleman; R. Neil Sudol

(57) ABSTRACT

The invention broadly comprises a chemical composition including a plurality of cholesteryl esters arranged to form a vesicle. In several embodiments, all of the plurality of cholesteryl esters have a same molecular length, which in some embodiments provides a vesicle having a generally smooth outer surface, while in other embodiments, a portion of the plurality of cholesteryl esters have different molecular lengths, which in some embodiments provides a vesicle having a generally irregular outer surface. In yet further embodiments, a shape of the vesicle is selected from the group consisting of spherical, oval, disc-like, tubular and polyhedral shapes, and in yet other embodiments, a wall of the vesicle is selected from the group consisting of a monolayer and a bilayer. In still further embodiments, the chemical composition further includes a polyethylene glycol coat of mixed polymer size. In some embodiments, the plurality of cholesteryl esters include at least two different cholesteryl esters, and in some of these embodiments, the at least two different cholesteryl esters are selected from the
(Continued)

group consisting of cholesteryl myristate, cholesteryl laurate, cholesteryl dodeconate, cholesteryl palmitate, cholesteryl arachidonate, cholesteryl behenate, cholesteryl linoleate, cholesteryl linolenate, cholesteryl oleate and cholesteryl stearate.

11 Claims, 59 Drawing Sheets

Related U.S. Application Data continuation of application No. 11/725,831, filed on Mar. 20, 2007, now Pat. No. 9,119,782.

(60) Provisional application No. 60/784,118, filed on Mar. 20, 2006.

(51) Int. Cl.
| | | |
|---|---|---|
| *A61K 47/28* | (2006.01) | |
| *A61K 38/17* | (2006.01) | |
| *A61K 38/45* | (2006.01) | |
| *A61K 38/48* | (2006.01) | |

(52) U.S. Cl.
CPC ...... *A61K 38/1709* (2013.01); *A61K 38/1761* (2013.01); *A61K 38/45* (2013.01); *A61K 38/482* (2013.01); *A61K 47/10* (2013.01); *A61K 47/28* (2013.01); *C12Y 207/11001* (2013.01); *C12Y 304/21078* (2013.01); *C12Y 304/21079* (2013.01)

(58) Field of Classification Search
CPC ................ A61K 38/1761; A61K 38/45; A61K 38/1709; A61K 38/482; C12Y 304/21078; C12Y 207/11001; C12Y 304/21079; G06F 21/604; G06F 16/9566; G06F 21/62; G06F 21/6218; G06F 21/6245; G06F 40/295; H04L 51/04; H04L 51/08; H04L 51/32; H04L 63/0861; H04L 63/102; H04L 63/104; H04L 63/105; H04L 63/1408; H04L 63/1416; H04L 63/1425; H04L 65/403; H04L 67/06; H04L 67/1078; H04L 67/1095; H04L 67/1097; H04L 67/306; H04L 63/101
See application file for complete search history.

(56) References Cited

U.S. PATENT DOCUMENTS

| | | | |
|---|---|---|---|
| 5,049,389 | A | 9/1991 | Radhakrishnan |
| 5,094,854 | A | 3/1992 | Ogawa et al. |
| 5,288,499 | A | 2/1994 | Janoff et al. |
| 9,119,782 | B2 | 9/2015 | McCourt |
| 11,052,052 | B2 | 7/2021 | Schentag et al. |
| 2004/0052838 | A1 | 3/2004 | Naeff et al. |
| 2004/0197393 | A1 | 10/2004 | Smyth-Templeton et al. |
| 2006/0216255 | A1* | 9/2006 | Lee .......................... A61K 8/97 424/70.1 |
| 2007/0014840 | A1 | 1/2007 | Lee et al. |
| 2007/0225264 | A1 | 9/2007 | McCourt |
| 2008/0241257 | A1 | 10/2008 | Popescu et al. |
| 2016/0030361 | A1 | 2/2016 | McCourt |
| 2019/0175515 | A1 | 6/2019 | Schentag et al. |
| 2020/0069598 | A1 | 3/2020 | Schentag et al. |
| 2022/0040116 | A1 | 2/2022 | Schentag et al. |

FOREIGN PATENT DOCUMENTS

| | | |
|---|---|---|
| WO | 2014152795 | 9/2014 |
| WO | 2018039303 | 3/2018 |

OTHER PUBLICATIONS

Funakkoshi, K.; et al.; JACS 2007, vol. 129. pp. 12608-12609.
Anonymous: "Undergraduate Research Symposium", WNY ACS Undergraduate Research Symposium The, Jan. 1, 2010 (Jan. 1, 2010), pp. 1-40, XP55288063, Retrieved from the internet: URL:http://wny.sites.acs.org/Symposium/Program6Mar1 0.pdf[retrieved on Jul. 13, 2016].
Bjorkhlem I, et al. Oxysterols: Friends, Foes, or Just Fellow Passengers? Arteriosclerosis, Thrombosis, and Vascular Biology, 2002;22:734-742.
Bleavins MR, et al. Cynomolgus monkeys (Macaca fascicularis in preclinical immune function safety testing: development of a delayed-type hypersensitivity procedure. Toxicology, 1995;95:103-112.
Bussiere JL, et al. 60-Day Repeated Dose Inhalation Toxicity Study of an Anti-IgE Antibody in Cynomolgus Monkeys. SOT Annual Meeting, 1997;271.
Christiansen LI. Preparation, Analysis, and Cholesterol Lowering Effect of a Novel Microcrystalline . . . Suspension in Oil and Phase Behavior of Beta-sitosterol with Cholesterol. Academic Dissertation at the University of Helsinki, Finlad, 2002.
Congestive Heart Failure. American Heart Association, 2006. htto://www.americanheart.org/presenter.jhtml?identifier=4585.
Dorset DL, et al. Co-solubility in binary phospholipid crystals. Biochimica et Biophysica Acta, 1987;903:319-332.
Dorset DL. Binary phase behavior of angiotoxic oxidized cholesterols with cholesterol. Biochimica et Biophysica Acta, 1992;1127:293-297.
Dorset DL. Binary phase behavior of cholestryl oleate with cholesteryl linoleate. Biochimica et Biophysica Acta, 1990;1046:57-63.
Dorset DL. Cholesteryl esters of saturated fatty acids: cosolubility and fractionation of binary mixtures. Journal of Lipid Research, 1987;28:993-1005.
Dorset DL. Co-solubility of saturated cholstryl esters: a comparison of calculated and experimental binary phase diagrams. Biochimica et Biophysica Acta, 1988;963:88-98.
Dorset DL; Eutectic interactions in binary systems containing cholesterol, cholesteryl esters and triacylgycerols. Biochimica et Biophysica Acta, 1990;1047:112-120.
Funakoshi K, et al. Formation of Giant Lipid Vesiclelike Compartments from a Planar Lipid Membrane by a Pulsed Jet Flow.Jam Chem Soc, 2007;129:12608-12609.
Garcia-Cruset S, et al. Oxysterols in cap and core of human advanced atherosclerotic lesions. Free Radical Research, 1999;30:341-351.
Giguere S. et al. "Role of the 85-Kilobase Plasmid and Plasmid-Encoded Virulence-Associated Protein A in Intracellular Survival and Virulence of Rhodococcus equi." Infection and Immunity, 1999;67(7):3548-3557.
Guo W, et al. Phase Behavior and Crystalline Structures of Cholesteryl Ester Mixtures: A C-13 MASNMR Stufy. Biophysical Journal, 1995;68:2376-2386.
Heart Attack, Stroke & Cariac Arrest Warning Signs. American Heart Association, 2006. http://www.americanheart.org/presenter.jhtml?identifier=3053.
Huan Xu et al: "Preparation and Characterization of pH-Sensitive Vesicles Made of Cholesteryl Hemisuccinate", Dr.ug-Development and Industrial Pharmacy, vol. 34, No. 2, Jan. 1, 2008 (Jan. 1, 2008), pp. 134-141.
Hulten LM, et al. Oxysterols persent in atherosclerotic tissue decrease the expression of lipoprotein lipase messenger RNA in human monocyte-derived macrophages. The Journal of Clinical Investigation, 1996;97:461-468.
Leoni V. On the possible use of oxysterols for the diagnosis and evaluation of patients with neurological and neurogedenerative diseases. Karolinska Institutel Thesis, Stockholm, Sweden, 2005.
Linseisen J, et al. Plasma 7beta-hydroxycholesterol as a possible predictor of lung cancer risk. Cancer Epidemoil Prev, 2002;11:1630-1637.
Lizard G, et al. Characterization and Comparison of the Mode of Cell Death . . . by 7beta-Hydroxycholesterol and 7-Ketocholesterol in the Cells of the Vascular Wall, Arteriosclerosis, Thrombosis and Vascular Biology, 1999;19:1190-1200.

(56) References Cited

OTHER PUBLICATIONS

Mahadevan V, et al. Preparation of cholesterol esters of long-chian fatty acids and characterization of cholesteryl arachidonate. Journal of Lipid Research, 1962;3:106-110.

Marcu L, et al. Arterial flourescent components involved in the atherosclerotic plaque instability: differentiation by time-resolved flourescence spectroscopy, 2001.

McCour MP, et al. X-ray crystal structure of cytotoxic oxidized cholesterols: 7-ketocholesterol and 25-hydroxycholesterol. Journal of Lipid Research, 1997;38:1014-1021.

Micheletta F, et al. Vitamin E Supplementation in Patients with Carotid Atherosclerosis. Arteriosclerosis, Thrombosis, and Vascular Biology, 2004;24;136.

Nelson DL, et al. Lehninger Principles of Biochemistry fourth edition. New York, WH Freeman and Company, 2005.

Prasad YV, et al. Evaluation of oral formulations of gentamicin containing labrasol in beagle dogs. International Journal of Pharmaceutics, 2003;268:13-21.

Raff LM. Principles of Physical Chemistry. Upper Sakkle River NJ. Prentice Hall, 2001.

Ringseis R, et al. Insufficient dietary vitamin e increases the concentration of 7beta-hydroxycholesterol in tissues of rats feed salmon oil. The Journal of Nutrition, 2002;132:2732-2735.

Rodriguez IR, et al. Cytotoxicity of Oxidized Low-Density Lipoprotein in Cultured RPE Cells Is Dependent on the Formation of 7-Ketocholesterol. Investigative Ophthalmology and Visual Science, 2004;45:2830-2837.

Ryffel. B. Impact of Knockout Mice in Toxicology. Critical Reviews in Toxicology, 1997;27(2):135-154.

Shands Health Care. Transclent ischemic attack (TIA). 2006 http://www.shands.org/health/information/article/000730.htm.

Sigma-Aldrich Corporation. Material Safety Data Sheet. 2006 http://www.sigma.com.

Sweeney TD, et al. Pumonry Delivery of Anti-IgE Rationale for Topical Delivery to the Airway. 2001.

Tontonoz PA, et al. Regulation of macrophage gene expression by peroxisome-proliferator-activated receptor [gamma]: implications for cardiovascular disease. Current Opinion in Lipidology, 1999;10:485-490.

Wikipedia. Apoptosis. 2006, http://en.wikipedia.org/wiki/Apoptosis.

Wohlfeil ER, et al, 25-Hydroxycholesterol Increases Elcosanoids and Alters Morphology in Cultured Pulmonary Artery Smooth Muscle and Endothelial Cells. Arteriosclerosis, Thrombosis, and Vascular Biology, 1999;19:2901-2908.

Yoshida K, et al. Effect of Tumor Size on Monoclonal Antibody Uptake in a Metastatic Model. Journal of Surgical Oncology, 1992;49:249-252.

Sahin, N. O.; Niosomes as Nanocarrier Systems. IN: Nanomaterials and Nanosystems for Biomedical Applications. Edited by M. Mozafari Netherlands: Springer press, 2007, Chapter 4, pp. 67-81.

U.S. Appl. No. 17/337,283, filed Jun. 2, 2021. "Cholestosome Vesicles For Incorporation of Molecules Into Chylomicrons". Applicant: Therasyn Sensors, Inc.

U.S. Appl. No. 16/327,561, filed Feb. 22, 2019 "Cholesteryl Ester Vesicles Loading Peptides, Proteins and Nucleic Acids Into Chylomicrons and Body Cells". Applicant: Therasyn Sensors, Inc.

* cited by examiner

Cholesterol = Yellow; 25-OH = Blue

Cholesterol = Yellow; 7-Keto = Magenta

Cholesterol = Yellow; Cholestane Triol = Orange

Cholesterol = Yellow; 20A = Blue-Green

Cholesterol = Yellow; 7B = White

25-OH = Blue; 7-Keto = Magenta

25-OH = Blue; Cholestane Triol = Orange

25-OH = Blue; 20A = Blue-Green

25-OHh = Blue; 7B = White

Cholestane Triol = Orange; 7-Keto = Magenta

Cholestane Triol = Orange; 20A = Blue-green

Cholestane Triol = Orange; 7B = White

7-Keto = Magenta; 20A = Blue-Green

7-Keto = Magenta; 7B = White

20A = Blue-Green; 7B = White

CO = Blue; CL = Green

CO = Blue; CLn = Orange

CL = Green; CLn = Orange

CD = Purple; CM = Red

CD = Purple; CP = White

CD = Purple; CS = Cyan

CD = Purple; CB = Yellow

CM = Red; CP = White

CM = Red; CS = Cyan

CM = Red, CB = Yellow

CP = White; CS = Cyan

CP = White; CB = Yellow

CS = Cyan; CB = Yellow

DRUG DELIVERY MEANS

CROSS-REFERENCE TO RELATED APPLICATIONS

This patent application is a continuation application of U.S. application Ser. No. 14/741,915 filed Jun. 17, 2015, which issued as U.S. Pat. No. 10,092,516 on Oct. 9, 2018 which is a continuation application of U.S. application Ser. No. 11/725,831 filed Mar. 20, 2007, which issued yes U.S. Pat. No. 9,119,782 on Sep. 1, 2015, which claims the benefit under 35 U.S.C. § 119(e) of U.S. Provisional Application No. 60/784,118, filed Mar. 20, 2006, all three of which applications are incorporated in their entirety herein by reference.

FIELD OF THE INVENTION

The present invention relates to drug delivery and, more particularly, to a targeted drug delivery system and improved therapeutics.

BACKGROUND OF THE INVENTION

Lipids

The term lipid refers to a diverse range of molecules and to some extent it is a catch-all for relatively water-insoluble or nonpolar compounds of biological origin, including waxes, fatty acids, fatty-acid derived phospholipids, sphingolipids, glycolipids, and terpenoids such as retinoids and steroids. Some lipids are linear aliphatic molecules, while others have ring structures. Some are aromatic, white others are not. Some are flexible, while others are rigid.

Phospholipids are a special group of lipids containing phosphate. Phospholipids are the building blocks of liposomes and cell membranes. Human skin, like the rest of the human body, is composed of cells whose membranes must be healthy and strong in order for them to function properly.

Lipids in general are hydrophobic, also called non-polar (not able to be mixed in water). However, the phosphate group in phospholipids is hydrophilic, also called polar (able to be mixed in water).

When phospholipids are immersed in water they arrange themselves so that their hydrophilic regions point toward the water and their hydrophobic regions point away from the water. This unique simultaneously hydrophilic/hydrophobic structure of phospholipids is the key to their ability to organize as a double layer (bilayer formation) when immersed in water. The interaction and rejection forces between phospholipids and water cause phospholipids to organize themselves e a as bilayers. Phospholipid bilayers are the core structure of liposome and cell membrane formations. A very small liposome (single-bilayer) is referred to as a nanosome.

Merely by mixing lipid (oil) with water, one can create liposome structures in single layered vesicles (SV) or multi-layered vesicles (MLVs). The physical properties of lipid and water yield a spherical shaped vesicle.

Cholesteryl Esters

A sterol alcohol, e.g., cholesterol, can replace one of the triglycerides a fatty acid lipid to become a lipid sterol. A sterol alcohol cholesterol can also become esterified to become a cholesterol ester. Unlike a lipid, this cholesteryl ester has only one tail.

Cholesterol has the structural formula:

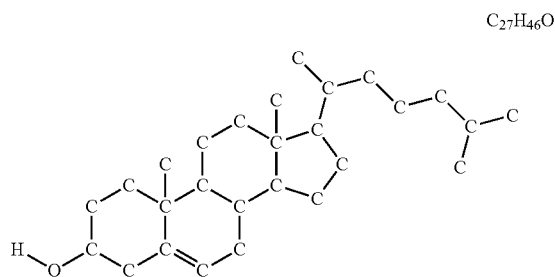 [SMILES: CC(C)CCCC(C)C1CCC2C3CC=C4CC(O)CCC4(C)C3CCC12C]

The H atoms are not shown in the structural formula for clarity.

Fatty acid esters of cholesterol constitute about two-thirds of the cholesterol in the plasma. Cholesterol is the main sterol present in animal tissues but other sterols may be present in biological extracts prepared from vegetables.

Cholesteryl esters, i.e., with long-chain fatty acids linked to the hydroxyl group, are much less polar than free cholesterol and appear to be the preferred form for transport in plasma and for storage. Those in plasma are synthesised largely by transfer of Fatty acids from position sn-2 of phosphatidylcholine by the enzyme lecithin-cholesteryl acyl transferase (LCAT). Cholesteryl esters are major constituents of the adrenal glands, where esters of steroidal hormones, may also be present at low levels. The latter may be a biologically inert storage form. Esters with long chain fatty acids are a common form of transport and storage of cholesterol. Cholesteryl linoleate is one of the most abundant cholesteryl ester species in human plasma.

Cholesteryl esters are prevalent in animal body fluids as plasma lipoproteins, and may be found in vessel walls as fatty streaks in atherosclerosis. The accumulation of cholesteryl esters in the arterial intima is a characteristic feature of atherosclerosis. Acylated sterols are also found in plant structures, their characteristics are similar to those of cholesteryl esters.

Lipids and proteins can form monolayers on both extra and intracellular leaflets of bilayer membranes, as well as other assemblies such as lipoproteins and micelles. Interfacial binding is an important mode of interaction for many lipid enzymes as well as effectors of lipids. It is governed by electrostatics at the interfacial region and the characteristics of lipids head groups. The interior portion of a lipid assembly, e.g., the bilayer interior, contributes with interactions that arise from the hydrophobic parts of lipid molecules that play a role in the regulation of membrane channels for example.

BRIEF SUMMARY OF THE INVENTION

With reference to the corresponding parts, portions, or surfaces of the disclosed embodiment, merely fix the purposes of illustration and not way of limitation, the present invention provides a vesicle called a cholestosome, having an single layered or multi-layered outer membrane made of cholesteryl esters of various sizes and lengths. The variety of lengths of the cholesteryl esters results in a pocketed membrane surface. In a preferred embodiment, the vesicle is generally spherical in shape, however other shapes are also possible, e.g., oval and tubular.

The cholestosome is a hollow vesicle enclosing a compartment capable of holding drugs or other compounds. Upon contact with the cell of interest, the cholestosome membrane fuses with the cell membrane and the contents of the cholestosome are introduced into the cell, or in the alternative the cholestosome passes into the cell carrying its contents.

In view of the foregoing, the invention broadly comprises a chemical composition including a plurality of cholesteryl esters arranged to form a vesicle. In several embodiments, all of the plurality of cholesteryl esters have a same molecular length, which in some embodiments provides a vesicle having a generally smooth outer surface, while in other embodiments, a portion of the plurality of cholesteryl esters have different molecular lengths, which in some embodiments provides a vesicle having a generally irregular outer surface. In yet further embodiments, a shape of the vesicle is selected from the group consisting of spherical, oval, disc-like, tubular and polyhedral shapes, and in yet other embodiments, a wall of the vesicle is selected from the group consisting of a monolayer and a bilayer, in still further embodiments, the chemical composition further includes a polyethylene glycol coat of mixed polymer size. In some embodiments, the plurality of cholesteryl esters include at least two different cholesteryl esters, and in some of these embodiments, the at least two different cholesteryl esters are selected from the group consisting of: cholesteryl myristate cholesteryl laurate cholesteryl dodeconate, cholesteryl palmitate, cholesteryl arachidonate, cholesteryl behenate, cholesteryl linoleate, cholesteryl linolenate, cholesteryl oleate and cholesteryl stearate. In yet further embodiments, the composition is clear dispersed in both hydrophilic and hydrophobic systems, and in some of these embodiments, the composition is smaller than wavelengths of visible light.

The invention also broadly comprises a method of delivering a drug to a cell comprising the steps of: a) combining a pharmaceutically effective amount of at least one drug with at least one cholestosome; and, b) utilizing the at least one cholestosome to introduce the drug to the cell. In some embodiments, the method further includes the step of: c) depositing the at least one drug within the cell.

Additionally, the invention broadly comprises a method of manufacturing at least one cholestosome including the steps of: a) mixing at least one cholesteryl ester in a first solvent to form a composition; b) mixing the composition of step a) with a second solvent until the at least one cholesterol ester, the first solvent and the second solvent form a homogenous dispersion; and, c) evaporating the first solvent leaving the at least one cholestosome in the second solvent.

Furthermore, the invention broadly comprises a method of manufacturing a drug delivery system including the steps of: a) mixing at least one cholesteryl ester in a first solvent to form a composition; b) mixing the composition of step a) and at least one drug in a pharmaceutically effective amount in a second solvent until the at least one cholesteryl ester, the first solvent, the at least one drug and the second solvent form a homogenous dispersion; and c) evaporating the first solvent leaving at least one cholestosome in the second solvent, wherein the at least one drug is combined with the at least one cholestosome. In some embodiments, the drug is contained within the cholestosome, while in other embodiments, the first solvent is a non-polar solvent and the second solvent is a polar solvent.

Moreover, the invention also broadly comprises a drug delivery system manufactured by the steps including: a) mixing at least one cholesteryl ester in a first solvent to form a composition; b) mixing the composition of step a) and at least one drug in a pharmaceutically effective amount in a second solvent until the at least one cholesteryl ester, the first solvent, the at least one drug and the second solvent form a homogenous dispersion; and, c) evaporating the first solvent leaving at least one cholestosome in the second solvent, wherein the at least one drug is combined with the at least one cholestosome. In some embodiments, the drug is contained within the cholestosome.

Accordingly, a general object of the present invention is to provide an improved drug delivery system capable of specifically targeting a tumor cell.

Another object is to provide an improved delivery system for immunotherapeutics.

Another object is to provide an improved delivery systemic for palliative agents.

Another object is to provide ail improved delivery system for apoptotic compounds.

Another object is to provide an improved delivery system with a pocketed membrane, where the pockets carry a positive or negative charge.

Another object is to provide cholestosomes much smaller than conventional liposomes.

These and other objects and advantages of the present invention will be readily appreciable from the following description of preferred embodiments of the invention and from the accompanying drawings and claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The nature and mode of operation of the present invention will now be more fully described in the following detailed description of the invention taken with the accompanying drawing figures, in which.

DETAILED DESCRIPTION OF THE INVENTION

Figure 1:
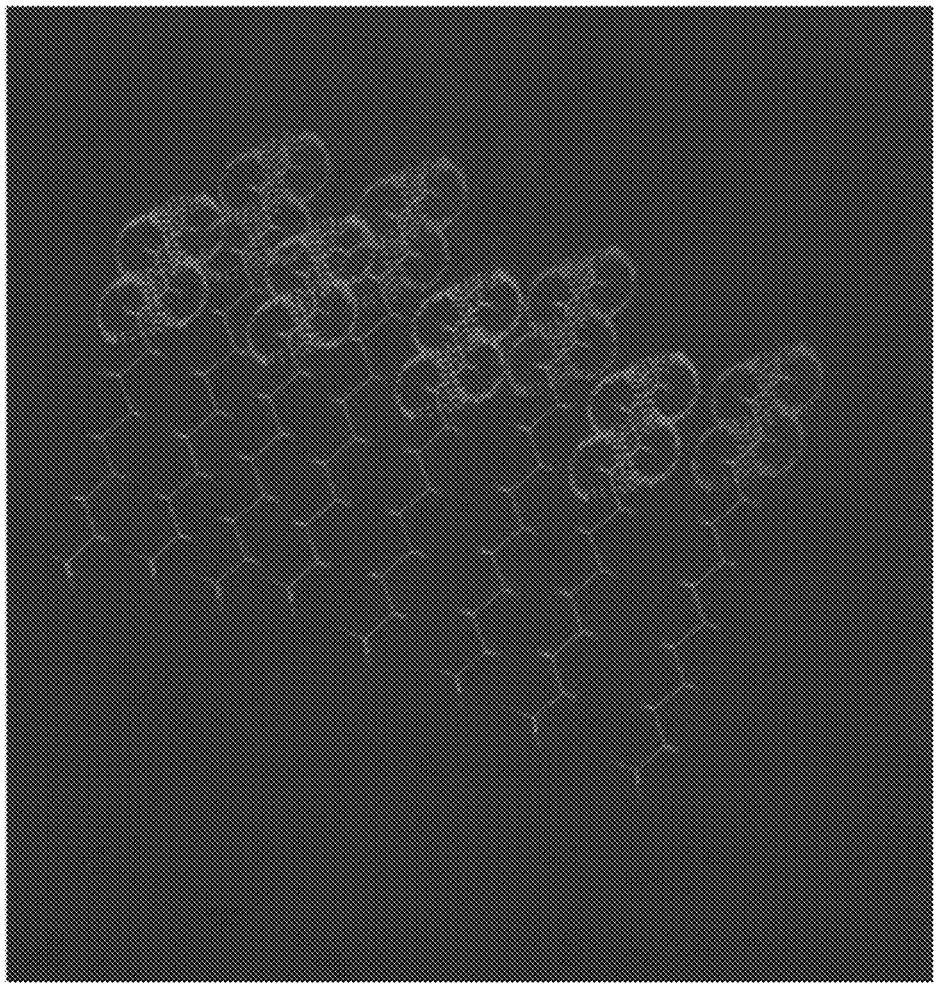
FIG. 1 is a diagram of a present invention cholestosome membrane.

At the outset, it should be appreciated that like drawing numbers on different drawing views identify identical, or functionally similar, structural elements of the invention. While the present invention is described with respect to what is presently considered to be the preferred aspects, it is to be understood that the invention as claimed is not limited to the disclosed aspects.

Furthermore, it is understood that this invention is not limited to the particular methodology, materials and modifications described and as such may, of course, vary. It is also understood that the terminology used herein is for the purpose of describing particular aspects only, and is not intended to limit the scope of the present invention, which is limited only by the appended claims.

Unless defined otherwise, all technical and scientific terms used herein have the same meaning as commonly understood to one of ordinary skill in the art to which this invention belongs. Although any methods, devices or materials similar or equivalent to those described herein can be used in the practice or testing of the invention, the preferred methods, devices, and materials are now described.

Cholestosomes provide a method of delivering a drug or combination of drugs to an individual's specific tumor based on that individual's specific tumor characteristics. Cholestosomes are created from various sized cholesteryl esters via self organization or other methods. The differing molecular lengths of cholesteryl esters create a pocketed or punctated membrane having a surface like a golf ball with several depressions. Binding multiple activated antibodies to the membrane of the cholestosome confers specificity to an individual tumor.

In addition to common spherical non-ionic surfactant vesicles (niosomes), disc-like, tubular, and polyhedral niosomes have also been reported. The permeability and osmotic activity of niocholestosomes are important in determining their use as controlled-release drug delivery systems.

The soma, or the body of the cholestosome, may be composed of natural molecules, synthetic molecules, or a combination thereof. Utilizing various sized cholesteryl esters to create the soma results in a punctated membrane, or a membrane with several depressions and bumps. The somal verge is the exterior surface, or the membrane of the cholestosome.

Cholesteryl esters differing in chain length as well as bonding characteristics will develop packing arrangements as a function of the concentration of the individual esters and will form unique vesicles based upon the co-solubility of the esters as a function of their individual concentrations. Their internal cavities can bind one or more types of molecules and the external surface can bind multiple targeting tools. The internal environment of the vesicle can be controlled to allow for reactions within the environment. Proximity of the internal components and reactions in this internal environment can be controlled as a function of time needed for delivery. Overall these properties have tremendous implications the targeted delivery.

Preliminary studies have been carried out on the binary combinations of all pairs of oxysterols as well as many pairs of cholesteryl esters Fatty acids are still being examined. Studies of the cholesteryl esters have been classified as a function of their degree of saturation. Consider for example the phase diagrams of the two esters, cholesteryl myristate and cholesteryl laurate, as discussed infra. Structural studies show that they are co-soluble with each other and that the experimental melts are closely aligned with the theoretically predicted values. The results also indicate minimum energy conformations which can be used as the basis of the molecular modeling studies. The studies of the saturated and unsaturated esters reveal differential degrees of co-solubility. For example cholesteryl dodeconate and cholesteryl myristate are not co-soluble except at the extremes of the mole fraction diagrams. Cholesteryl dodeconate and cholesteryl palmitate are not co-soluble under any mole fraction range. These preliminary binary studies show possible combinations of lipids to use in the cholestosome design. The studies have also shown which are not going to be possible without fractionation of the device. They also show that small amounts of interesting esters may be used as anchors to hold molecules if they are designed at low concentrations.

Figure 2:
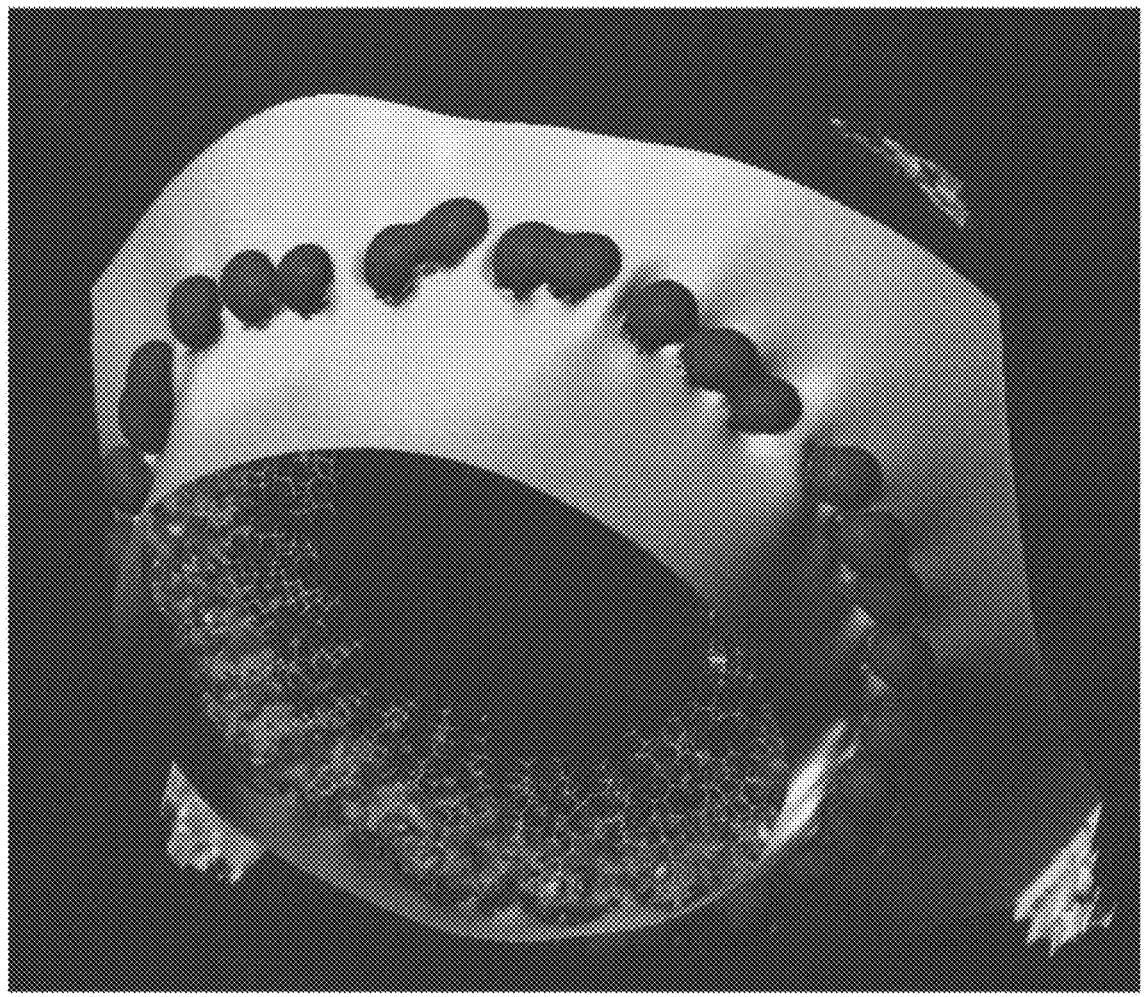
FIG. 2 is an isopotential model of a present invention cholestosome.
Figure 3:
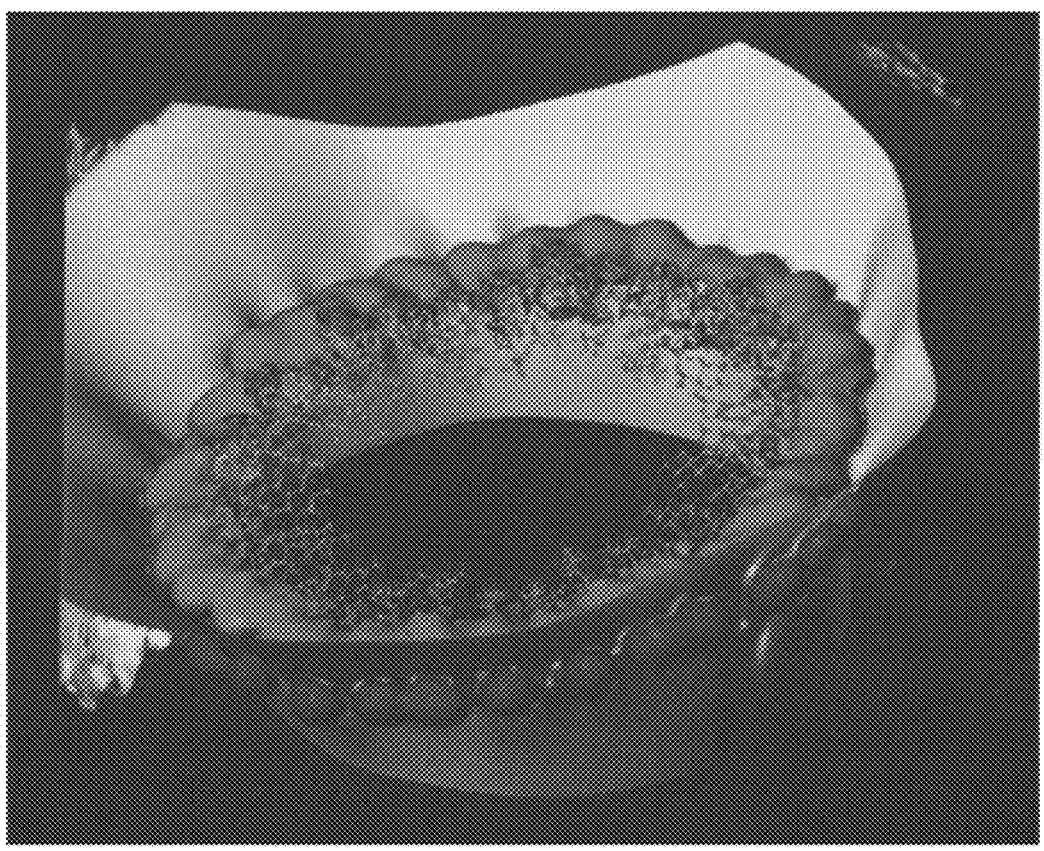
FIG. 3 is an isopotential model of a present invention cholestosome.
Figure 4:
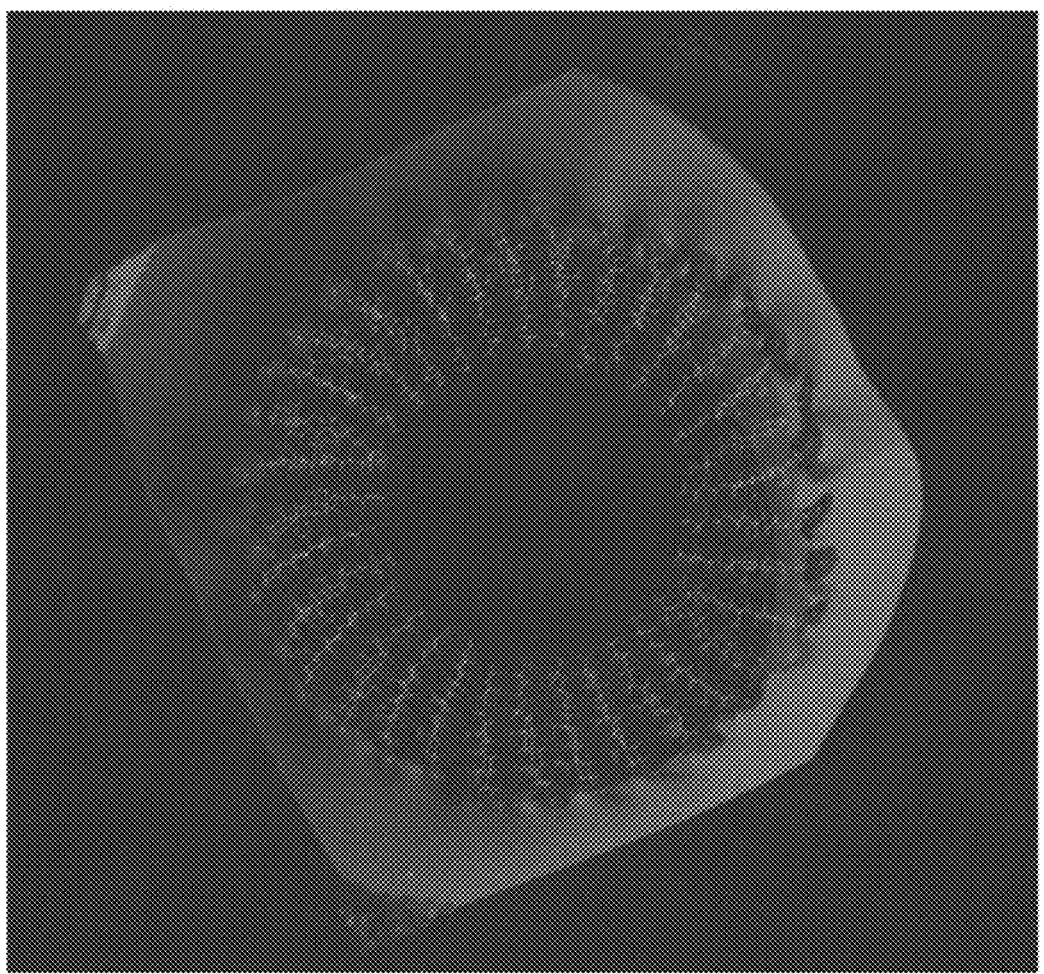
FIG. 4 is an isopotential model of a present invention cholestosome.
Figure 5:
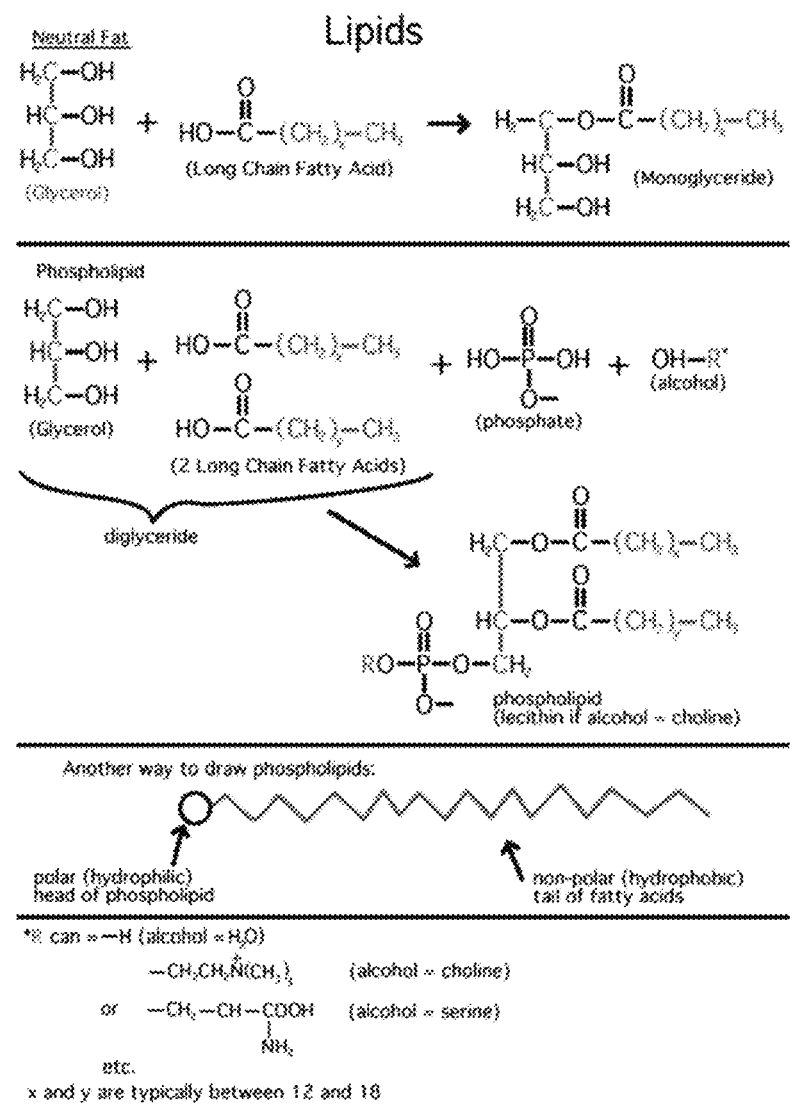
FIG. 5 is an example of phospholipids.

As can be seen in FIGS. 2 and 3, models of the cholestosome were built using SYBYL on an HP workstation. The structures were build and packed to minimize space or "holes" consistent with physical chemistry studies of lipids. The model built structures were then optimized using molecular mechanics and dynamics force fields for Tripos. Charges were then calculated and isopotential maps were generated for the models. The models, as seen in FIGS. 2 and 3, suggest that there is a natural cavity and charge distribution that is a function of the structure and packing of the molecules. The color of the potential density reflects charge separation as a function of packing: red—negative density; blue—positive density; and, the yellow surface indicates a transition between the two mapped potential surfaces. Models show that the electrostatic potential regions can be modified as a function of concentration differences and structural modification.

The size of these spheroids can be very small depending on the design and the nature of the esters. As illustrated in FIGS. 2 and 3, models of the spheroids are hollow inside or can have hollowed out cavities. The modeling studies show that the internal environment of the spheroid can bind one or more types of molecules and the external part of the cavity can bind multiple types of directional and marking molecules. The creation of this spheroid shape using molecular modeling techniques suggests that there would be an increase in the formation of space, pockets, caves, indentations, etc., to provide for better and increased binding to the cholestosome. The design of the cholestosome as the carrier mechanism for delivering active ingredients directly to a cellular level has extensive implications for targeted delivery. This design could for example allow for two to three activated antibodies to be strung together to insure and secure cholestosome tumor adhesion and not cholestosome normal cell adhesion thus specifically delivering to a target site.

Preparation of Cholesteryl Ester Liposomes and Conventional Liposomes

Figure 80:
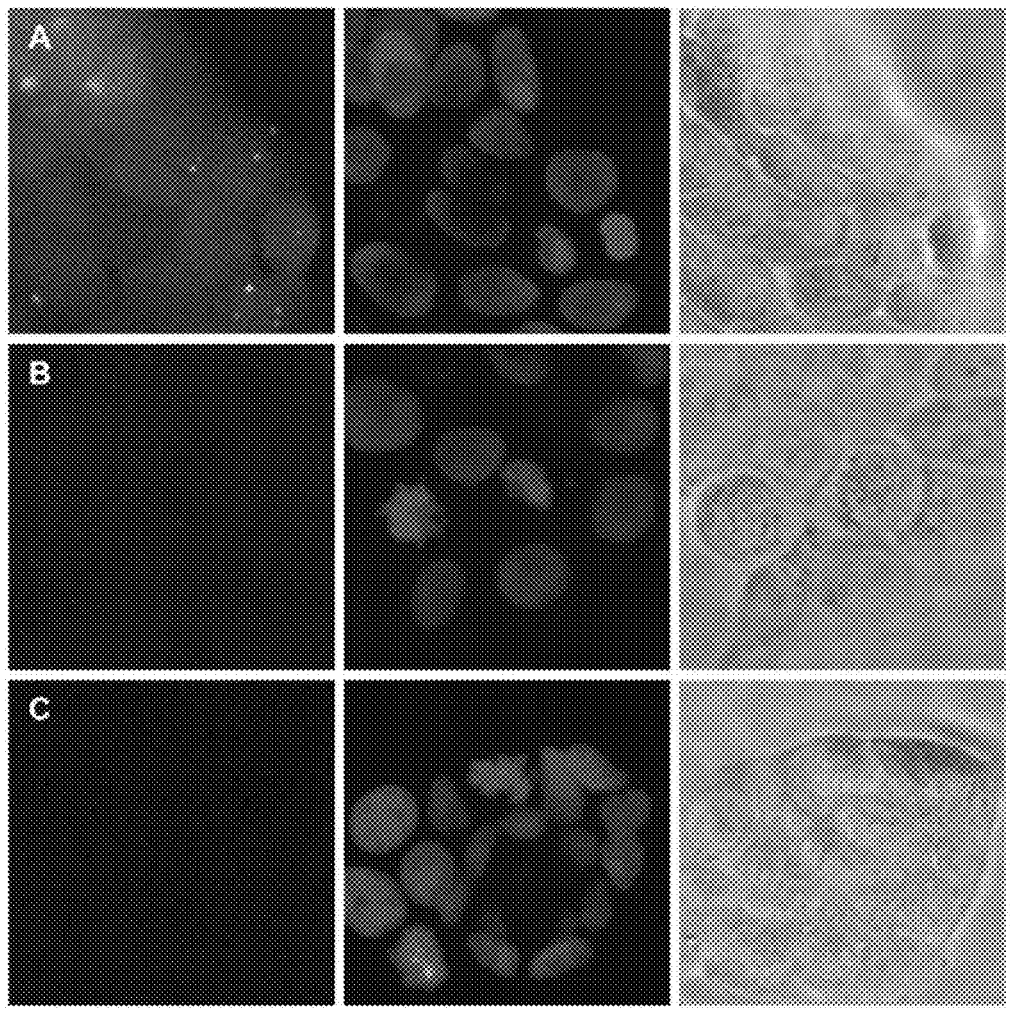

Cholestosomes and conventional liposomes are prepared using the reverse phase evaporation method (REM). The REM is performed using a rotary evaporator capable of being purged with Nitrogen. Various ratios of cholesteryl esters, for example, 0.1013 grams of cholesteryl myristate and 0.0970 grams of cholesteryl laurate (for cholestosomes); or dipalmitoylphosphatidylcholine (DPPC) and cholesterol (for conventional liposomes) are dissolved in 10 ml of ethyl ether in a 25 ml flask. Each mixture is placed on the rotary evaporator and the solvent driven off under a constant Nitrogen stream. Once dry, each mixture is resuspended in aqueous solvent. Vesicles are prepared by standard REM and also with, the inclusion of a stabilization step incorporating a polyethylene glycol coat of mixed polymer size (PEGylation or PEG stabilization). Various ratios of PEG to cholesterol ester/lipid combinations are examined for their effect on vesicle production and function. To determine cholestosome entrapment capabilities parallel preparations include a fluorochrome during ester mixing, prior to evaporation. Both fluorescein isothiocyanate (FITC, green fluorescence; MW=389) and oregon green (OR, also fluoresces green; MW=412.3) are tested as fluorochromes. FIG. 80 shows cells after: interaction with cholestosomes having fluorescent labels (Row A); interaction with free fluorescent labels in solution (Row B); and, interaction with neither cholestosomes nor free fluorescent labels in solution (Row C). Column chromatography and dialysis, as appropriate, are used to separate unencapsulated targets. Amounts of encapsulated targets are determined by fluorescence (fluorochromes) and reported as a percentage of starting material. Vesicles (encapsulating or non-encapsulating) are sized by extrusion through polycarbonate filters.

REM typically produces preparations containing, large unilamellar vesicles (LUVs). LUVs can also be produced by sonication of rehydrated larger multilamellar vesicle (LMV) suspensions. Sonication, using either bath or probe type instruments, typically produces small (15-50 nm diameter) unilamellar vesicles (SUVs) from LMV suspensions. Batch to batch variability, vesicle fusion and contamination of preparations with titanium make this method for vesicle production somewhat inferior for the routine production of suspensions containing LUVs of approximately uniform diameters. In general, extrusion results in the production of suspensions with reproducible mean particle sizes close to the filter pore size. Therefore, cholestosome preparations are extruded to produce liposomal suspensions with mean diameters of 100 nm and 200 nm. Extrusions are performed using the Avanti Mini-Extruder (Avanti Polar Lipids, Alabaster, Ala.). Suspensions are prefiltered through a large pore size filter before multiple extrusions through the smaller pore size filters. All extrusions are performed at a temperature above the gel-liquid crystal transition temperature (Tc) of the cholesteryl ester or lipid mix being used for cholestosome/liposome preparation. Each vesicle preparation is analyzed for lipid content using gas chromatography mass spectrometry (GCMS). Percent recovery of lipids as vesicles is calculated for each extrusion preparation. All vesicle preparations are frozen in liquid nitrogen, lyophilized, sealed under argon gas and stored at 4° C. until use.

Another embodiment of the present invention includes a method of manufacturing a present invention cholestosome according to the following procedure. A rotary evaporator is turned on and an attached water bath is set to a desired temperature, e.g., ~30° C., and the water flow is started to the rotary evaporator's condenser and checked for leaks. Purified nitrogen is turned on and set to purge the system. After five minutes a round bottom is attached to further purge the system. The organic phase is then prepared by combining cholesterol esters, for example two esters in an equal molar mixture of 1:1, in a round bottom flask. A first solvent is then added to the flask, e.g., a non-polar solvent such as ether, and the cholesterol esters are dissolved. At this time, reverse-phase vesicles are formed. Once the esters are completely dissolved, the flask replaces the round bottom on the system and is purged for 5 min with nitrogen. After the 5 min purge, a second solvent is added, e.g., an aqueous phase such as water. The two phase system is then sonicated until the mixture becomes a homogenous one phase dispersion. It has been found that in some instances the single phase mixture may begin to separate into two phases, however has not presented issues for the manufacture of the final product. The mixture is then placed on the rotary evaporator and the organic phase, i.e., the first solvent, is removed until it is observed that the first solvent is removed. The resulting cholestosomes are called reverse-phase evaporation vesicles (REV).

A further embodiment of the present invention includes a method of manufacturing a present invention cholestosome combined with at least one drug according to the following procedure. A rotary evaporator is turned on and an attached water bath is set to a desired temperature, e.g., ~30° C., and the water flow is started to the rotary evaporator's condenser and checked for leaks. Purified nitrogen is turned on and set to purge the system. After five minutes a round bottom is attached to further purge the system. The organic phase is then prepared by combining cholesterol esters, for example two esters in an equal molar mixture of 1:1, in a round bottom flask. A first solvent is then added to the flask, e.g., a non-polar solvent such as ether, and the cholesterol esters are dissolved. At this time, reverse-phase vesicles are formed. Once the esters are completely dissolved, the flask replaces the round bottom on the system and is purged for 5 min with nitrogen. After the 5 min purge, a second solvent including at least one drug is added, e.g., an aqueous phase such as water having at least one drug contained therein. The two phase system is then sonicated until the mixture becomes a homogenous one phase dispersion. It has been found that in some instances the single phase mixture may begin to separate into two phases, however has not presented issues for the manufacture of the final product. The mixture is then placed on the rotary evaporator and the organic phase, i.e., first solvent, is removed until it is observed that the first solvent is removed. The resulting cholestosomes are called reverse-phase evaporation vesicles (REV).

Initial observations show a consistent circular pattern unique from the starting materials and suggesting that structures were formed. The residue was tested using differential scanning calorimetry (DSC) to show that the product was different than the original parents, as discussed infra. DSC has shown that REM can produce a lamellar structure based on the co-solubility studies.

Determination of Vesicle Size

Dynamic laser light scattering (DLLS) and flow cytometry are used to analyze the size distributions of the extruded and non-extruded material. Non-extruded material serves as a control for comparison of particle size distribution and lipid recovery for the extruded material. DLLS is performed using a N4 Plus Submicron Particle System (Beckman-Coulter, Fullerton, Calif.). Average mean diameters are reported along with a polydispersity index which indicates the relative homogeneity of each suspension. Flow cytometry analysis is also reported. Here the calibration of size distribution is through the use of fluorescent labeled latex beads of a size ranging from 40 nanometers to 1 micron. Analysis of each vesicle preparation always includes this standard calibration. The correlation between the bead diameter and the side scatter height signal allows classification of the lipid particles into different relative size ranges. Fluorescent flow cytometry size standards for this analysis are purchased from Polysciences, Inc (Warrington, Pa.). Size distributions for each size range are reported as a percentage of total particles.

Determination of Vesicle Structure and Composition

Ester/lipid composition and structure determinations were made using GCMS and NMR, respectively.

Cholestosome is a generic term for a vehicle designed using small molecule lipids based on the cholesterol molecular structure. These may include cholesteryl esters, oxidized cholesterols as well as fatty acids. These molecules are combined in a specific mole ratio to ensure co-solubility. DSC and X-ray results on the binary combinations of esters show ranges of co-solubility as well as concentration ranges that permit the formation of solid solution structures. The argument is that the mere mixing of at least two different esters with a hydrophilic solvent will follow the physical laws similar to larger lipids and form spherical or oval shaped vesicles. The use of esters of different physical sizes and properties provides an irregular punctuated outer membrane. This type of surface provides multiple optimal zones for binding. Moreover, the cholesteryl ester spheroid structure single layered and multi-layered vesicles results in a spheroid shape that has a high binding entrapment capacity. The high entrapment depends on maintaining a core during the process of spheroid formation and can be affected by the nature of the binding substance, its concentration, the nature of the esters used and their relative concentrations.

As discussed supra, cholestosomes, or cholesteryl ester structures in single-layered (SV) and multi-layered vesicles (MLVs), can be prepared by reverse-phase evaporation (REV) from ether/water emulsions, or by other methods including self-organization. Moreover, cholesteryl ester spheroid structures in single-layered vesicles (SV) and multilayered vesicles (MLVs) are capable of drug entrapment. The amount of drug entrapped in these vesicles prepared from water/organic solvent emulsions depends on maintaining a core during the process of spheroid formation. The core is maintained due to the hydrophilic nature of the cholesteryl esters "heads" and the hydrophobic state of their "tails". Furthermore, entrapment depends on drug, drug concentration, cholesteryl ester, cholesteryl ester concentration, and the container used to prepare the vesicles. As used above and hereinafter, entrapment and entrapping are synonymous to combining with, and all are used to indicate that a component is chemically combined and/or encapsulated with another component and/or structure.

Most lipids (including cholesteryl esters) have some polar character in addition to being largely nonpolar. Generally, the bulk of their structure is nonpolar or hydrophobic ("waterfearing"), meaning that it does not interact well with polar solvents like water. Another part of their structure is polar or hydrophilic ("water-loving") and will tend to associate with polar solvents like water. This makes them amphiphilic molecules (having both hydrophobic and hydrophilic portions). In the case of cholesterol, the polar group is a mere —OH (hydroxyl or alcohol).

Thus, in an aqueous solutions (such as drug solutions), the polar heads of cholesterylesters tend to face the polar, aqueous environment, while the hydrophobic tails tend to minimize their contact with water. The nonpolar tails of cholesteryl esters tend to cluster together, forming a cholesteryl ester bilayer or a micelle ("some", hence "cholestosome"). Micelles are monolayer spheres and can only reach a certain size, albeit bilayers can be constructed to yield areas of hydrophilicity for "aqueous" based drugs, with core areas for hydrophobicity "lipid" based drugs.

Micelles separate out from the polar milieu by a process known as the "hydrophobic effect." When dissolving a nonpolar substance in a polar environment, the polar molecules, i.e., water in an aqueous solution, become more ordered around the dissolved nonpolar substance, since the polar molecules cannot form hydrogen bonds to the nonpolar molecule. Therefore, in an aqueous environment, the polar water molecules form an ordered "clathrate" cage around the dissolved nonpolar molecule. However, when the nonpolar molecules separate out from the polar liquid, the entropy (state of disorder) of the polar molecules in the liquid increases. This is known as "self-organization" and is essentially a phase separation, similar to the spontaneous separation of oil and water into two separate phases when one puts them together.

The self-organization depends on the concentration of the cholesteryl esters present in solution. Below the critical micelle concentration the cholesteryl esters form a single layer on the liquid surface and are dispersed in solution. At the first critical micelle concentration (CMC-I), the cholesteryl esters organize in spherical micelles, at the second critical micelle concentration (CMC-II) into elongated pipes, and at the lamellar point (LM or CMC-III) into stacked lamellae of pipes. The CMC depends on the chemical composition, mainly on the ratio of the head area and the tail length.

Cholestosomes are very small, on the order of a nanometer, but significantly smaller than Conventional liposomes. As illustrated, the cholestosomes are hollow inside and enclose some of the drug or other compounds in which they were formed (inclusion or entrapment). When the cholestosomes reach the outside of a living tumor cell membrane in the tumor environment, the membranes will hybridize (fuse) and the contents of the cholestosome contents will be deposited intracellularly.

Due to their small size, cholestosomes will also target the cells of the tumor microenvironment, hybridization will also occur within the microenvironment, thereby resulting in total tumor targeting. While not wishing to be bound by any particular theory, it is believed that the cholestosome can function in different ways to introduce components to a cell. The cholestosome may adhere to the outer membrane of the tumor and deposit the encapsulated drugs. The drugs then disperse within the microenvironment of the tumor. Further, since the tumor has its own vascular system, the cholestosomes will also penetrate the inner milieu of the tumor microenvironment where they will adhere to the cell populations of the microenvironment and hence deliver their drug content to these cells. In the context of cancer treatment, e.g., with cancer cell selective chemotherapeutic agents, the totality of this assault is the death of just tumor cells while the nearby normal cells will be spared.

The spherical shape of the cholestosome results in the formation of "spaces", "pockets", "caves", "indentations", "punctuations", etc. which provide for binding sites, for example, antibody/membrane binding, while still allowing exposure of the actual antibody binding site to the tumor and decreasing immunogenicity.

Thus, cholestosomes are able to carry with them any enclosed substances into the tumor and to the individual cells, e.g. nutrients, antibiotics, chemotherapeutic agents, and even vectors for carrying DNA segments The ability of cholestosomes to act as the carrier mechanism for delivering active ingredients directly to the cell level has extensive implications for targeted tumor delivery of drug and drug cocktails. By themselves, cholestosomes are non-toxic and cause no toxicity. In the preferred embodiment, the cholestosome is comprised of natural lipid cholesteryl ester molecules, although it is contemplated that it may include synthetic molecules as an alternative. Chemotherapeutic agents can be tumor target specific, i.e., they may be preferentially absorbed or retained or may attack a tumor specific metabolic system. Embedded substances may affect immune competence including lymphocyte activation, cytokine release, phagocytosis, apoptosis, oxidative burst, natural killer cell activity, etc.

In a preferred embodiment for attacking tumor cells, the cholestosome can contain an apoptosis cocktail comprising: apoptosis stimulating or apoptosis inducing protein, apoptosis associated tyrosine kinase protein, perforin, granzyme and a membrane attack complex (MAC).

Perforin is a cytotoxin produced by T-Lymphocytes. They are stored in secretory vesicles within Tc (cytotoxic T-cells/CD8+) cells.

Granzymes are a group of serine/threonine proteases, including several iso-enzymes. Granzymes need to enter into the cytoplasm of the target cell, where they activate an intracellular protease pathway that eventually leads to apoptosis. If granzymes are prevented from entering the target cell, in the presence or absence of perforin, the target cell survives.

Co-Solubility Studies

Co-solubility studies were performed for a variety of components considered for use in manufacturing the above described cholestosomes. The following describes several aspects of the present invention, i.e., possible components of the cholestosome structure, and it should be appreciated that the present invention is not limited by the specific aspects described in these studies.

Atherosclerotic plaque is a mixture of lipids found in the blood stream and the arteries around the heart. The build up of this plaque is dangerous to a person's health because it causes a narrowing of the arterial walls. From the narrowing of the arterial walls, the heart has a harder time pumping blood throughout the body which can lead to congestive heart failure for those individuals. As a result of this plaque buildup, coronary heart disease is the number one killer of Americans. Therefore, the study of the composition of the atherosclerotic plaque and its mechanism of formation is critical in developing a better predictor of heart disease. By studying systems comprised of plaque components, ranging from one component up to complex multicomponent systems (including atherosclerotic plaque), it may be possible to develop a methodology for non-invasive procedures that could predict heart disease based on concentrations and packing structures of the differing oxysterols, cholesteryl esters and cholesterol within the plaque.

Thermodynamic studies of the plaque compounds are important because they lead to understanding, the stability of the components in the arteries. Atherosclerotic plaque buildup happens when damage occurs to the lining of the arteries, which prompts blood platelets to clump around the area of the injury. As cholesterol and other fats flow through the blood they will stick to these areas where the blood platelets collect and start to form a mass buildup which leads to the development of atherosclerotic plaque. Over time the pieces of plaque are able to break off and be transported in the blood stream. This leads directly to health problems such as strokes and heart attacks.

The packing of the components of the plaque is what determines the stability of the plaque on the arterial walls. If the components of the system are similar in structure, the possibility exists that they will form a packed structure which is homogenous among the different components. When homogeneity is not achieved, the packed structure may not require much energy or effort to break away from the rest of the plaque or may not form at all. This structural instability poses risks leading to stroke or heart attacks caused by the free floating plaque. Since plaque stability is related to structural packing, spectroscopic differentiation can be used to determine sample stability. To determine the structure of the packed plaques, three types of studies can be performed. First, there is the DSC work, which will show if the atherosclerotic plaque system is co-soluble or not. Next there is the use of solid state NMR with magic angle spinning (MASNMR) which can be used to determine the states that the system may be in at a certain temperature and composition. Studies have shown that this form of NMR has the ability to distinguish between different crystalline forms. This will allow for a correlation between structure and thermodynamic data to be derived. A third way of determining structural information from atherosclerotic plaque is by use of time resolved fluorescence of the plaque. A nitrogen laser outputs an excitation pulse of 337 nm for 3 ns onto the plaque, which is then sent through a MCP-PMT detector. From this, structural composition information is gained that relates stability of the plaque to the time-resolved fluorescence.

The dangers of atherosclerotic plaque buildup results not only from the narrowing of the arterial walls, but also from the fact that the compounds themselves are cytotoxic and can kill cells upon contact. Cholesterol, which is found in the body, can be oxidized to 25-hydroxycholesterol (25OH), 7-ketocholesterol (7-Keto), cholestane triol (CT), 7β-hydroxycholesterol (7B), or 20α-hydroxycholesterol (20A) by a process called auto oxidation. These compounds can then cause cell death of the arterial walls when they come in contact with them.

Research has been carried out to determine if vitamin E has any affect on the oxidation of cholesterol to these cytotoxic compounds. Since vitamin E is an anti-oxidant, there exists the possibility that it can be used to protect cholesterol from being oxidized. Research has shown that increased concentrations of vitamin E in the blood is effective in lowering the amount of some oxidized cholesterols present in the plasma, but not all of them. 7B concentration was monitored in the blood plasma after the sample was introduced with vitamin E. Results showed that the oxidation of cholesterol to its oxidized cholesterols can only be preferentially controlled. Results also showed that vitamin E was only effective in controlling the concentration of the oxysterol compounds if they were present in the plasma. Once the oxysterols were packed into the plaques, vitamin E was not able to reverse the concentrations in the plaques.

Oxidized sterols that are formed from cholesterol share several properties in common. For example, they can come from the cholesterol synthesis in the body. After the cholesterol is synthesized in the body, it becomes susceptible to auto-oxidation. The oxidation of cholesterol is what produces the different derivates that are studied from 25OH to 7-Keto and Cholestane Triol. The oxysterols are all oxygenated compounds, which have either one or more additional oxygen's relative to cholesterol. The oxysterols are all lipids, which promotes the ability to pass through cell membranes, the blood brain barrier, and even be physiological mediators in connection with numerous health issues, including heart disease.

The oxidized cholesterols differ from each other in positioning of the additional oxygens. For example 25OH and 20A have their second oxygen located on the tail, whereas 7B and cholestane triol (CT) have their oxygens located on the steroid ring, as discussed infra. As a result of the differential positions of the oxygens, different packed structures of the system are created. Due to this, the relationship between structural changes and packed structures needs to be explored.

The cytotoxicity of oxidized cholesterol depends on the conditions of exposure to the cells by the oxidized cholesterol. It has been shown that 25OH causes changes in the arterial smooth muscle cell, which can be the starting point for the progression of atherosclerotic plaque. By causing the cell death of the arterial smooth muscle cells, blood platelets will start to collect which will then trap free lipids in the plasma.

Of the oxidized cholesterol that, were studied, 7'-Keto is the most cytotoxic. Considering the structure of 7-Keto, and comparing it to 7B, which is the closest structural match to 7-Keto, a noticeable difference can be seen. The hydroxyl group that is, attached to the number 7 carbon in the 7B compound is oxidized from the hydroxyl group to the ketone group at the same location. In addition, it was shown both 7B and 7-Keto have cytotoxic effects when studied with cells of the vascular wall. Results showed that both oxidized cholesterol were able to induce apoptosis in both endothelial and smooth muscle cells. These oxidized cholesterol however did not cause apoptosis in fibroblasts; instead necrosis occurred in this case. Apoptosis and necrosis are both related to cell death, apoptosis is deliberate cell death whereas necrosis is a cell death that is caused by an acute cellular injury.

Aside from causing cell death, oxidized cholesterol also contribute to other problems in the body. These can range from advancing the development of atherosclerotic lesions to decreasing the expression of lipoprotein lipase mRNA in human monocyte-derived macrophages and the expression of other receptor sites. Along with those health problems, cholesterol gallstones are the most common form of gallstones found in western society. Cholesterol gallstones are classified as being composed of at least 70% cholesterol by mass.

High concentrations of oxidized cholesterol in the blood stream are known causes of heart disease. High cholesterol can lead to high blood pressure since the cholesterol can entangle with blood platelets to form atherosclerotic lesions as previously discussed. However, recent research has hypothesized that the concentration levels of 7B in the blood plasma can be used as a predictor of lung cancer. The benefit to development of 7B as a marker for lung cancer is that looking at the plasma concentrations of the 7B, can be determined by simple blood work. This could be a cost effective way of screening for lung cancer if it can be developed.

Co-solubility for the cholesteryl esters depends on several factors including tail lengths and the degree of unsaturation in the tail of the molecules in the binary system. For the oxidized cholesterol, co-solubility depends on the number of oxygens and the locations of the oxygens for the components of the system. Some systems show multiple legitimate peaks on the DSC graphs. This means that the components of the system are not co-soluble with each other. The individual molecules will tend to aggregate with like molecules and not mix with the other ones. When this occurs, there will be an intermediate state between the solidus and the liquidus line where a solid-liquid state will exist.

Construction of the phase diagram can be done in a variety of ways. The peak shape method was used in constructing the phase diagrams, which is one way to create phase diagrams. The peak shape method used the onset temperature, peak temperature and ending temperature ($T_o$, $T_s$, and $T_f$ respectively), and the data points associated with them to generate the phase diagrams. Mole fractions (MF) were used to generate the curves on the graphs ranging from 1:0 to 0:1 MF of the components in the system. These were determined by taking the masses of the samples and entering them into a computer program to calculate the mole fractions. After the data points were collected, they were entered into an excel spreadsheet under the correct column heading. The points taken from the DSC graphs for any peak which fell between the melting points provided three separate data points per peak. The first was the onset temperature ($T_o$) of the peak. Second was the peak temperature ($T_s$). The third point was the ending temperature of the peak ($T_f$).

When creating the phase diagrams, the mole fractions of one component of the system were plotted as the x-axis and the temperature was plotted in degrees Celsius on the y-axis. From the data points that were generated, the solidus line and liquidus line were generated. The solidus line ($T_o$) was defined as the transition point where the system starts to chance from a solid to a liquid for our work. The liquidus line ($T_f$) then is the point where the last of the solid in the system has changed from solid to liquid. In systems that are co-soluble, as was discussed above, only one set of points per experimental run will be collected and graphed. When systems move away from co-solubility, more than one set of points can be collected per experimental run.

If the phase diagrams were not co-soluble, then two or more peaks were shown on the DSC graphs. For each peak an onset, peak, and final temperature is obtained from the DSC graph. The second peak on the DSC graph then has its data points designated with a prime. Thus, $T_o'$, $T_s'$, and $T_f'$ correspond to the onset, peak, and final temperature of the second peak respectively.

When more than the one set of data points per experimental run are collected, the liquidus line is defined in a different way. The solidus line will still remain the same, because this is when the entire system begins to melt from a solid to a liquid. The liquidus line now is defined by the value $T_f'$, which is the ending, temperature of the highest melting peak on the DSC graph that can still be considered from the system. As the results for a few of the oxidized cholesterol will show and some of the cholesteryl esters as well, two distinct melting points are graphed. The area between the $T_o$ and $T_o'$ is composed of an intermediate phase that contains partial liquid and partial solid together in a solution. Once the temperature is above $T_f'$ the system has become completely liquid.

The ideal melting curve was created by taking the peak temperature ($T_s$) for the pure components of the system being studied, and they were then graphed at their respective mole fractions. From there a straight line connecting the two points was drawn, which represents the ideal melting curve. This curve is a graphic representation of the theoretical value for which the system should melt.

Not all the co-soluble graphs produced results that aligned directly on top of the theoretical line. Instead, two other results that were observed were positive and negative deviations from the ideal melt line. Positive deviations are those that have $T_s$ values above the ideal melting line. Negative deviations are observed as having $T_s$ values that lie below the ideal melt line. All of the co-soluble phase diagrams created one of these three types of results.

When the binary system undergoes the initial heating, both components will be in the liquid state once the melting point of the highest component is reached. Here, the components of the binary system will be able to move around and shift positions from where they first were in the packed structure. According to Raoult's Law, there is a relationship between the mole fraction of one component of the system and partial pressure it exerted. Due to this, once cooling begins, new crystal structures are created and solidified as the temperature of the binary system decreases. The new packed structures that are created are of importance since this is in theory how they will pack in the arteries to form the plaque.

Atherosclerotic plaque is a complicated system, of which not all the components are currently known. For that reason, the research began with the studies of single components in the DSC to observe the thermodynamic results. Next, the study of binary systems was carried out to observe the results of two compounds being mixed together. Data was collected for the oxidized cholesterol in combination with each other, and also cholesteryl esters in combination with each other. Only saturated cholesteryl esters were combined with other saturated cholesteryl esters and only unsaturated cholesteryl esters were combined with other unsaturated cholesteryl esters. Binary phase diagrams were then composed for those combinations. This provides a basis for the studying of interactions of the oxidized cholesterol with each other as a function of concentration. A similar procedure was used in the study of cholesteryl esters.

Sample preparation was consistent for all studies. The oxidized cholesterol and the cholesteryl esters were all purchased from Sigma (St. Louis, Mo.). Each sample was run in the DSC to determine if the experimental and the literature values agreed. Table 1 below contains the results for the oxidized cholesterol and Table 2 below contains the results for the cholesteryl esters. Discrepancies in melting points are seen for both the 20α-hydroxycholesterol (20A) and the 7β-hydroxycholesterol (7B). There was no attempt to purify the compounds. The esters results are close to the literature values for their melting point, and again no attempt was made to purify these compounds.

Initially an empty aluminum pan was placed on a Mettler Toledo AB204-S four place balance and zeroed out. A small pan was used for the pure compounds and larger pans were used for the binary combinations. The samples that were used ranged in size from 0.8-26.9 mg for the binary combinations, which are located in Table 6 and 7 below for the oxidized cholesterol and Tables 8, 9 and 10 below for the cholesteryl esters.

Before each sample was weighed out, the spatula that was used was rinsed with distilled water, acetone, and distilled water again, and wiped dry with a paper towel. After the first component of the binary mixture was added, the mass was recorded and then the balance was zeroed out again. The spatula was again rinsed as described above. The second component was added and the mass was recorded. A computer program was created for calculating mole fractions. After the pan was filled with the compounds to be analyzed, the pan was sealed with a lid using the DSC crimper.

A reference pan was created that was an empty DSC pan crimped with a lid on top of the pan. The reference pan was placed on the right thermocouple and the sample pan was placed on the left thermocouple inside the DSC. The inside and outside covers were placed in their correct places. The DSC was then set to heat from an initial temperature of 30.0° C. to a temperature that was 10° C. above the highest melting point of the system at a rate of 5.0° C./minute. A two (2) minute isotherm was then imposed on the sample at that temperature and then cooled to 30.0° C. at the same rate of 5.0° C./minute. This was done so that the two compounds would be fused together inside the pan. A second heating was then performed that went to about 30° C. higher than the highest melting point. The sample was then held again for 2 minutes at that temperature and then cooled at 5.0° C./minute to 30.0° C. The sample pan was then removed from the DSC and placed in a labeled compartment box.

The balance used was a Mettler Toledo AB204-S four place analytical balance. For ease of measurement the balance readout was in milligrams. A Pyris 6 DSC from PerkinElmer was used for running the actual samples. A supply of pre-purified nitrogen was used as the carrier gas. The software was also from Pyris and was run on a Dell computer with the Windows XP Professional version 2002—service pack 1 for the operating system. The Thermal Analysis version 7.0.0.0110 was used in all calculations of the data points. The calibration of the DSC was performed by taken known standards of Zinc and indium from PerkinElmer and running them in the DSC and then putting the corrected and experimental values into the DSC calibration files.

Figure 79:
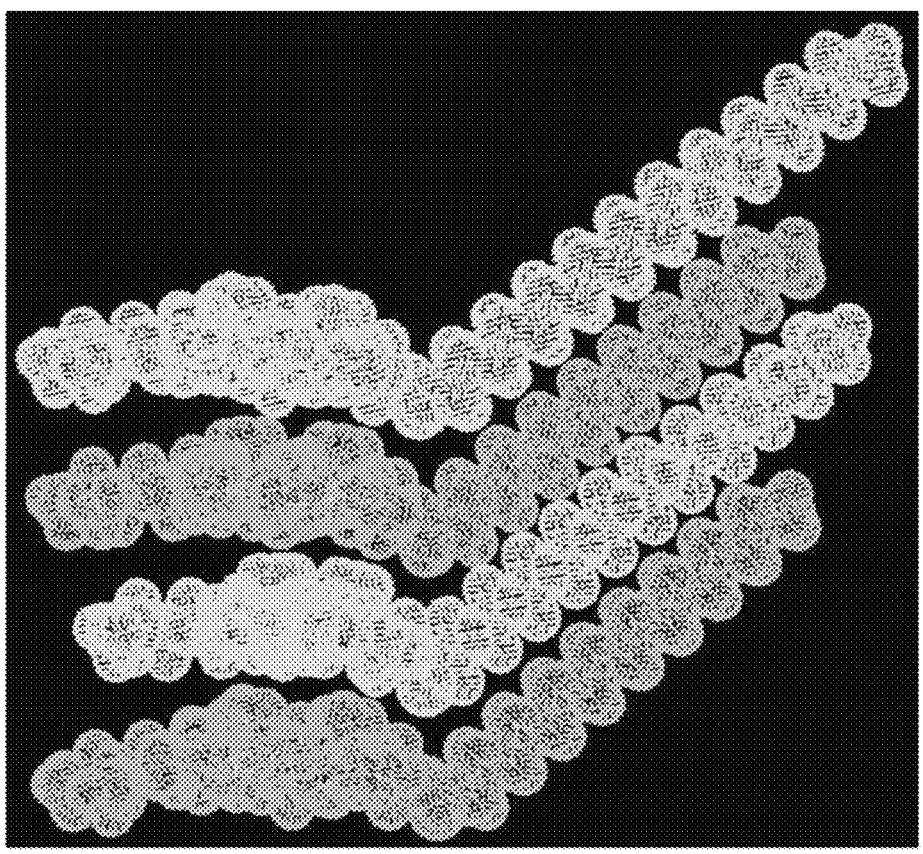
FIG. 79 shows the packing Cholesteryl Stearate and Cholesteryl Behenate; and, FIG. 80 shows photomicrographs of cells showing presence of a fluorescent indicator, photomicrographs of cells showing staining of the nuclei and photomicrographs of cells.

Tripos's SYBYL® 7.0 Discovery software for computational chemistry and molecular modeling was run on a HP workstation XW 8000 to create the molecular modeling pictures shown in FIGS. 57 through 78 for the oxidized cholesterol and FIG. 79 for the cholesteryl esters. The HP workstation uses dual 3.2 GHz processors with 533 MHz front side bus, contains 2 GB of memory along with a 73 GB SCSI hard drive. The workstation runs Linux Red Hat version 3.32.

TABLE 1

Physical Constants Oxidized Cholesterols

| Oxidized cholesterol | DSC Peak $T_s$ (° C.) | Lit. Value Melting Point (° C.) | Purity | Experimental Heat of Formation (kcal/mol) | Lit. Value Heat of Formation (kcal/mol) |
|---|---|---|---|---|---|
| Cholesterol | 149.12 | 150.7 | 95% | 6.78 | 5.08 |
| 25-Hydroxy-cholesterol | 183.88 | 178-180 | Min. 98% | 11.70 | 9.16 |
| 20α-Hydroxy-cholesterol | 120.81 | 125-132 | Min. 98% | 6.513 | N/A |
| 5-Cholesten-3β-ol-7-one (7-keto-cholesterol) | 171.51 | 170-172 | Min. 90% | 5.55 | 5.46 |
| Cholestane-3β-5α,6β-triol | 241.99 | 238.5-241 | Min. 98% | 8.837 | 7.49 |
| 7β-Hydroxy-cholesterol | 156.14 | 172-176; 180-181 | Min. 95% | 3.674 | N/A |

TABLE 2

Physical Constants of Cholesteryl Esters

| Cholesteryl Esters | Obsserved Melting Point (° C.) | Lit. Value Melting Point (° C.)$^B$ | Purity | Experimental Heat of Formation (kcal/mol) | Lit. Value Heat of Formation (kcal/mol) |
|---|---|---|---|---|---|
| Cholesteryl Arachidonate | 24.73 | 24-24.5 | Min. 95% | 3.539 | N/A |
| Cholesteryl Behenate | 90.19 | 87.5-88.0 | Min. 90% | 20.847 | N/A |
| Cholesteryl dodecanoate (laurate) | 94.31 | 91-92 | Min. 98% | 7.125 | N/A |
| Cholesteryl Linoleate | 43.82 | 42.0 | Min. 98% | 7.551 | N/A |
| Cholesteryl Linolenate | 38.40 | 32-33 | Approx. 99% | 6.850 | N/A |
| Cholesteryl Myristate | 71.89 | 70-70.5 | Min. 99% | 10.048 | N/A |
| Cholesteryl Oleate | 50.85 | 46.5-47.0 | Min. 98% | 12.106 | N/A |
| Cholesteryl Palmitate | 79.11 | 77-78 | Min. 98% | 14.027 | N/A |
| Cholesteryl Stearate | 84.13 | 81.5-82.5 | Min. 98% | 14.633 | N/A |

Figure 6A:
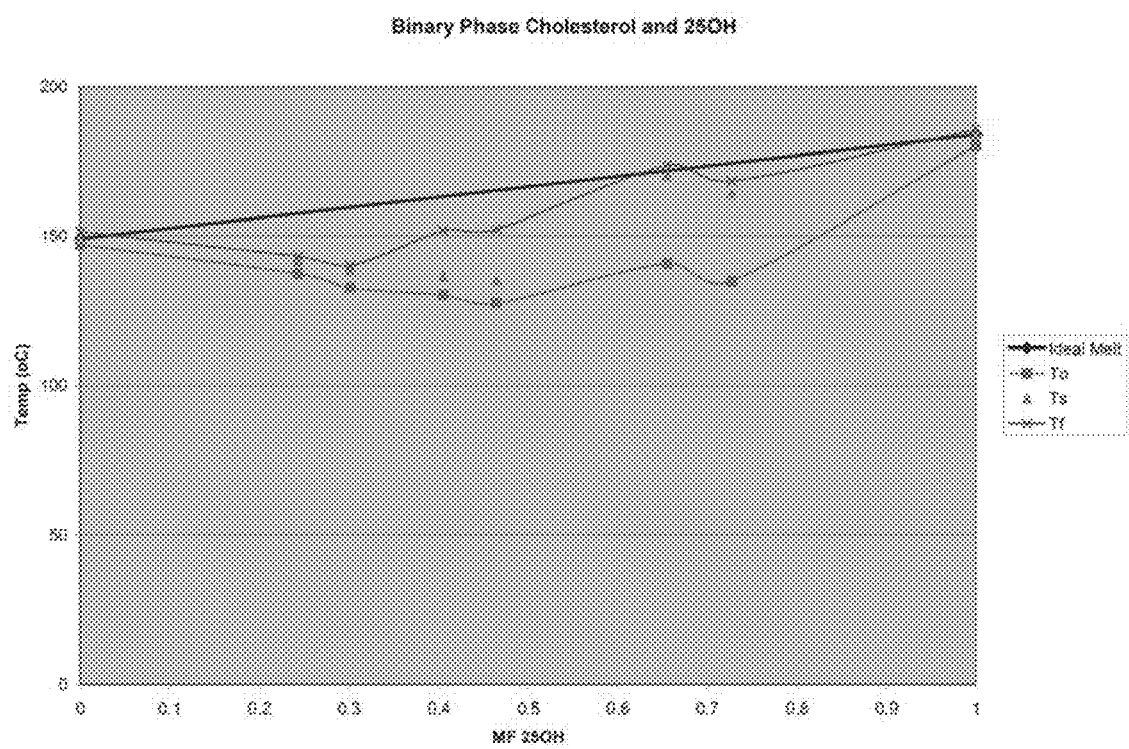
FIG. 6A is a graph of the binary combination of Cholesterol with 25-OH.
Figure 6B:
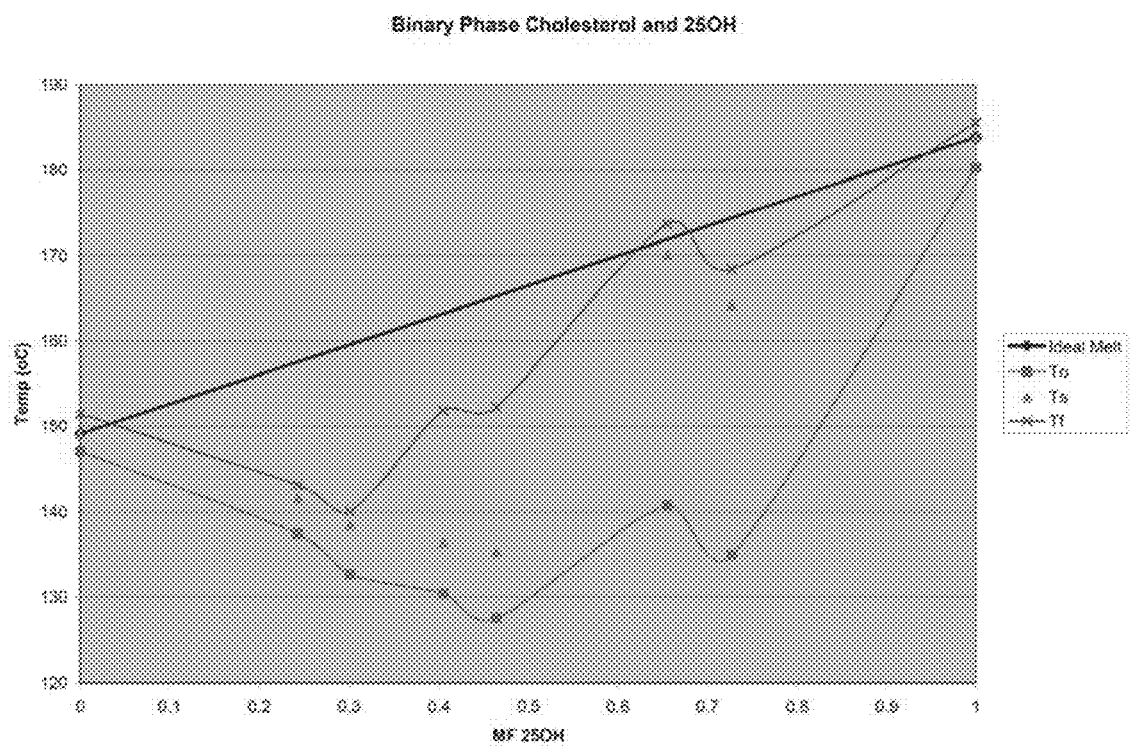
FIG. 6B is an expanded graph view of Cholesterol and 25-OH.

The graphs in FIGS. 6A and 6B show that over all concentrations, 25OH is co-soluble with cholesterol. As the graphs show, all the points for the solidus line lie below the ideal melt line, which is expected based on Raoult's Law. The expanded view shows that the maximum deviations from the ideal line around 0.4-0.7 MF of 25OH are not seen. Instead the curves of the solidus and liquidus line are more uniform, and show a general trend of decreasing to a minimum around 0.5 MF of 25OH and then starting to increase in melting temperature again.

Figure 7A:
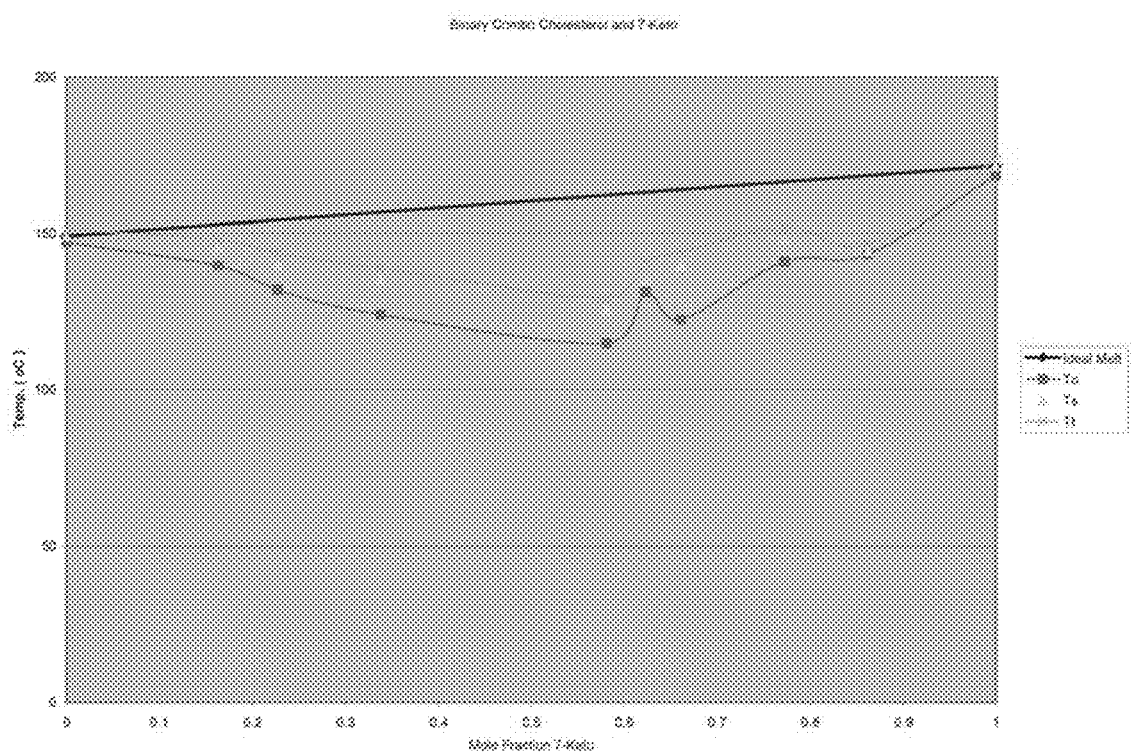
FIG. 7A is a graph of the binary combination of Cholesterol with 7-Keto.
Figure 7B:
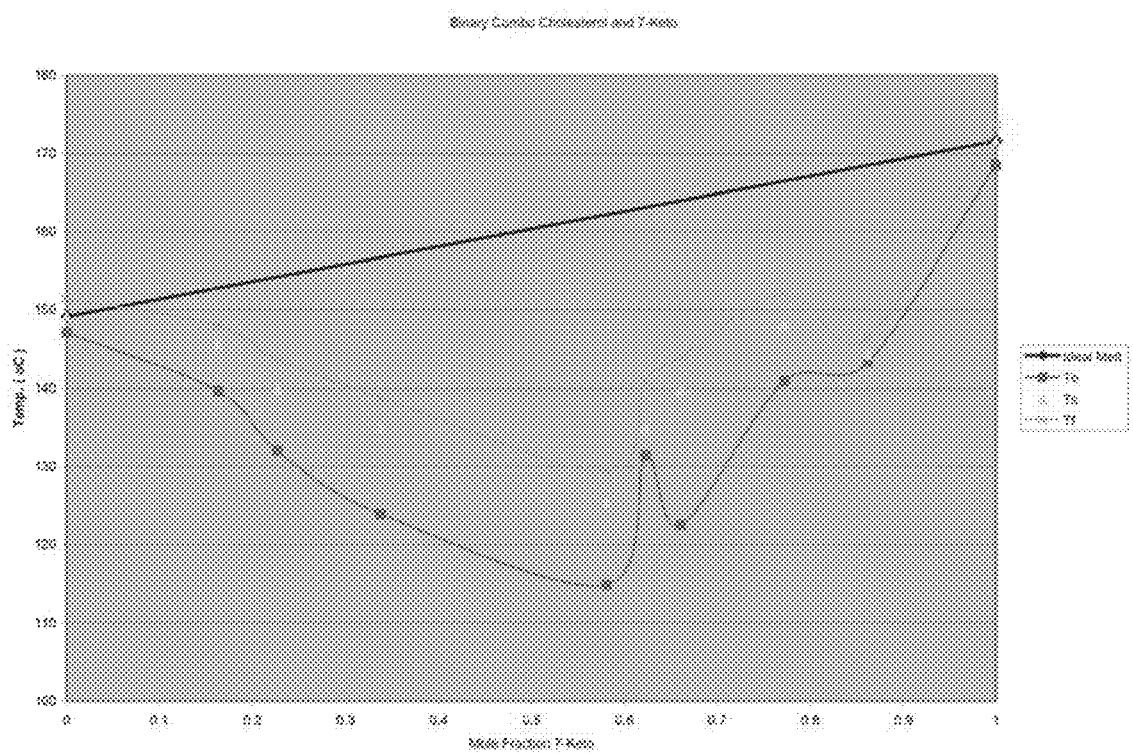
FIG. 7B is an expanded graph view of Cholesterol and 7-Keto.

The graphs in FIGS. 7A and 7B show that the binary system of cholesterol and 7-Keto are co-soluble over all concentrations. A minimum melt temperature appears around 0.6 MF of 7-Keto, at which point the solidus line changes from decreasing in melting temperature to increasing in melting temperature. The expanded view of FIG. 7A shows that there is a general trend of decreasing followed by an increasing in both the solidus line and the liquidus line with the minimum occurring at 0.6 MF of 7-Keto.

Figure 8A:
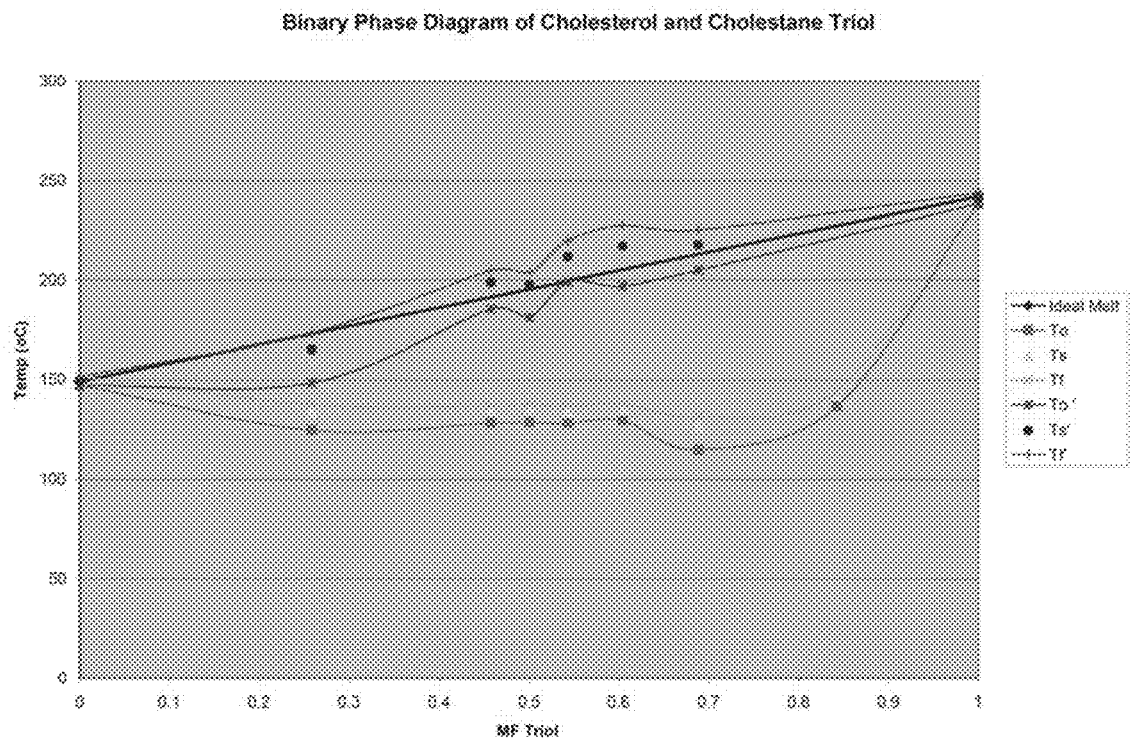
FIG. 8A is a graph of the binary combinations of Cholesterol and Cholestane Triol.
Figure 8B:
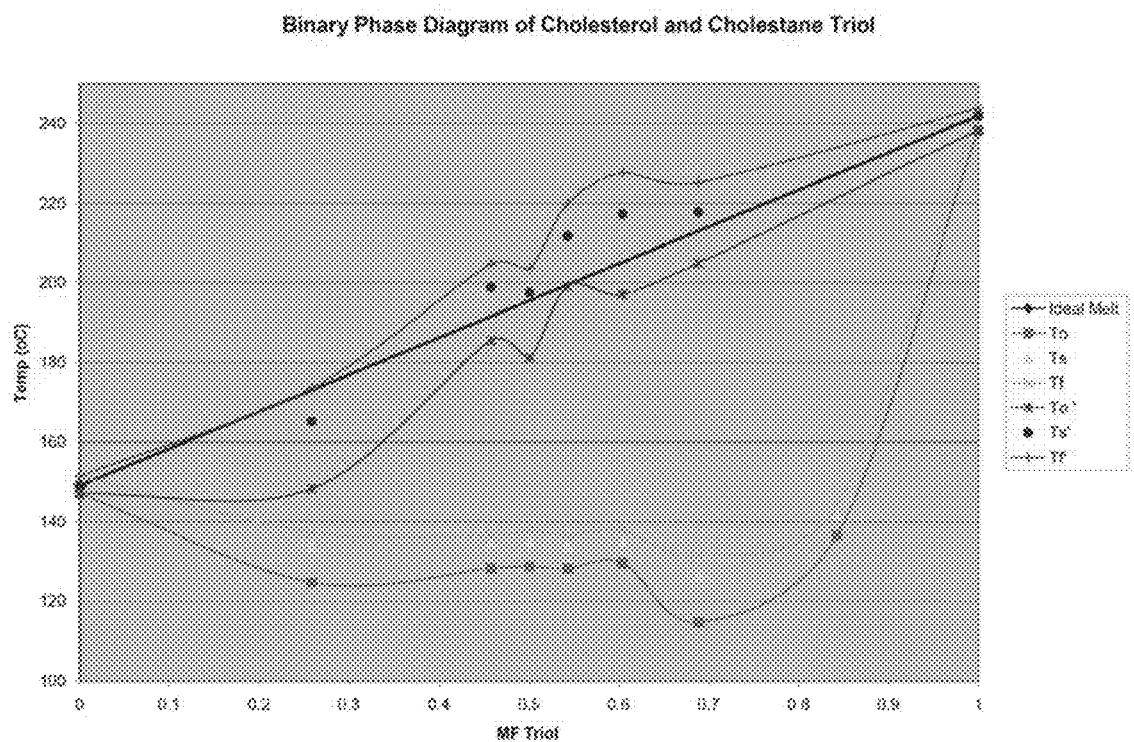
FIG. 8B is an expanded graph view of Cholesterol and Cholestane Triol.

The phase diagrams of FIGS. 8A and 8B show that the binary system of CT and cholesterol are not co-soluble with each other, since there are two distinct melting points for each MF of CT. As the phase diagrams in FIGS. 8A and 8B show, maximum separation in melting points of the individual components are reached around 0.4-0.7 MF of CT. This means that once the first component of the binary system melts, there is a creation of a solid—liquid phase on the diagram. This phase exists until the ending temperature of the second peak is reached. After that point, both components in the binary system in the liquid form, but do not tend to aggregate together.

Figure 9A:
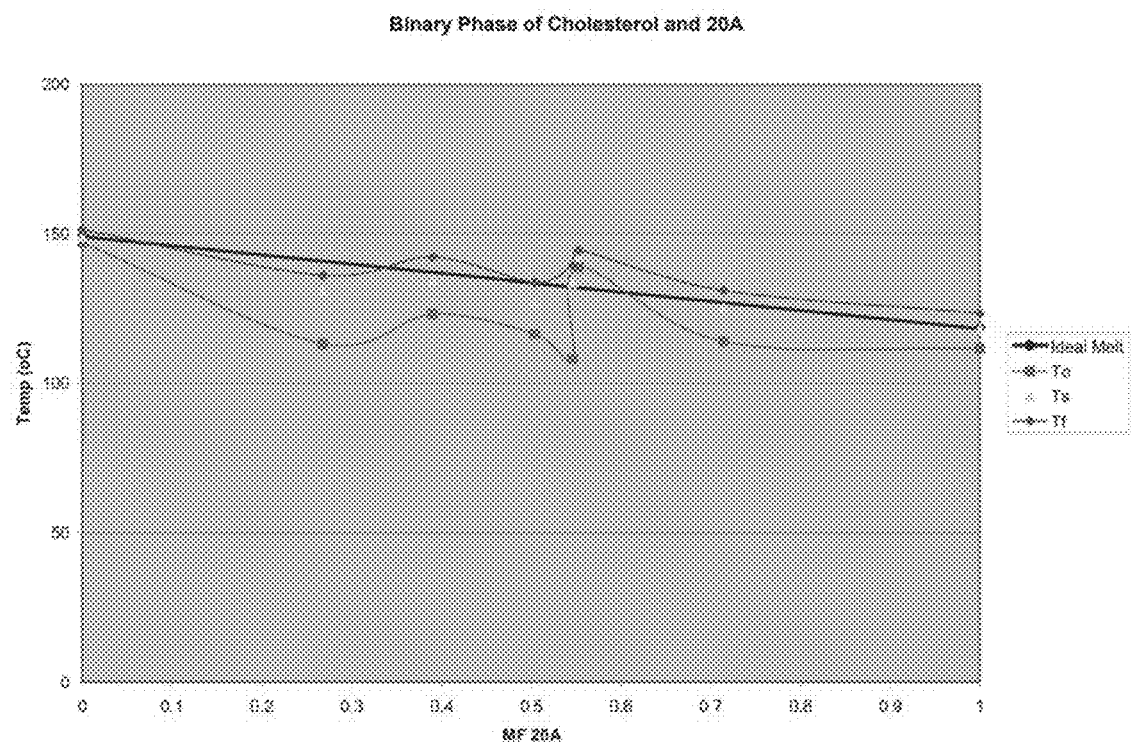
FIG. 9A is a graph of the binary combinations of Cholesterol and 20-Alpha.
Figure 9B:
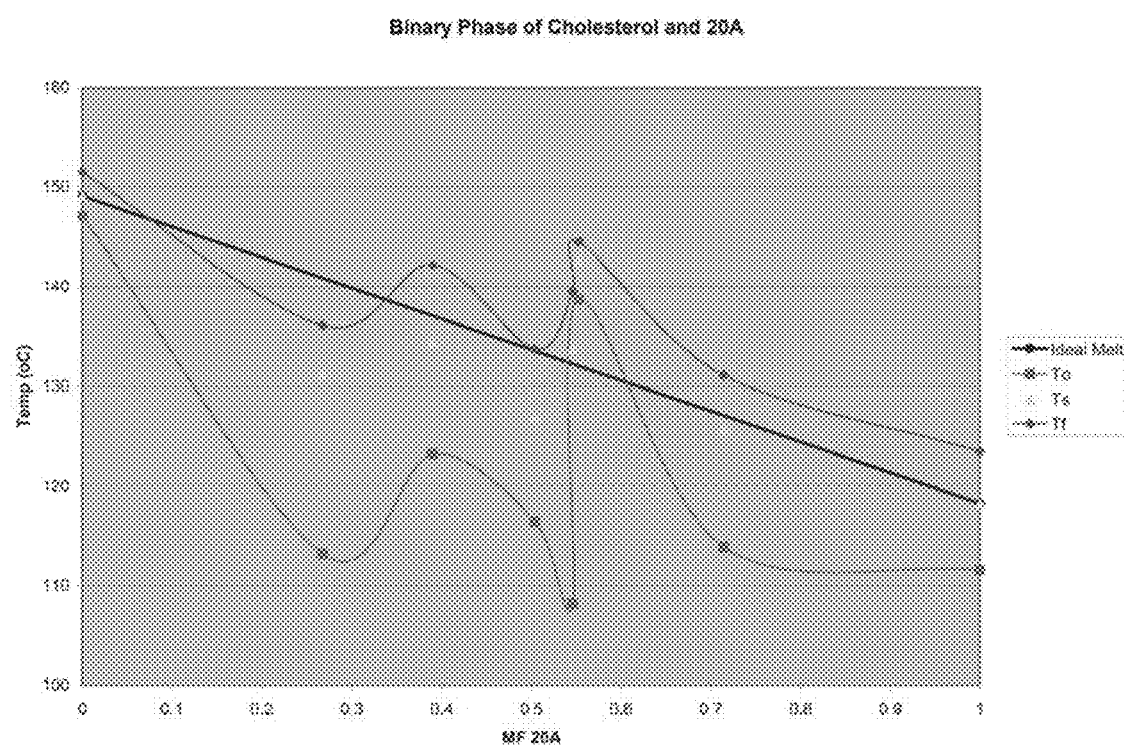
FIG. 9B is an expanded graph view of Cholesterol and 20-Alpha.

FIGS. 9A and 9B show that the phase diagrams for cholesterol and 20A produce results that have minimal deviations from the ideal melt line, which is unlike previous results shown so far for the other binary systems. The figures indicate that around 0.5-0.6 MF of 20A a dramatic change occurs in the melting of the packed crystal structures. This can be seen by the sharp transition between two close mole fractions of 20A in different systems.

Figure 10A:
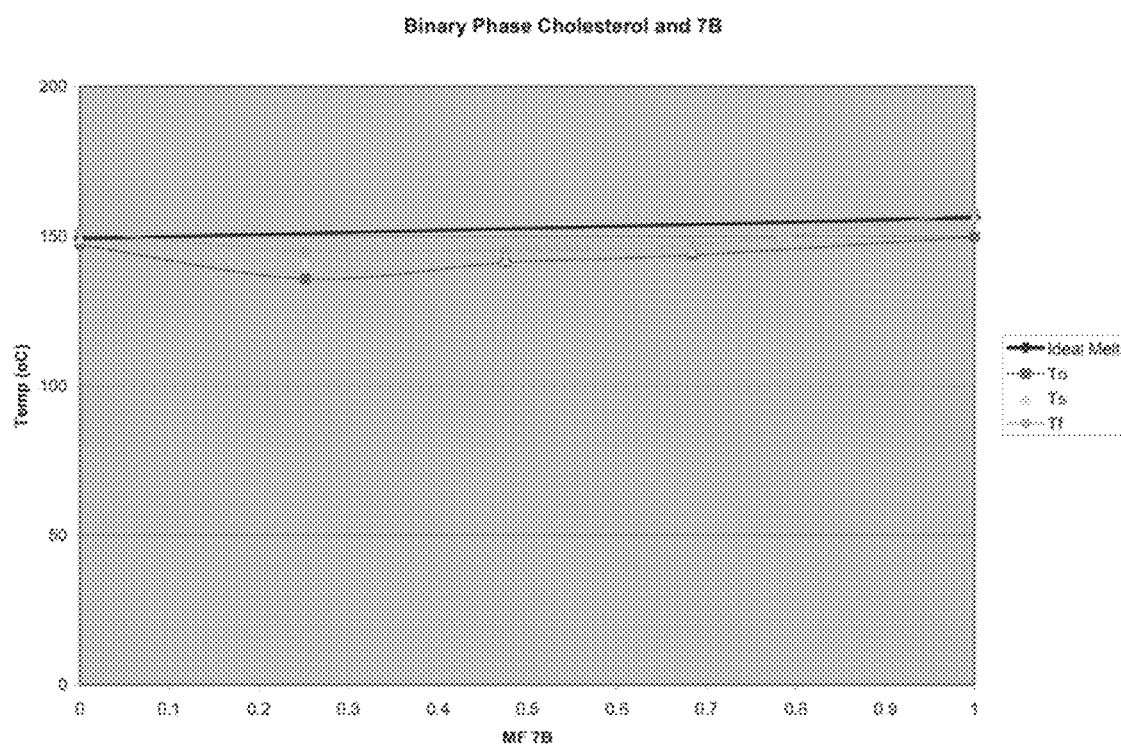
FIG. 10A is a graph of the binary combinations of Cholesterol with 7-Beta.
Figure 10B:
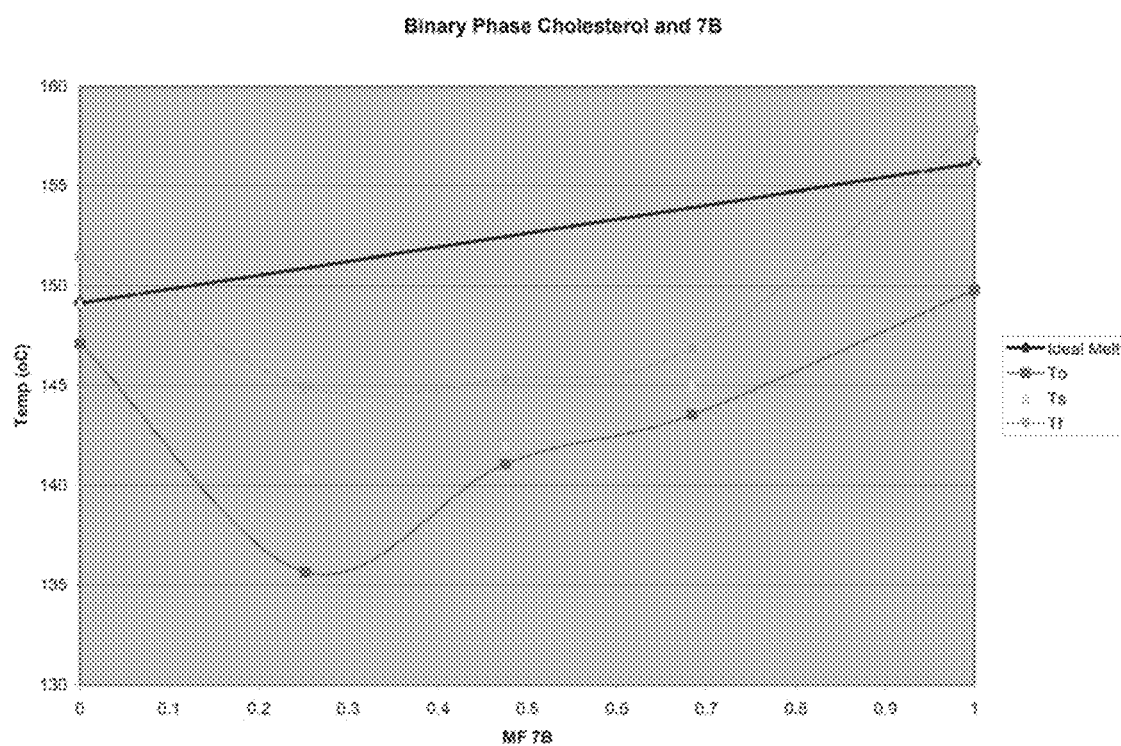
FIG. 10B is an expanded graph view of Cholesterol and 7-Beta.

FIGS. 10A and 10B show that overall concentrations of cholesterol and 7B the binary system is co-soluble, as indicated by the phase diagrams. FIGS. 10A and 10B indicate that between 0.2-0.3 MF of 7B an inflection point occurs and the solidus line starts to come closer to the ideal melt line. The maximum deviation between the onset, peak, and ending temperatures for this system also occurs around this range too.

Figure 11A:
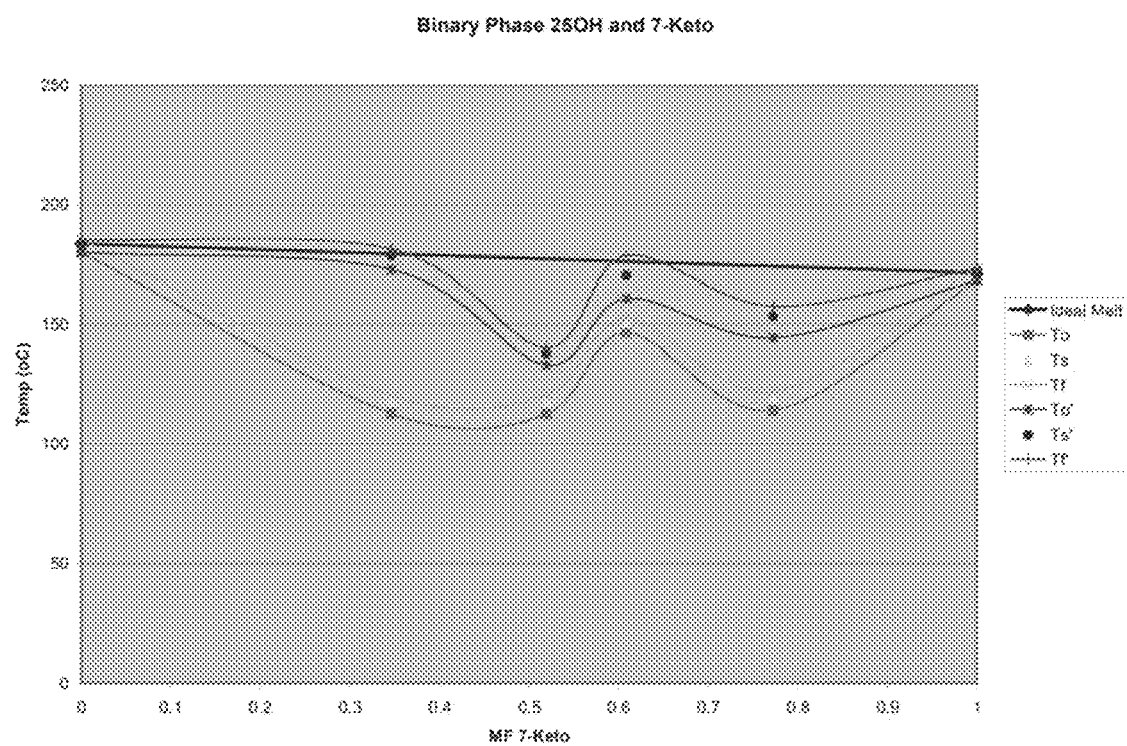
FIG. 11A is a graph of the binary combinations of 25-OH with 7-Keto.
Figure 11B:
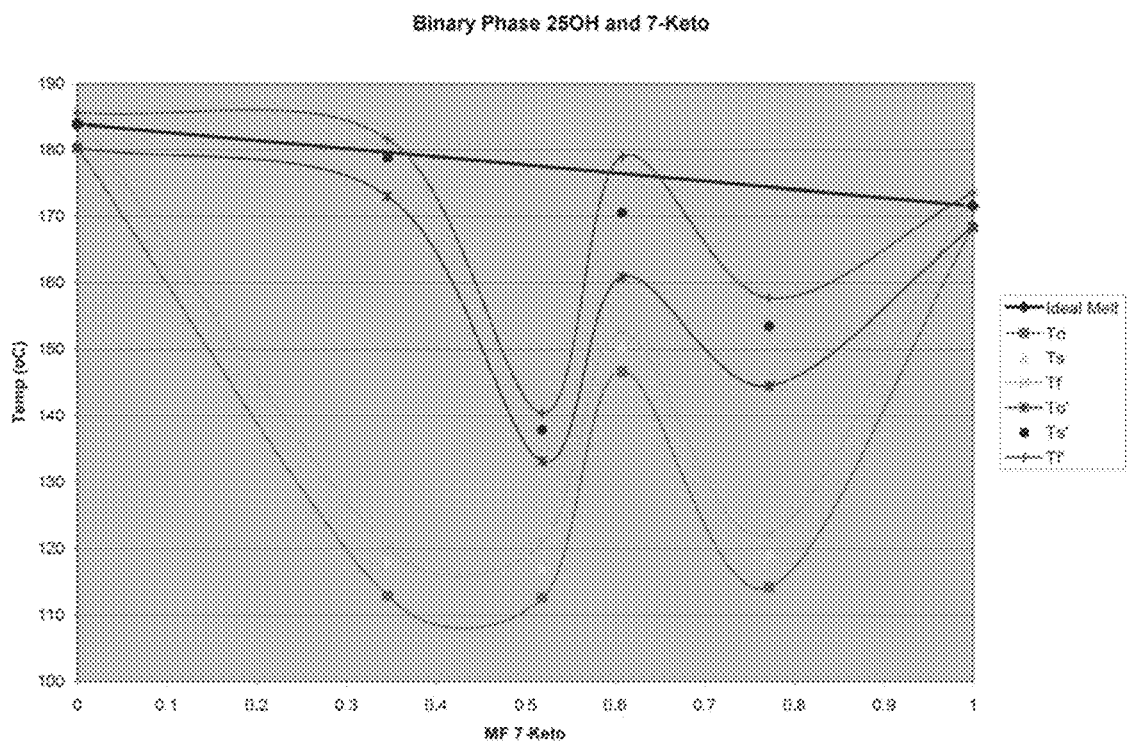
FIG. 11B is an expanded graph view of 25-OH and 7-Keto.

FIGS. 11A and 11B show that the binary systems that contain 7-Keto and 25OH are not co-soluble with each other, as can be seen by the two separate sets of data points on the phase diagrams. The graphs also indicate that there is a packed structure in the range of about 0.5-0.8 MF of 7-Keto requiring more energy than other MF on either side of it to melt the crystal. This indicates that the structure is most stable in combinations around 0.5-0.8 MF of 7-Keto, whereas the structures are less stable in other MF because they require less energy to start the transition from solid to the solid-liquid state. Also, the difference between $T_f$ and $T_o$ is at a minimum in this range.

Figure 12A:
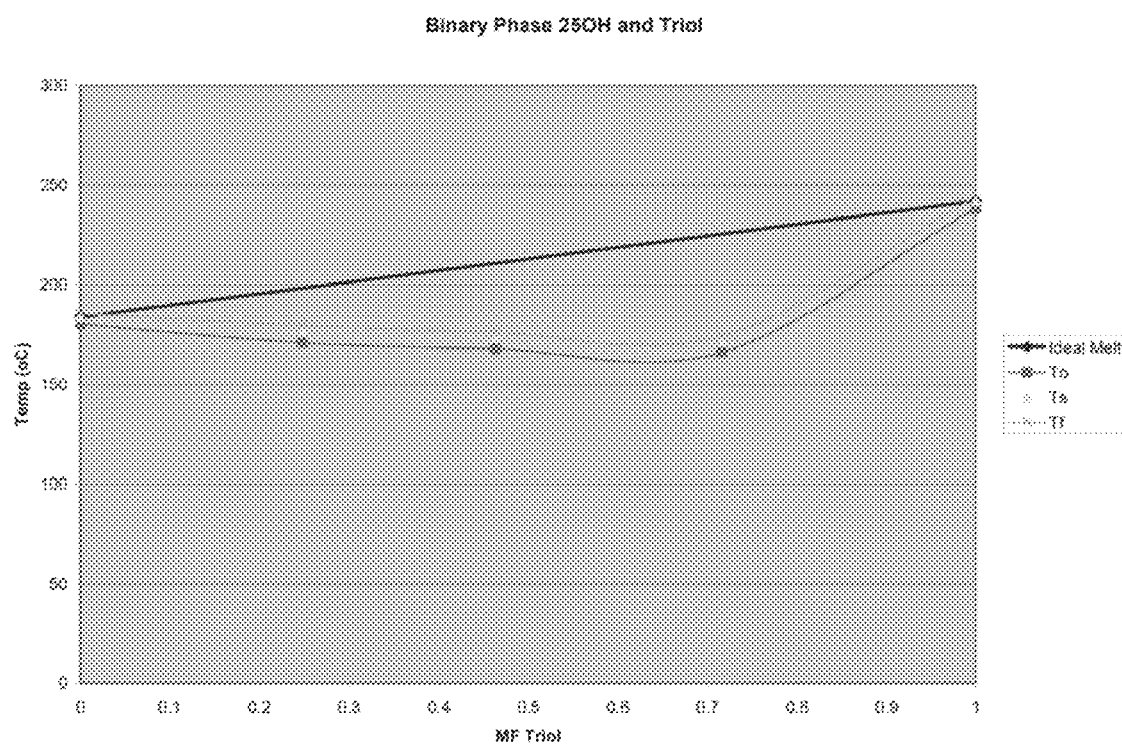
FIG. 12A is a graph of the binary combinations of 25-OH with Cholestane Triol.
Figure 12B:
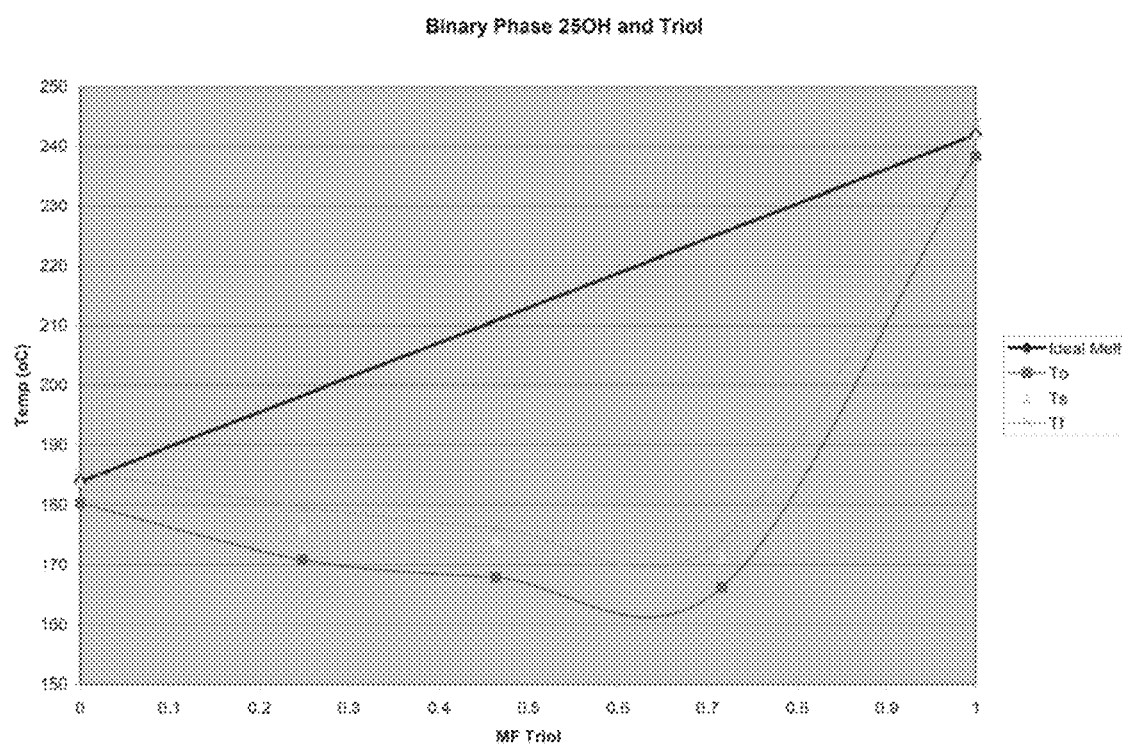
FIG. 12B is an expanded graph view of 25-OH and Cholestane Triol.

FIGS. 12A and 12B show that the binary system of 25OH and CT is co-soluble over the entire concentration range of MF for CT. The solidus line slowly decreases until about 0.6-0.7 MF of CT before starting a sharp increase to the melting point of CT. The maximum deviation from the ideal melt line occurs around the inflection point of 0.6-0.7 MF of CT.

Figure 13A:
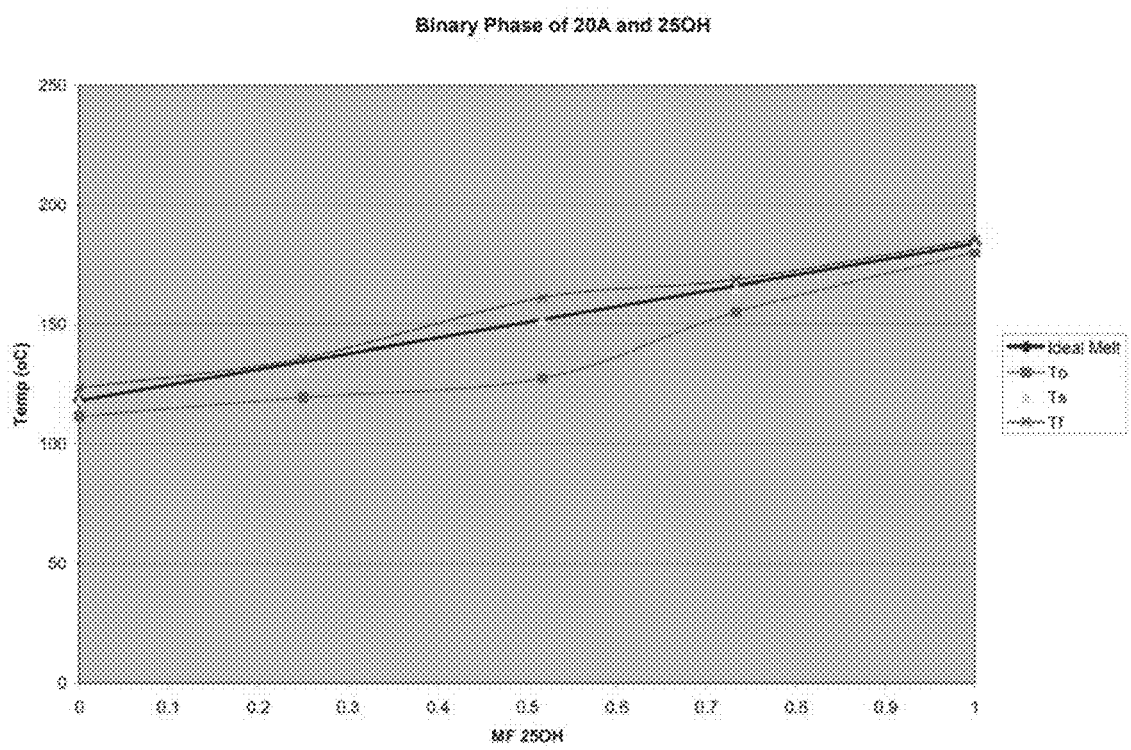
FIG. 13A is a graph of the binary combinations of 25-OH with 20-Alpha.
Figure 13B:
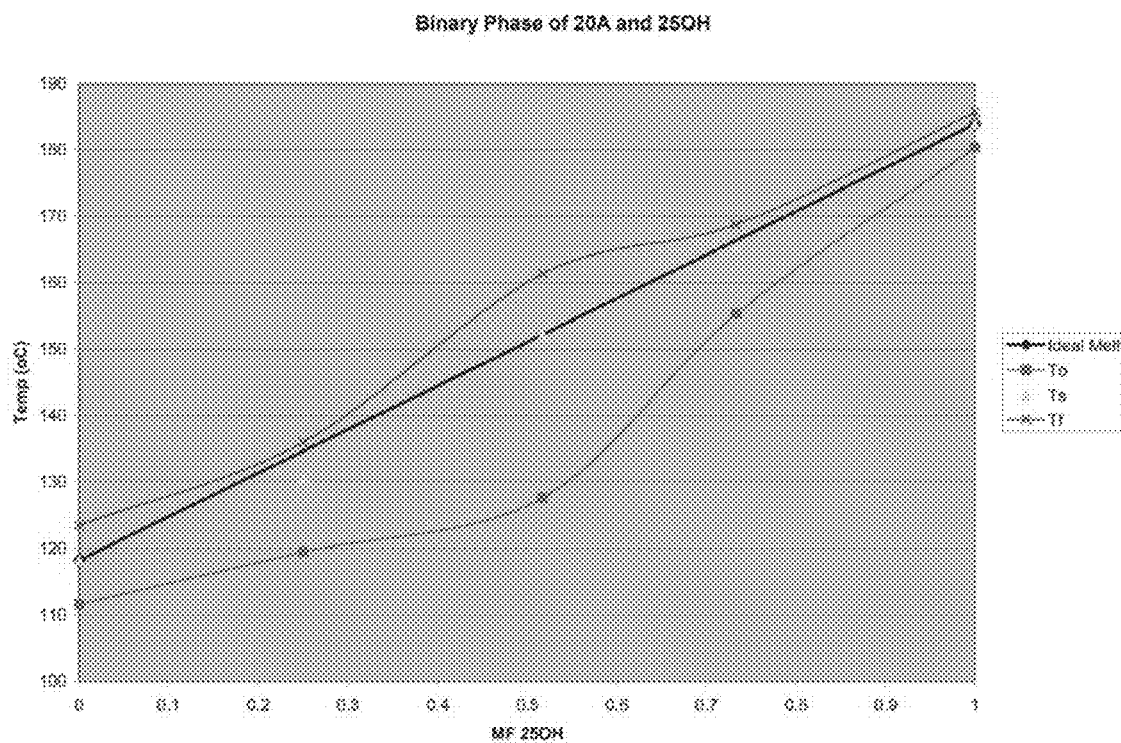
FIG. 13B is an expanded graph view of 25-OH and 20-Alpha.

The phase diagrams of FIGS. 13A and 13B illustrate that the binary system of 20A and 25OH is co-soluble over all concentrations. Also, the results show that the $T_s$ points lie almost directly on top of the ideal melt line. Thus, the experimental and the theoretical results are in agreement since the peak temperatures of the binary combinations lie on top of the ideal melt line. The maximum deviation between the temperatures of the melts occurs around 0.5 MF of 25OH, where the points are spread out the most between the onset, peak, and final temperatures.

Figure 14A:
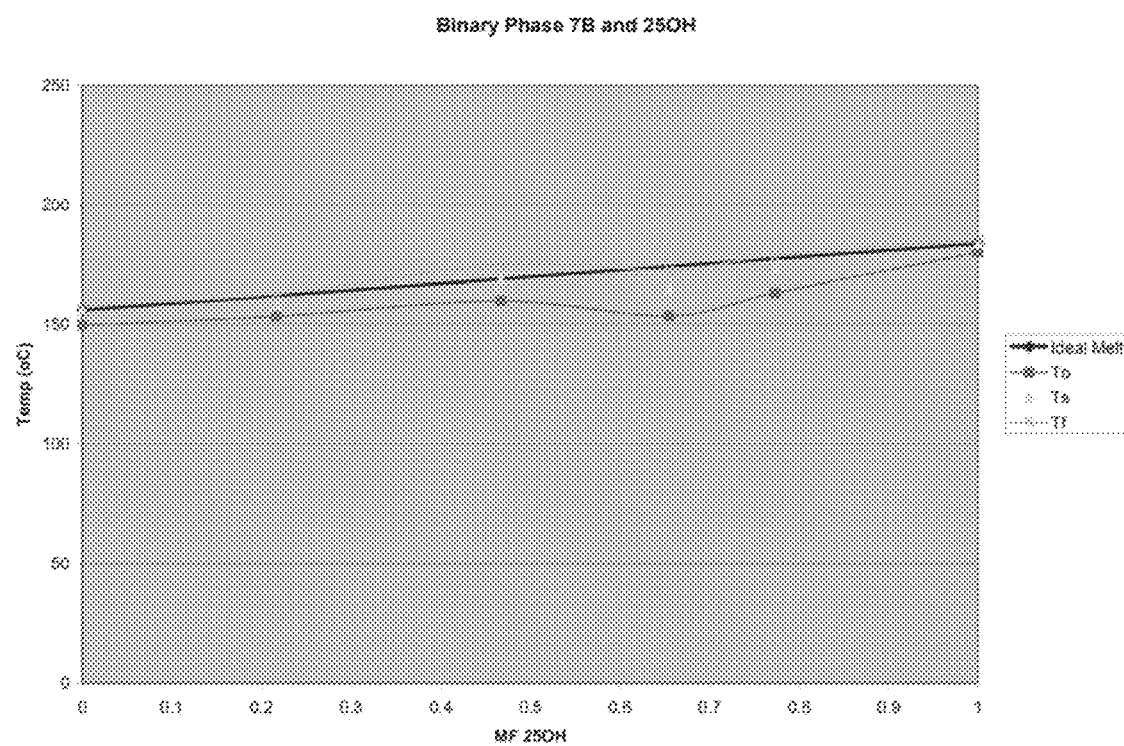
FIG. 14A is a graph of the binary combinations of 25-OH with 7-Beta.
Figure 14B:
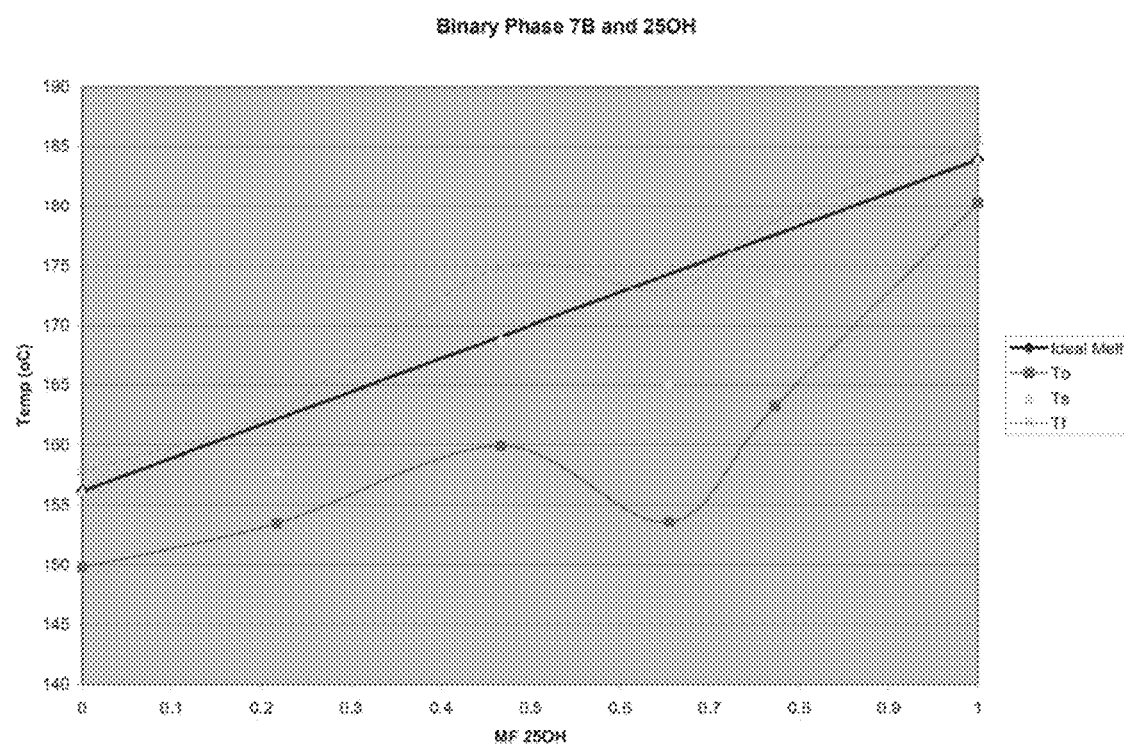
FIG. 14B is an expanded graph view of 25-OH and 7-Beta.

The phase diagrams for FIGS. 14A and 14B illustrate that the solidus and liquidus lines parallel the ideal melt line up to about 0.5 MF of 25OH before decreasing until about 0.7 MF of 25OH and then increasing again. The binary system is co-soluble over all concentrations.

Figure 15A:
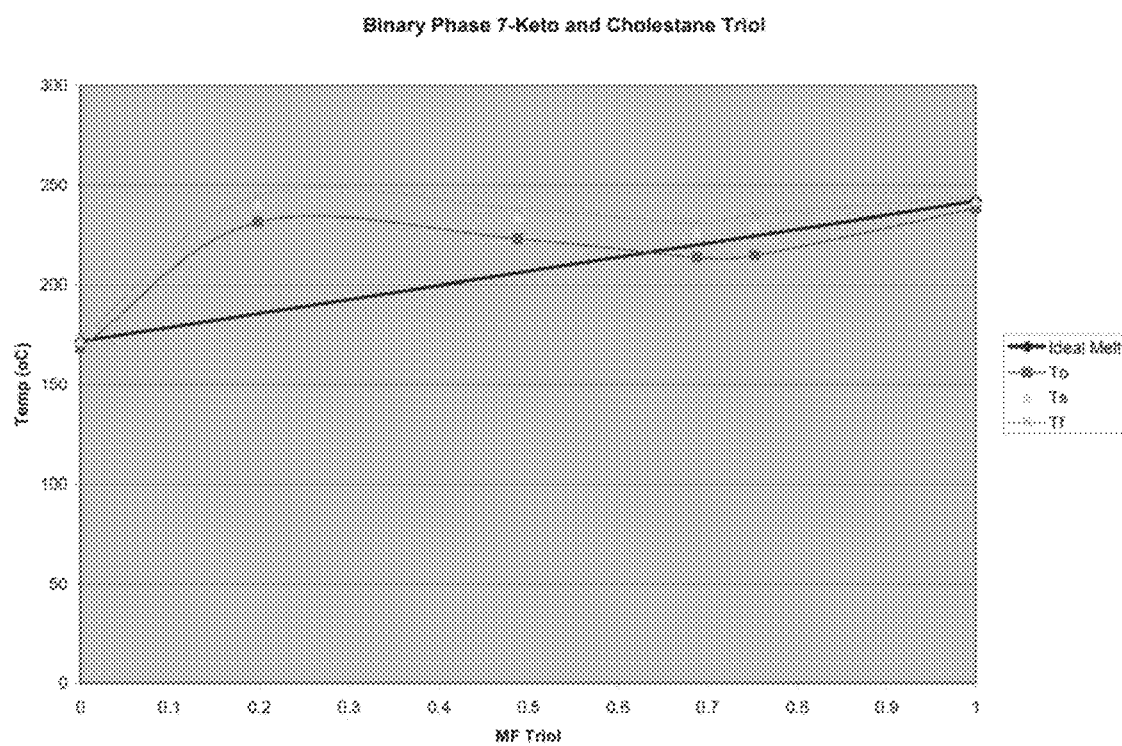
FIG. 15A is a graph of the binary combinations of Cholestane Triol with 7-Keto.
Figure 15B:
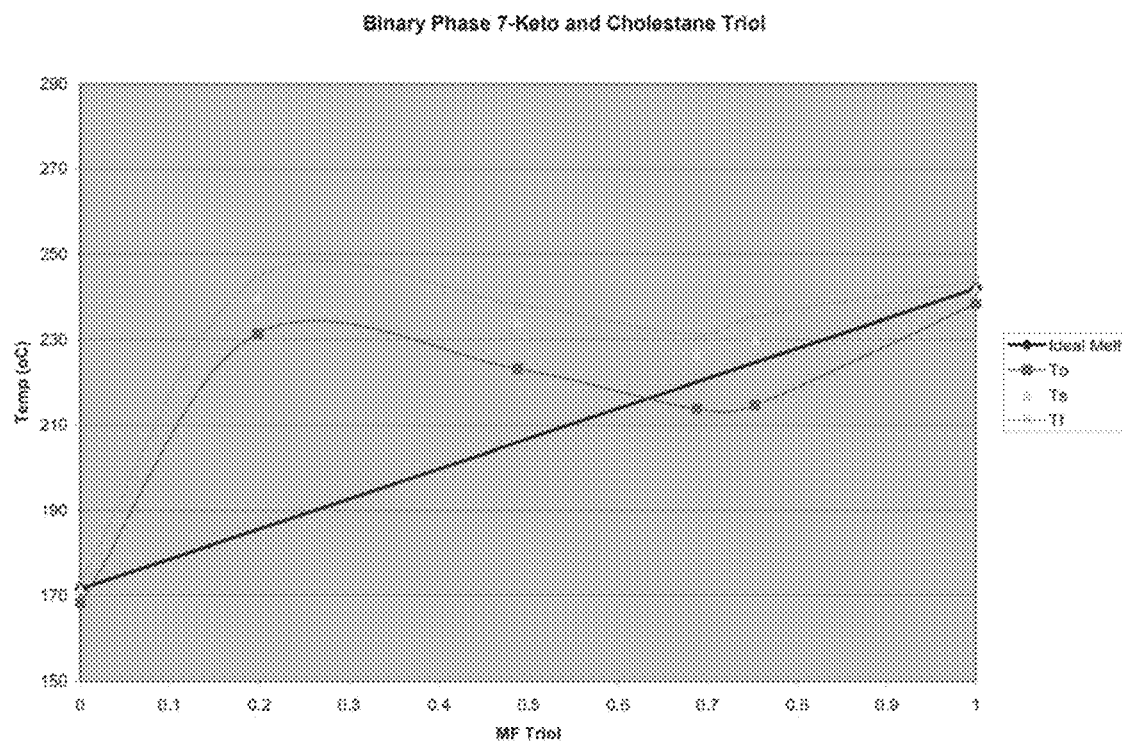
FIG. 15B is an expanded graph view of Cholestane Triol and 7-Keto

FIGS. 15A and 15B illustrate that over all concentrations of the 7-Keto and CT the binary system is co-soluble. What had not been seen n the previous phase diagrams is that there exists a positive deviation from the ideal melt line as is indicated by the solidus, liquidus, and peak temperatures of the different mole fractions being above this line at low concentrations of CT. Thus, even though there are low concentrations of CT in the binary systems, the CT still is the dominant factor in determining the melting point of the packed crystal structure.

Figure 16A:
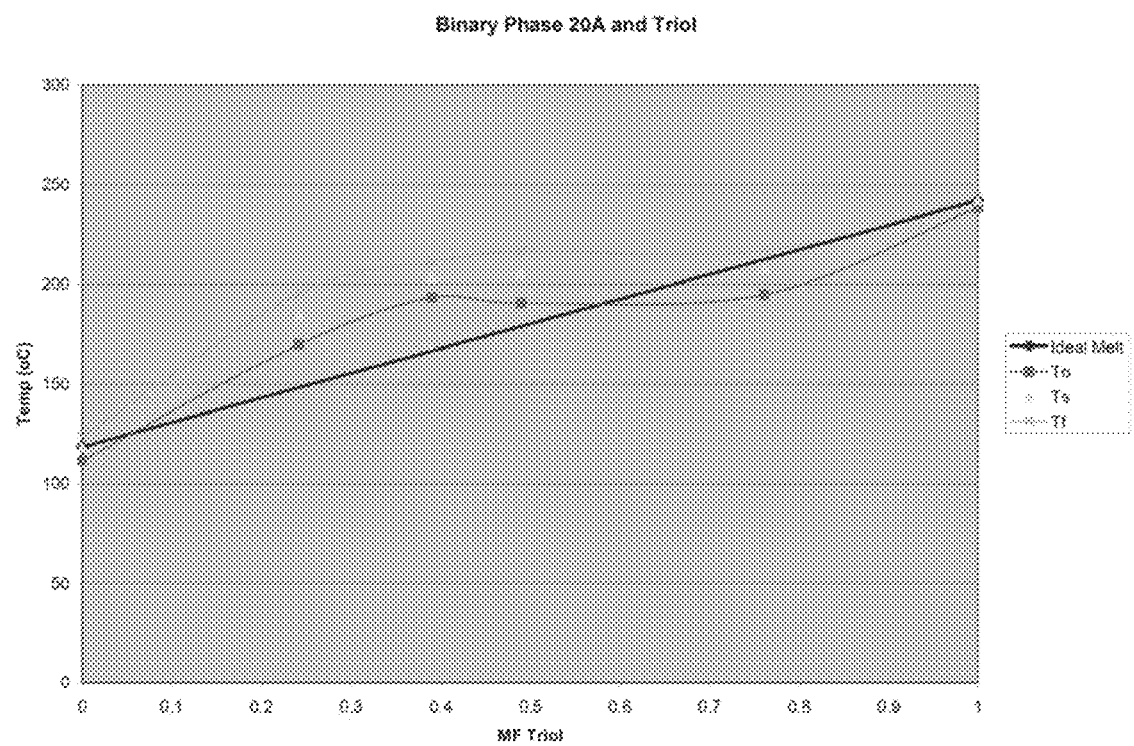
FIG. 16A is a graph of the binary combinations of Cholestane Triol with 20-Alpha.
Figure 16B:
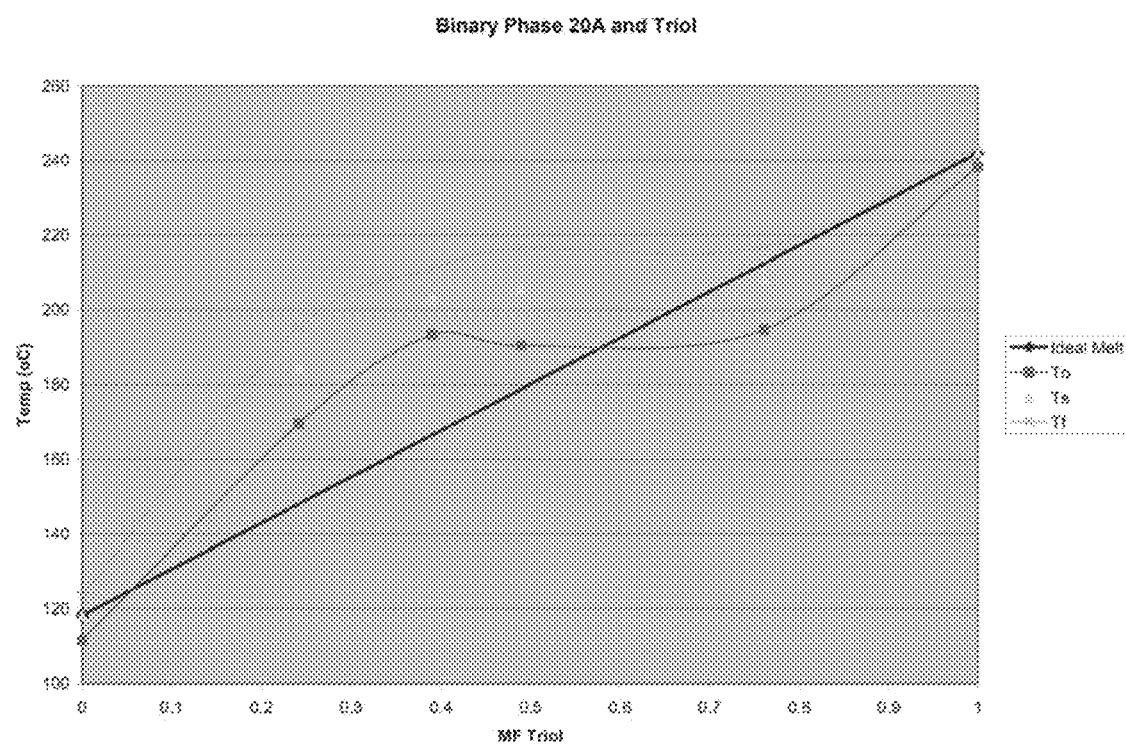
FIG. 16B is an expanded graph view of Cholestane Triol and 20-Alpha.

The phase diagrams for FIGS. 16A and 16B also show that CT is co-soluble with 20A, and again there are positive deviations from the ideal melt line for the low concentrations of the CT. The solidus and liquidus lines return below the ideal melt curve between the concentrations of 0.5-0.8 MF of CT, which predicts that there is a specific mole fraction that will coincide with a point on the ideal melt line for both the solidus and liquidus line.

Figure 17A:
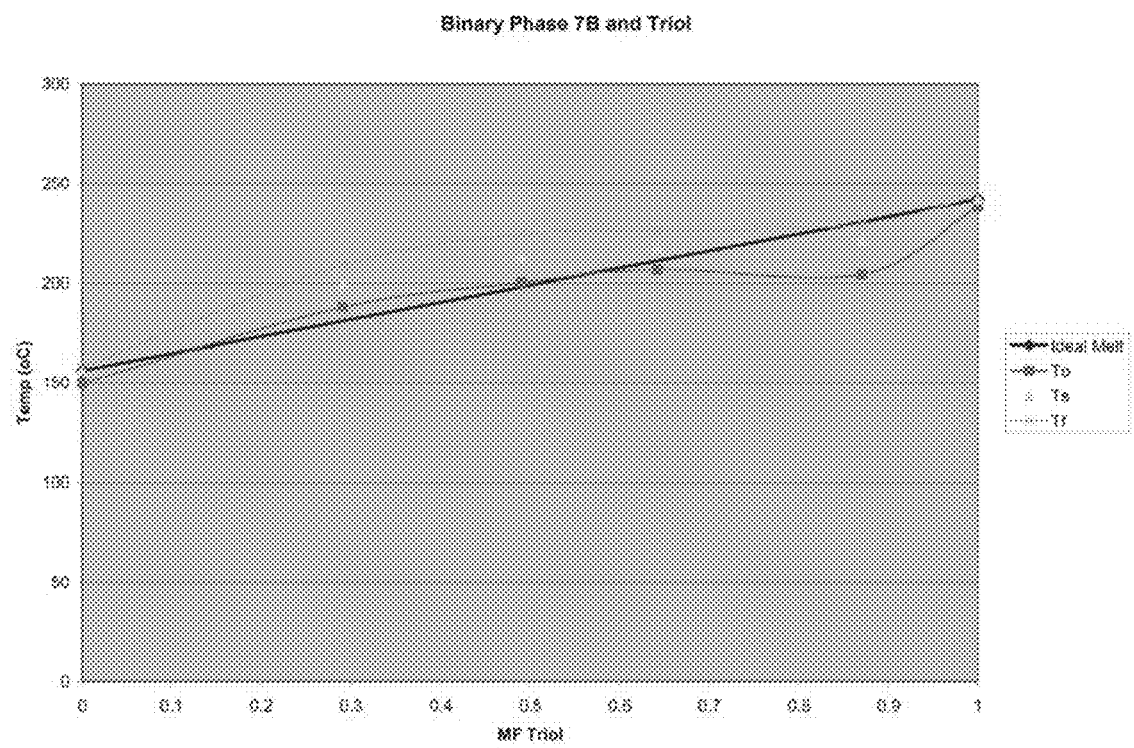
FIG. 17A is a graph of the binary combinations of Cholestane Triol with 7-Beta.
Figure 17B:
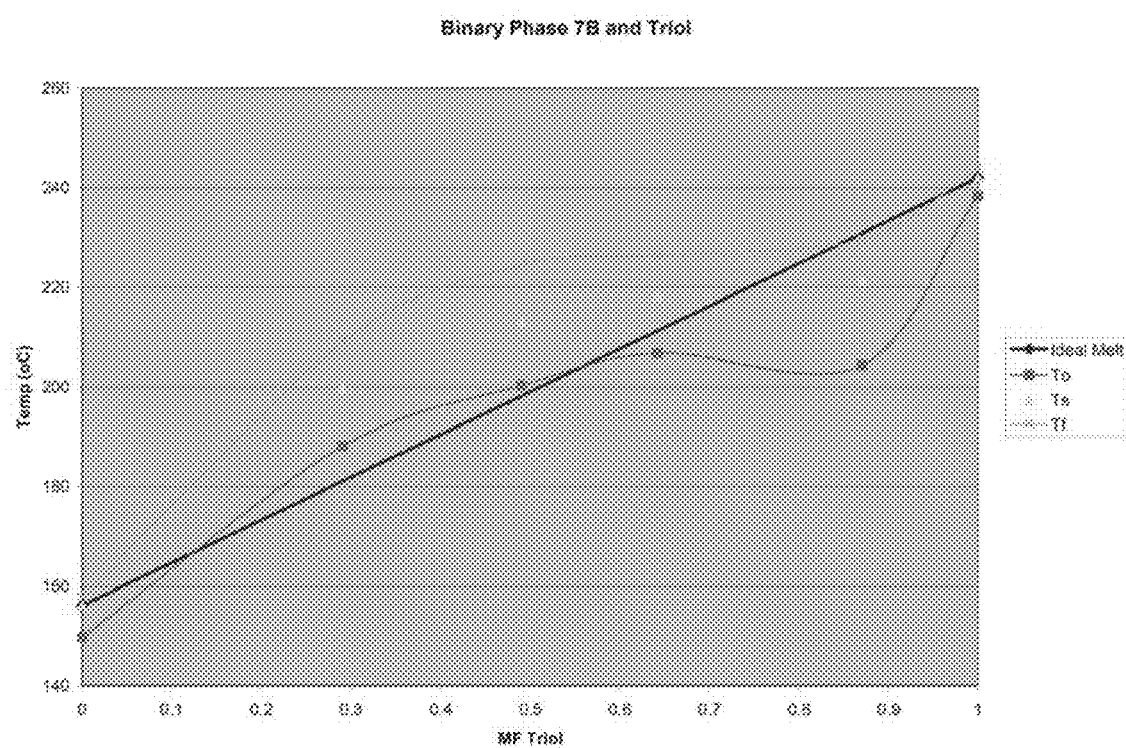
FIG. 17B is an expanded graph view of Cholestane Triol and 7-Beta.

The phase diagrams for CT and 7B in FIGS. 17A and 17B demonstrate a positive deviation from the ideal melt line. The expanded view of FIG. 17A shows that the results are close to the theoretical results that were predicted by the ideal melt line. From this, the CT seems to be affected less in its packing structure than possibly the other combinations, and could explain why the positive deviations to the ideal melt line occur.

Figure 18A:
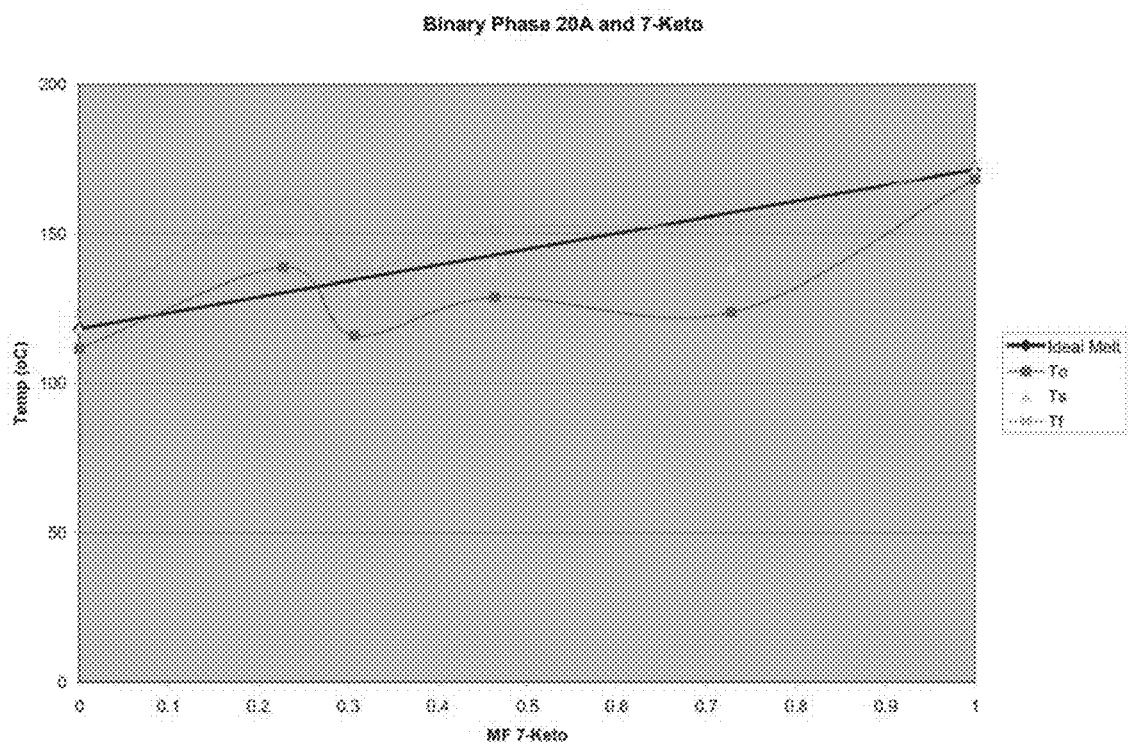
FIG. 18A is a graph of the binary combinations of 7-Keto with 20-Alpha.
Figure 18B:
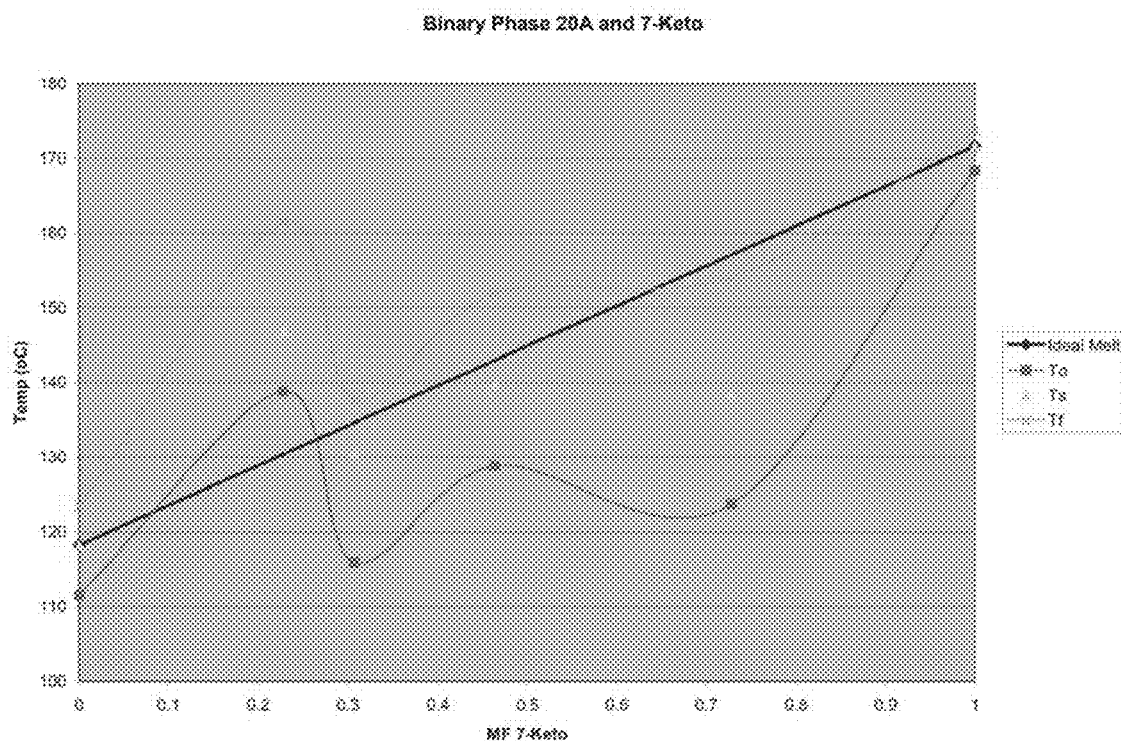
FIG. 18B is an expanded graph view of 7-Keto and 20-Alpha.

The graphs for FIGS. 18A and 18B show that as a general trend, the data follows the ideal melt line. While over all mole fractions for 7-Keto and 20A they, are co-soluble, the data does not produce clean results. As FIG. 18B shows, the solidus and liquidus lines oscillate between increasing and decreasing in energy required to melt the packed crystal structures. The low concentrations of the 7-Keto region are where the most erratic results can be seen.

Figure 19A:
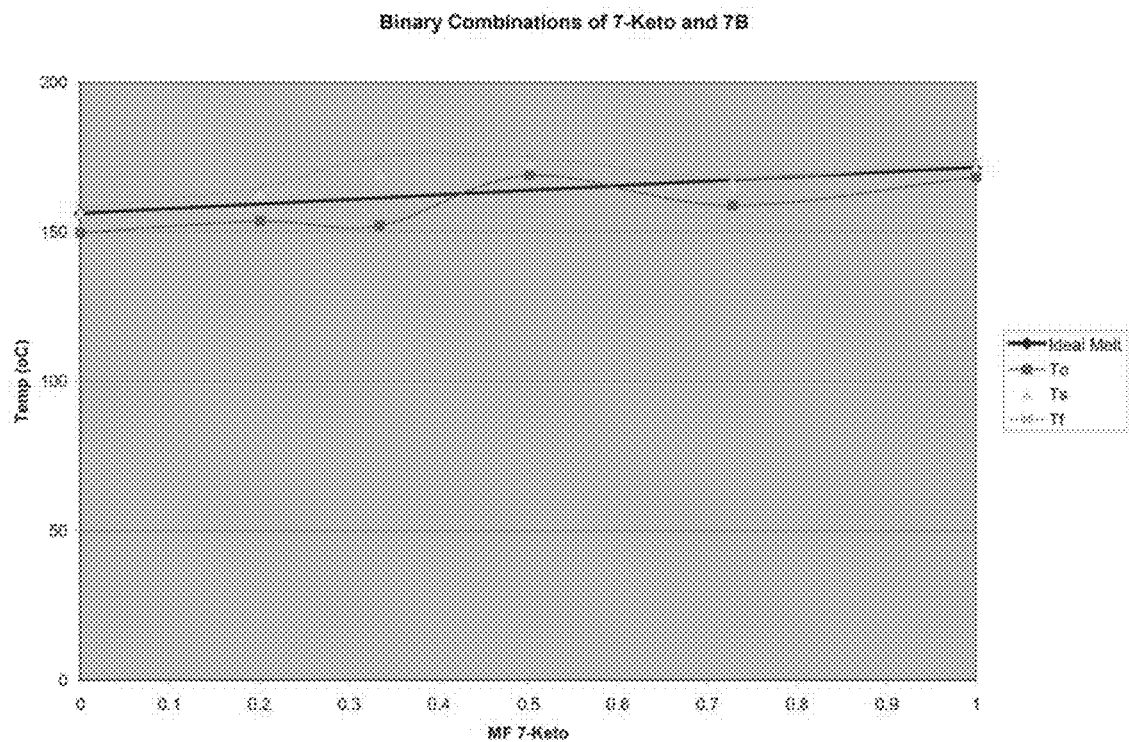
FIG. 19A is a graph of the binary combinations of 7-Keto with 7-Beta.
Figure 19B:
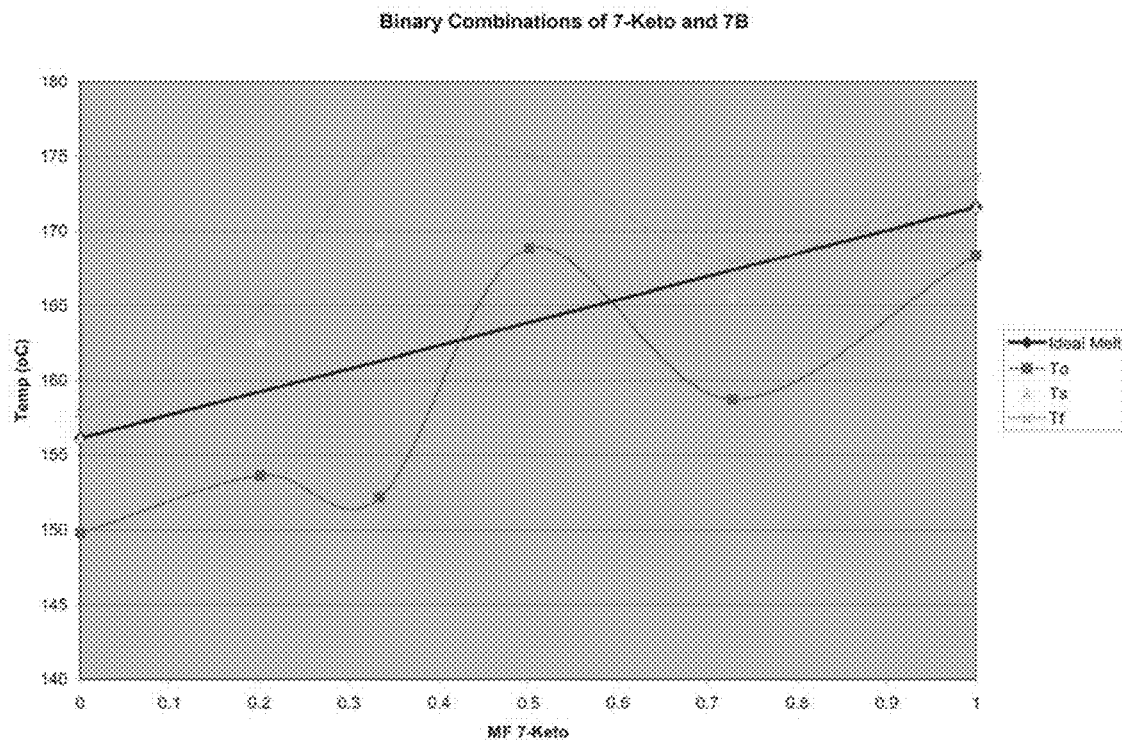
FIG. 19B is an expanded graph view of 7-Keto and 7-Beta.

Binary phase diagrams in FIGS. 19A and 19B illustrate the relationship between 7-Keto and 7B as being co-soluble over all MF concentrations. These diagrams also reveal that around a 0.5 MF of 7-Keto the solidus line has a disruption from the general trend which shows a data point above the ideal melt line. This data point being, located above the ideal melt line is in error, but is, acceptable since it is probably within an error bar of the real data point.

Figure 20A:
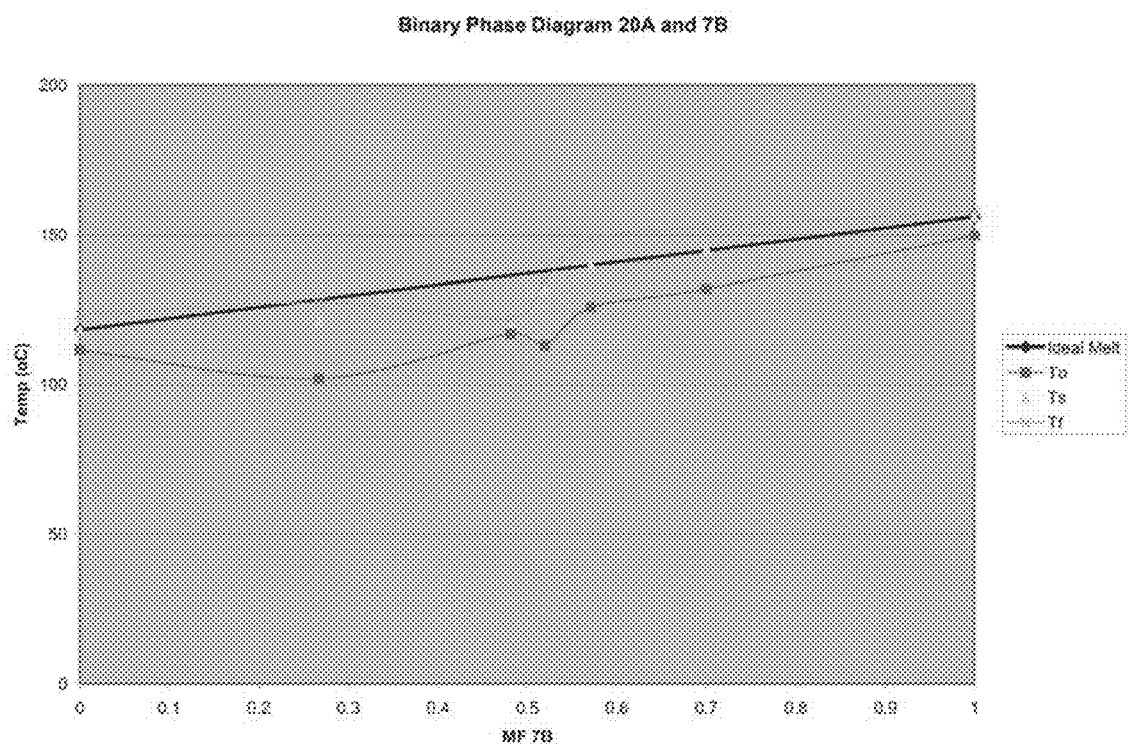
FIG. 20A is a graph of the binary combinations of 20-Alpha with 7-Beta.
Figure 20B:
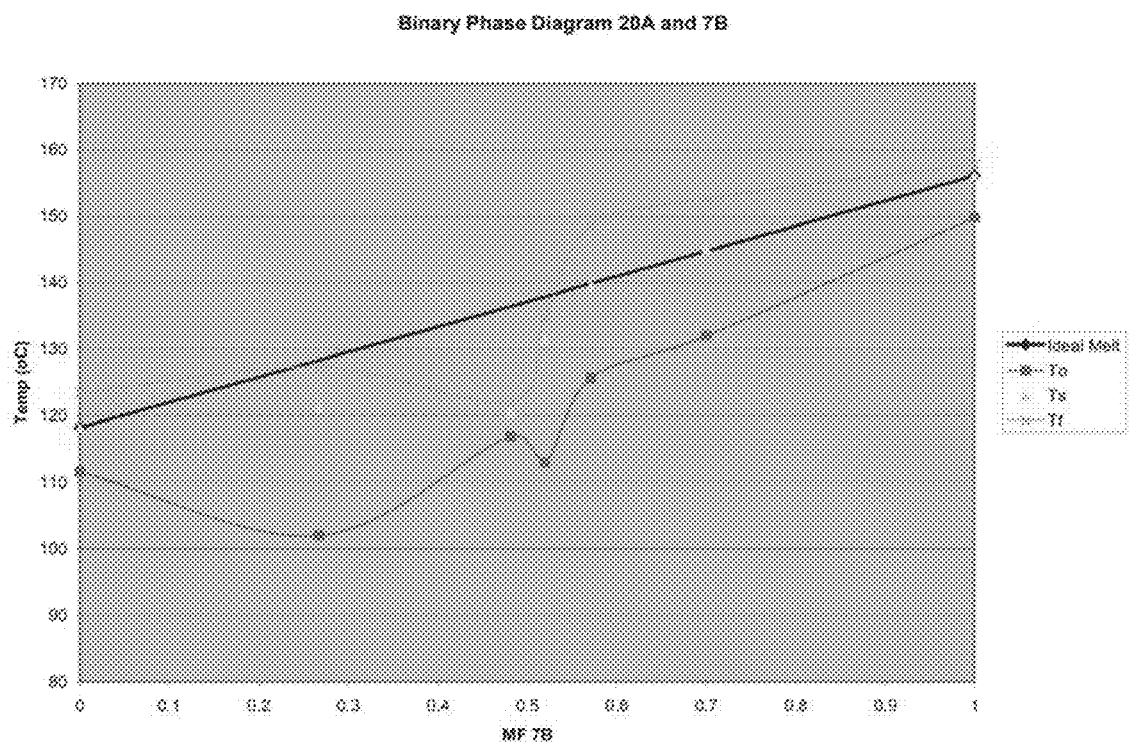
FIG. 20B is an expanded graph view of 20-Alpha and 7-Beta.

For the phase diagrams in FIGS. 20A and 20B, the binary system of 20A and 7B are co-soluble with each other. The phase diagram shows that at about 0.5 MF of 7B, a deviation from the general trend of the solidus line occurs. This point is lower in energy than the points directly next to it on either side. After this point, the energy required to melt the packed crystal structure increases again.

The results obtained from the phase diagrams show several characteristics of the system. The phase diagrams show if the components of the system are co-soluble with each other. Also, the diagrams show how well the experimental results align with the theoretical results. Finally, deviations from the ideal line illustrate how thermodynamically stable a system is.

The results for the different systems can also be used as predictors of what might happen if different oxidized cholesterol, which has not been studied yet, were combined with ones that have been. The phase diagrams show the relationship between mole fractions of the oxidized cholesterol and the co-solubility. From these diagrams, we can also determine the thermodynamic stability or instability of the binary systems. This data can then be used as a basis of an upside down pyramid scheme, where we build up from one component systems to two component systems stepwise until the top block is reached which is actual atherosclerotic plaque and its many components.

As previously mentioned, the phase diagrams can be either co-soluble or not co-soluble. For the phase diagrams that are co-soluble, the three possible results that can occur. There can be positive or negative deviations from the ideal, melt line, or the results can lie on top of the ideal melt line. The overall goal from this project was to predict how two oxidized cholesterol will interact with each other. Below, each oxidized sterol is compared with binary combinations to see if any similarities or differences may appear.

Examining the combinations of Cholesterol with 7B and with 20A, we observed that these binary combinations are also co-soluble with cholesterol. Looking at the structural differences between the 25OH, 7-Keto, 20A, and 7B compared to CT, it can be seen that there is a difference in the number of oxygens that they have. CT has two additional oxygens, which can effect the packing structure more so than the other oxidized cholesterol, since they only have one more oxygen atom in reference to cholesterol. This could be a possible explanation for why there are the differences in solubility of the oxidized cholesterol.

For the binary combinations of 7-Keto with CT, 20A, and 7B it is shown in the phase diagrams that 7-Keto was co-soluble with all of them. However, 7-Keto was not co-soluble with 25OH. The packing structures of 7-Keto and 25OH show that an interruption occurs by having the ketone on the steroid ring for the 7-Keto which is not on the 25OH molecule. Due to the interruption in the layering of the packed crystals, the two compounds will tend to associate only with molecules of themselves, causing them not to be co-soluble. However, this was not observed in the other binary combinations with 7-Keto, so there must be more to this than just the ketone group on the 7-Keto molecule.

Figure 63:
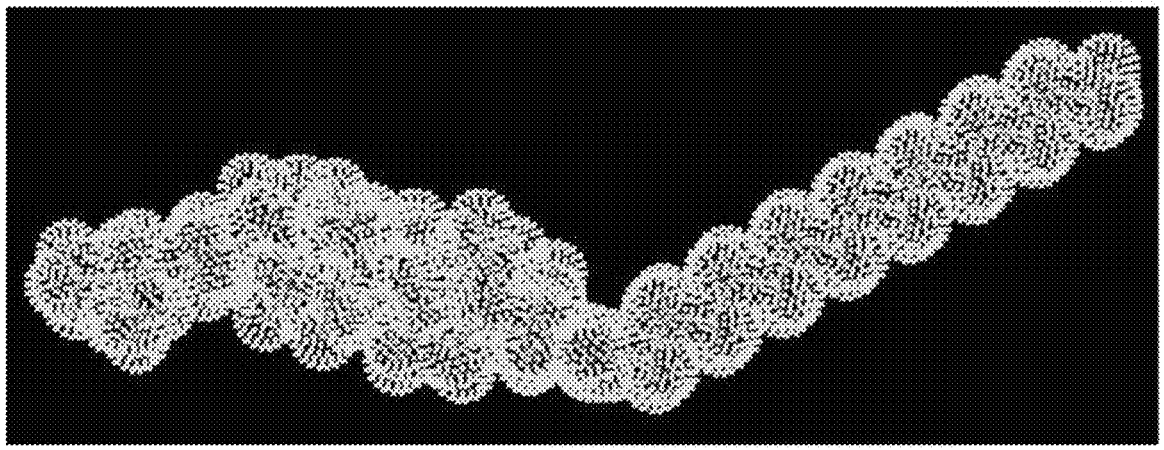
FIG. 63 is a dot surface model for Cholesteryl Palmitate.
Figure 64:
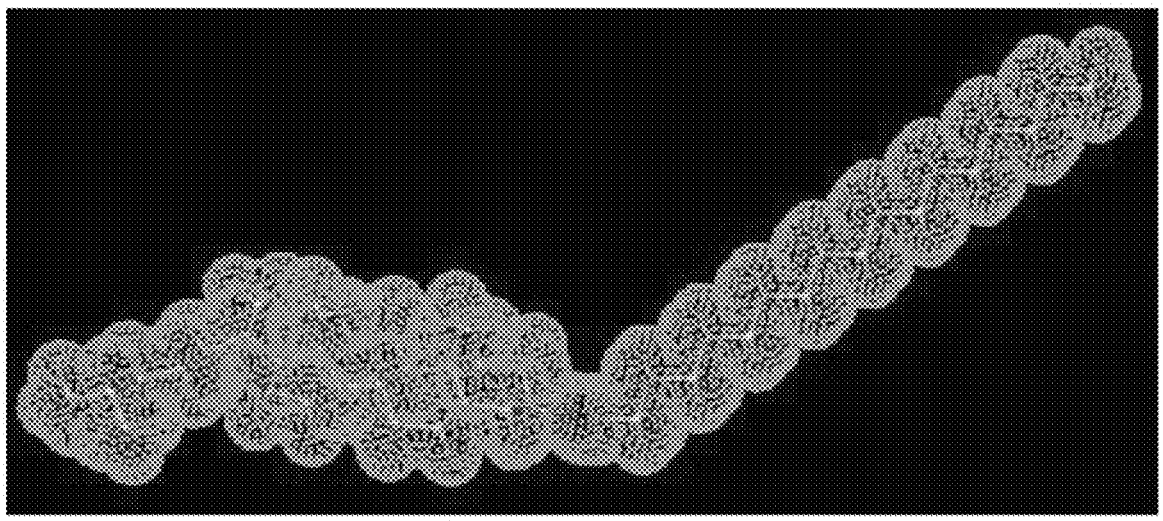
FIG. 64 is a dot surface model for Cholesteryl Stearate.
Figure 65:
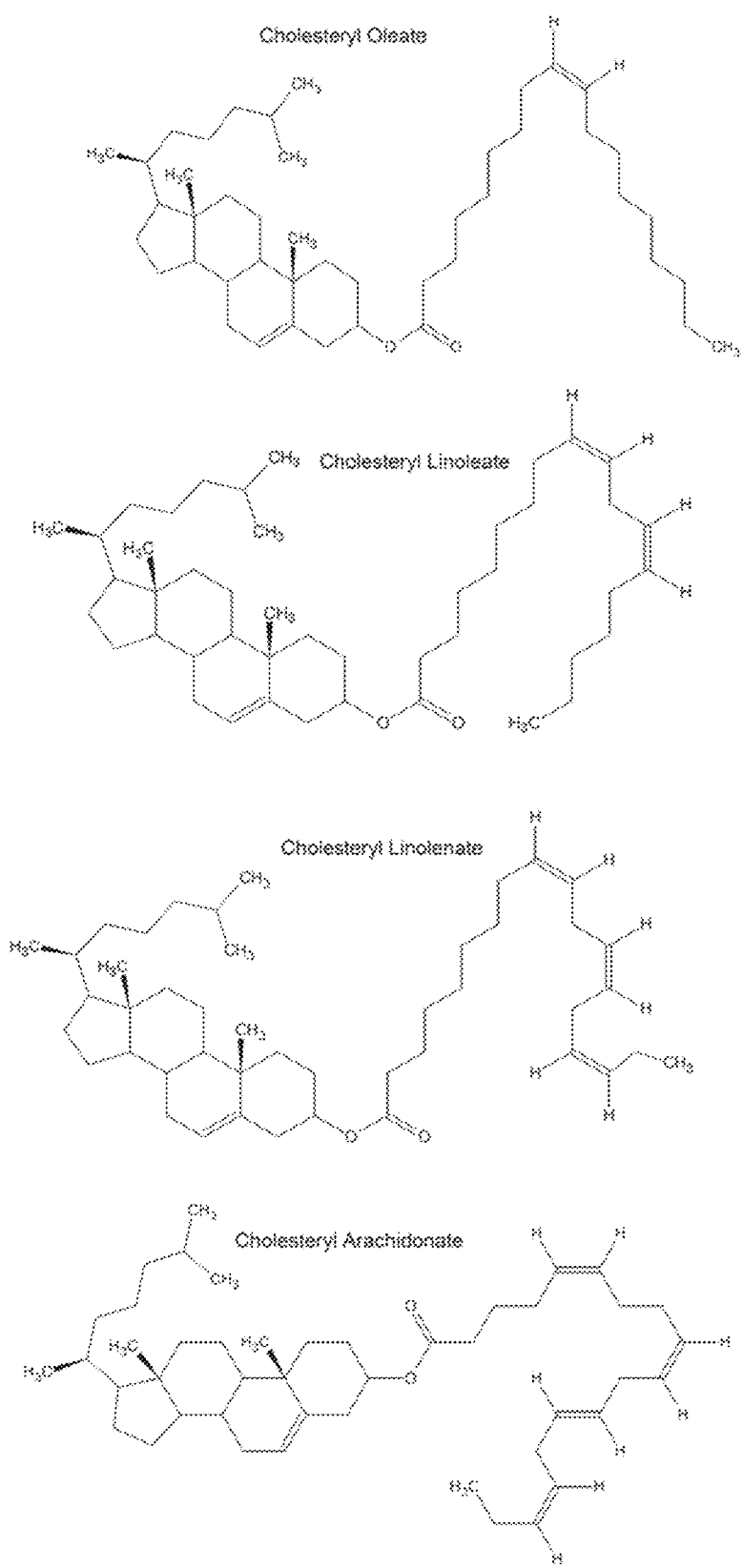
FIG. 65 shows line structures for Unsaturated Cholesteryl Esters Studied.
Figure 66:
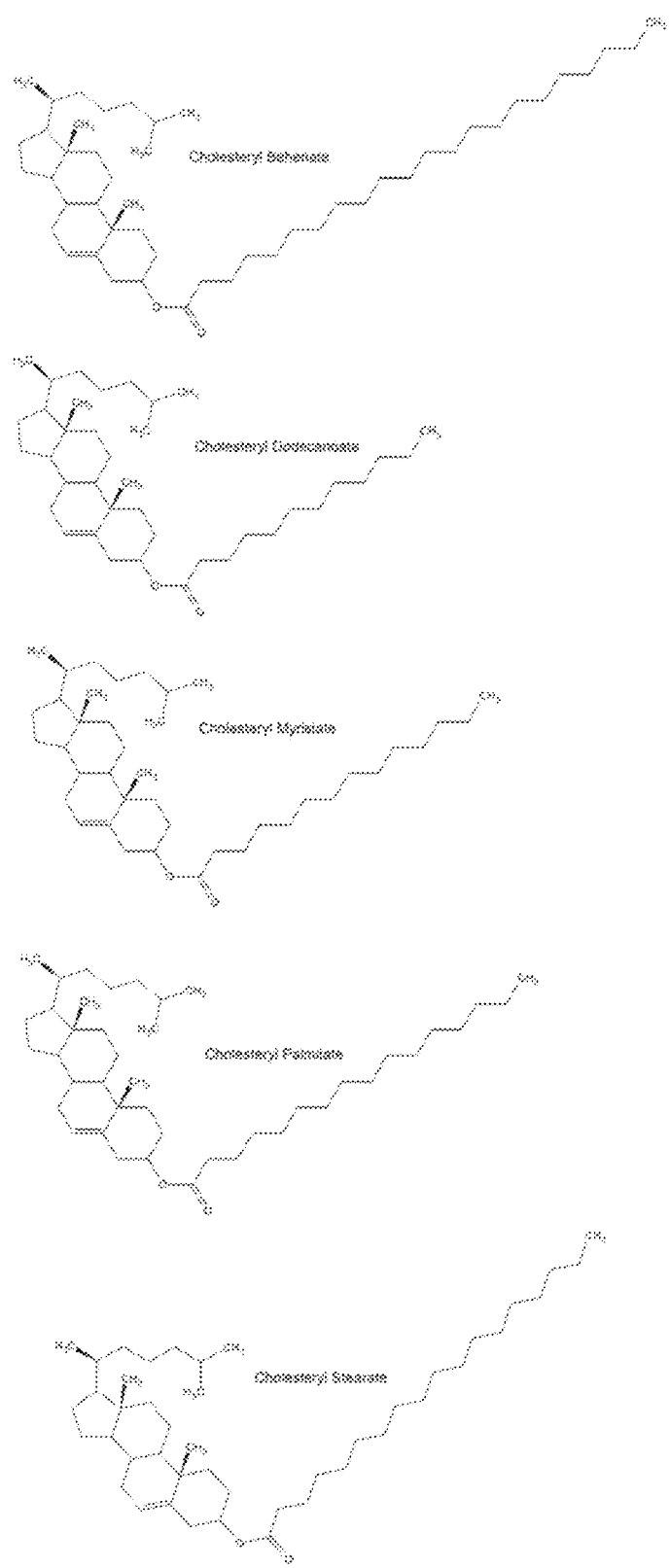
FIG. 66 shows line structures for Saturated Cholesteryl Esters Studied.
Figure 67:
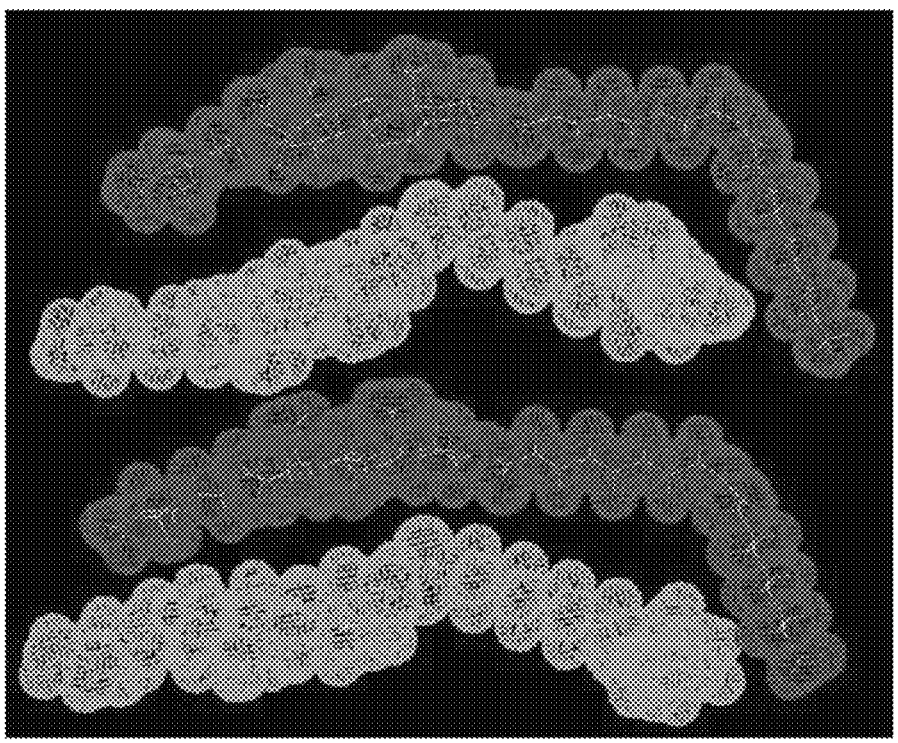
FIG. 67 shows the packing of Cholesteryl Oleate and Cholesteryl Linoleate.
Figure 68:
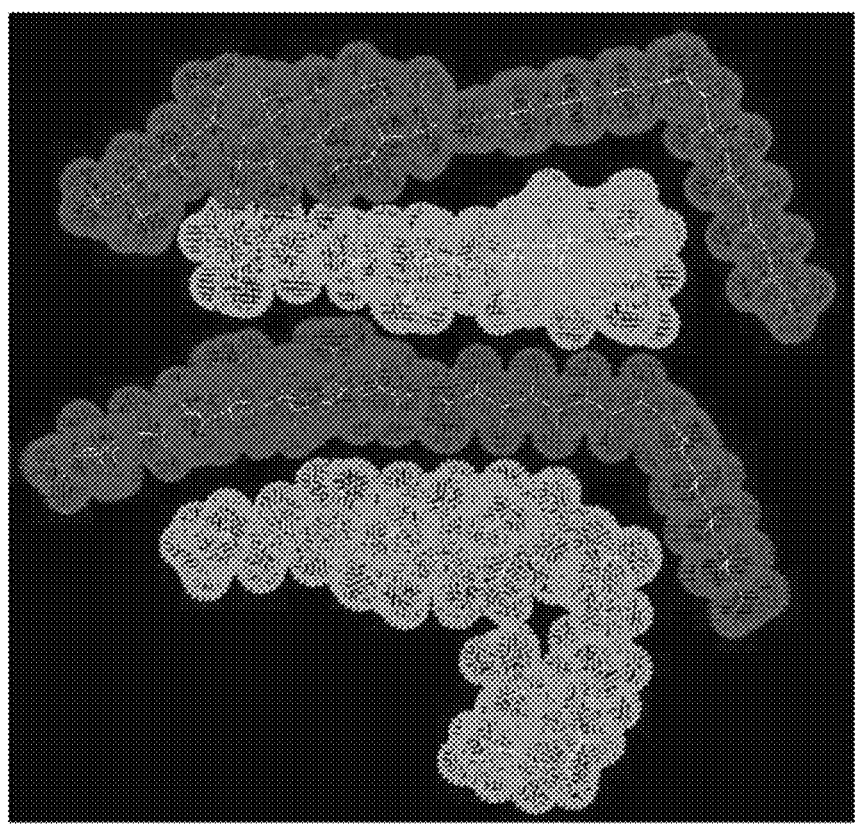
FIG. 68 shows the packing of Cholesteryl Oleate and Cholesteryl Linolenate.
Figure 69:
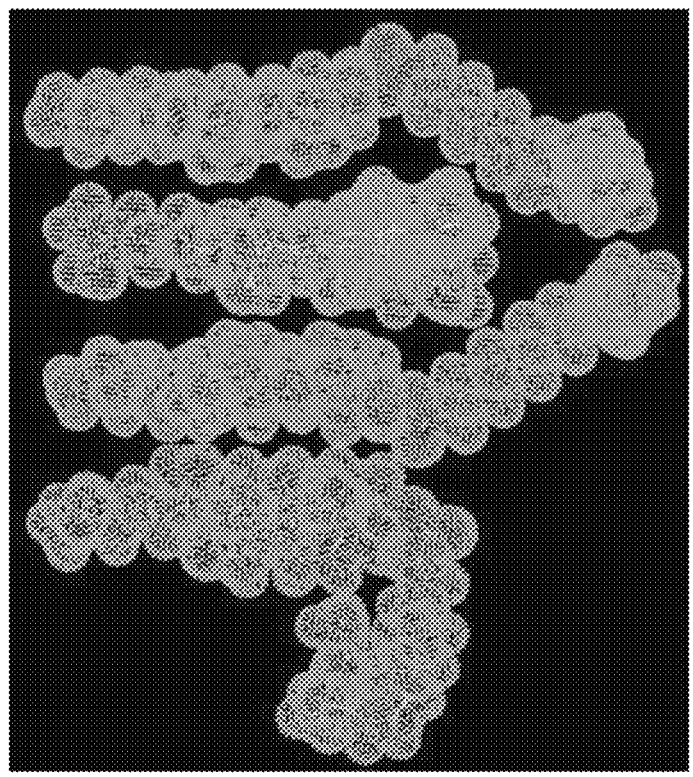
FIG. 69 shows the packing of Cholesteryl Linoleate and Cholesteryl Linolenate.
Figure 70:
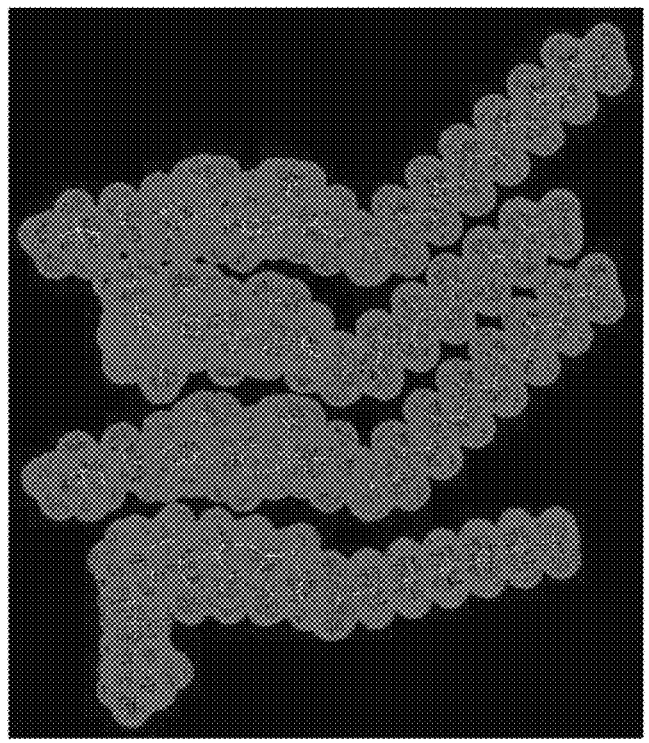
FIG. 70 shows the packing of Cholesteryl Dodecanoate and Cholesteryl Myristate.
Figure 71:
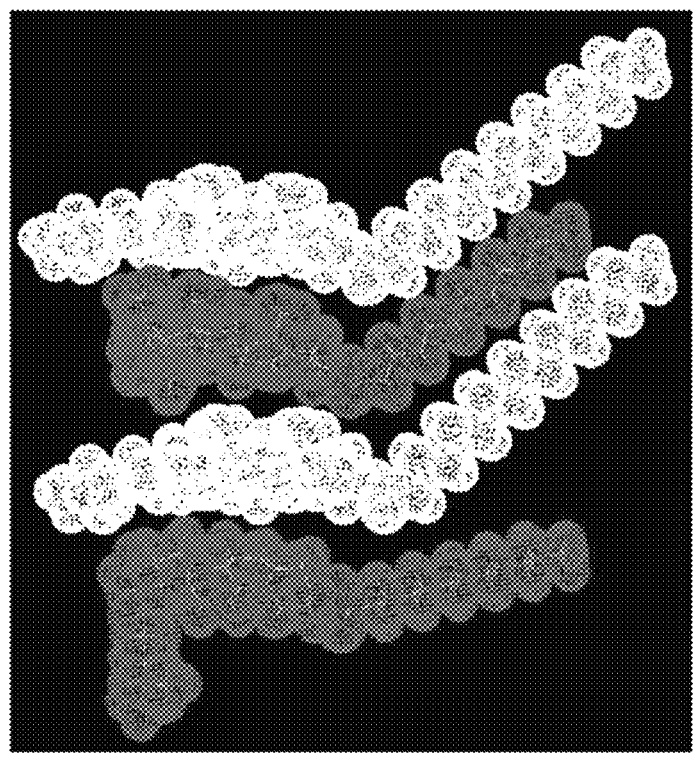
FIG. 71 shows the packing of Cholesteryl Dodecanoate and Cholesteryl Palmitate.
Figure 72:
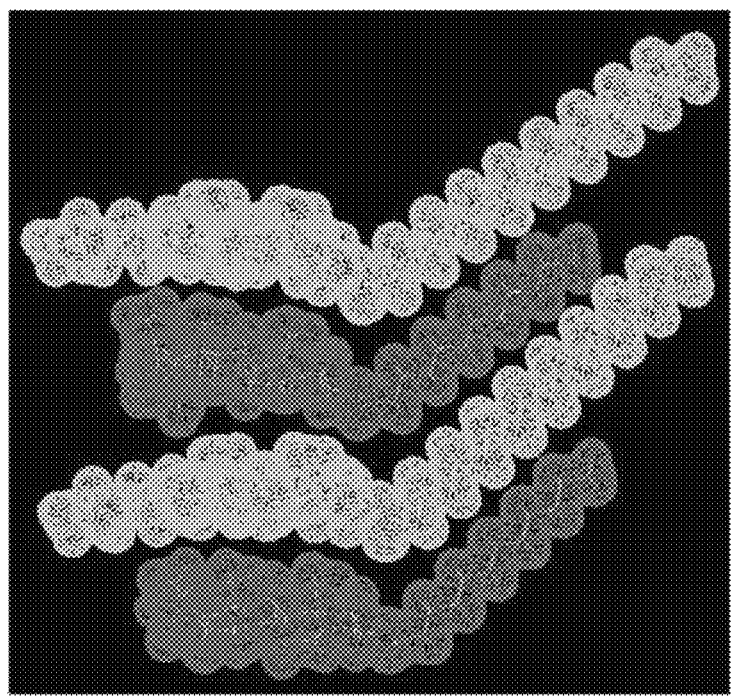
FIG. 72 shows the packing of Cholesteryl Dodecanoate and Cholesteryl Stearate.
Figure 73:
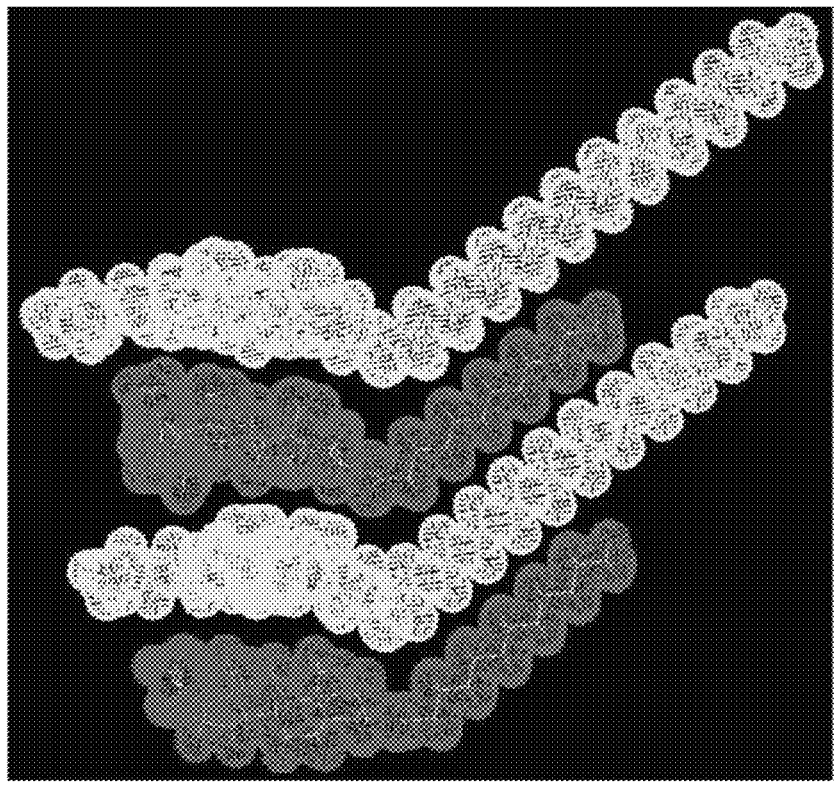
FIG. 73 shows the packing of Cholesteryl Dodecanoate and Cholesteryl Behenate.
Figure 74:
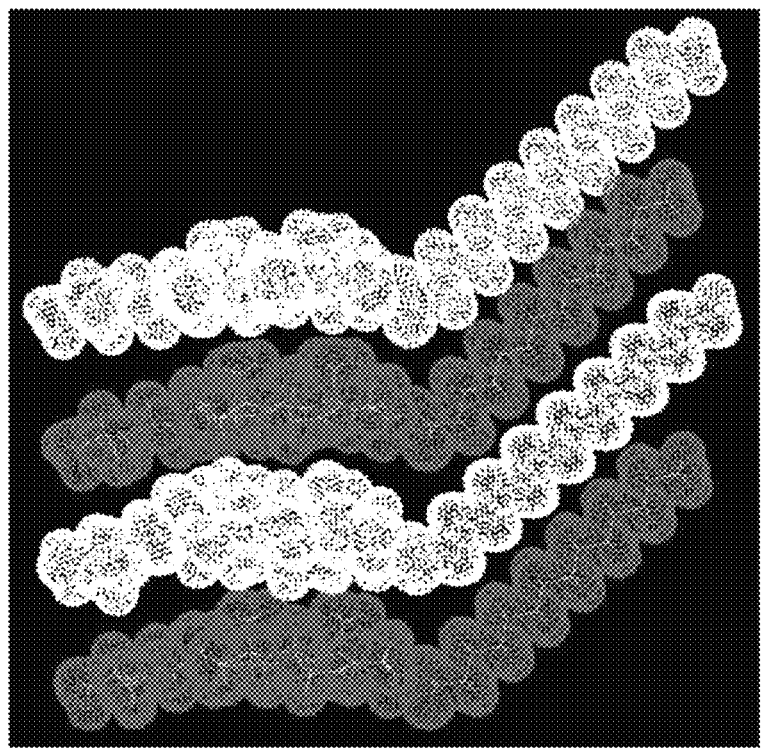
FIG. 74 shows the packing of Cholesteryl Myristate and Cholesteryl Palmitate.
Figure 75:
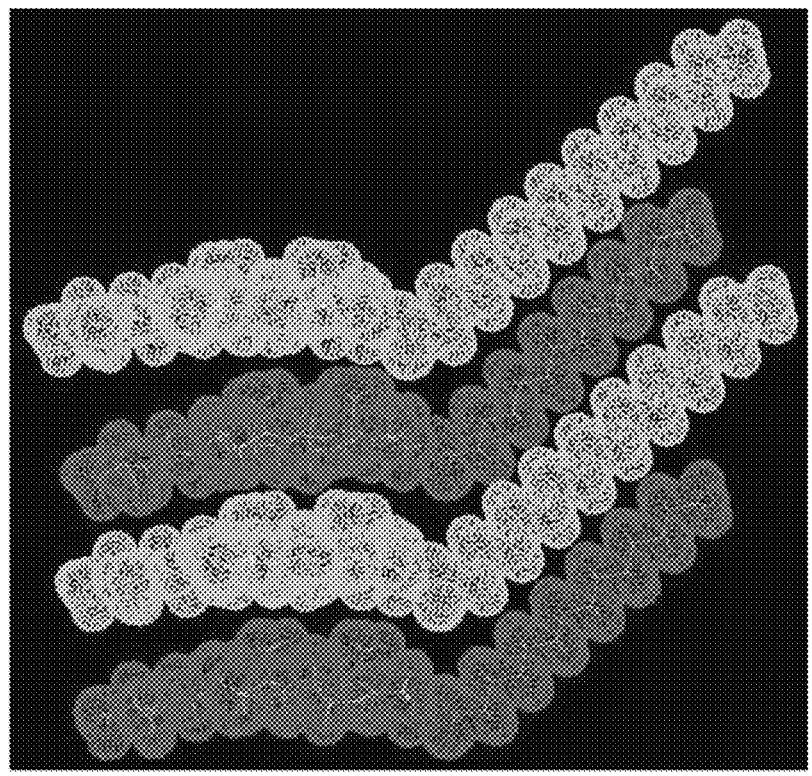
FIG. 75 shows the packing of Cholesteryl Myristate and Cholesteryl Stearate.
Figure 76:
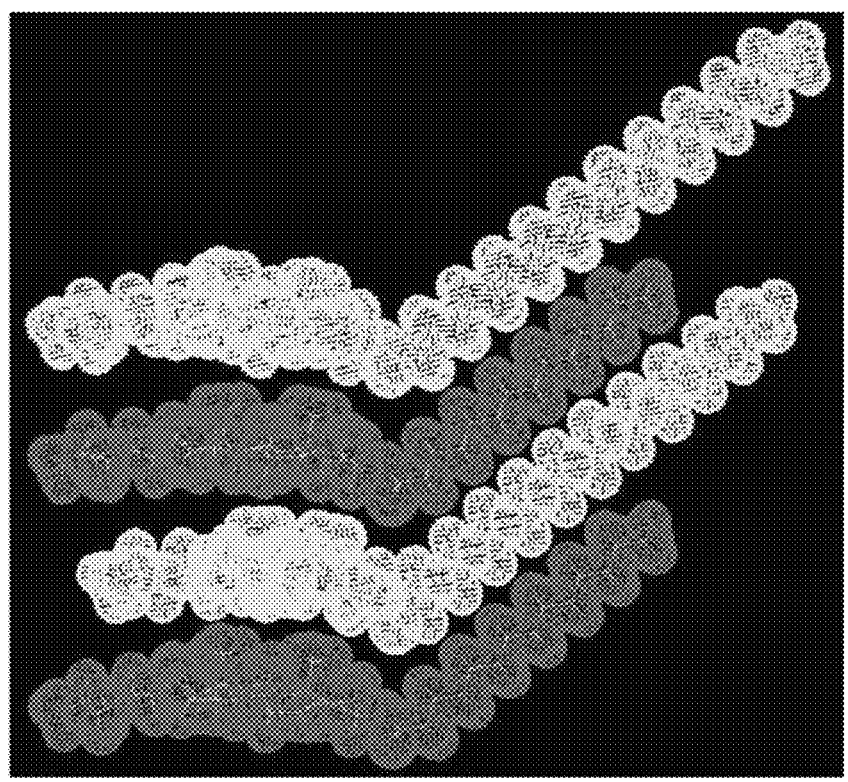
FIG. 76 shows the packing of Cholesteryl Myristate and Cholesteryl Behenate.
Figure 77:
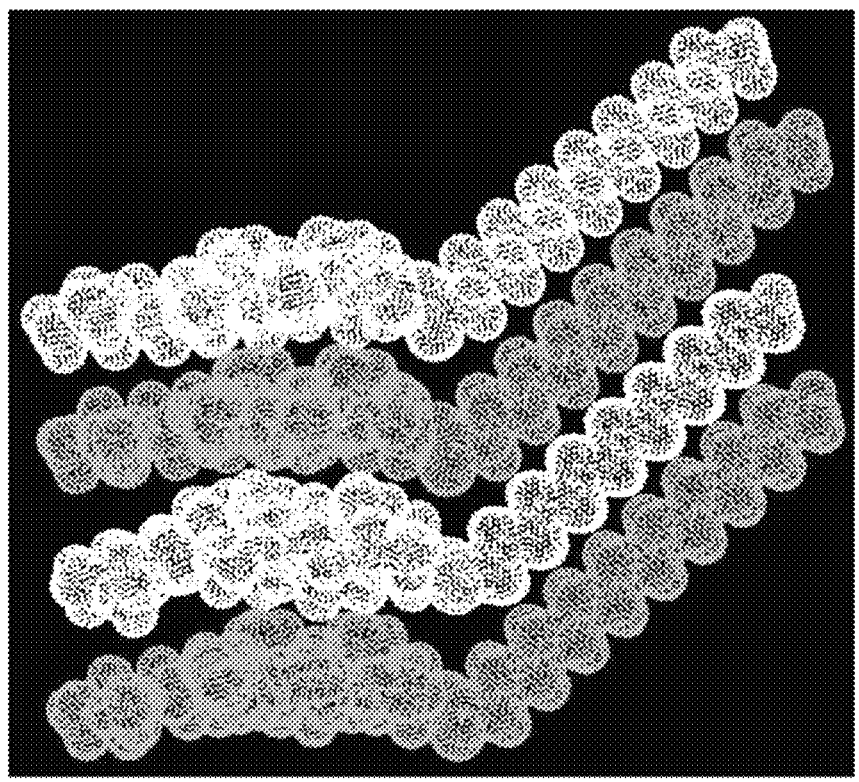
FIG. 77 shows the packing of Cholesteryl Palmitate and Cholesteryl Stearate.
Figure 78:
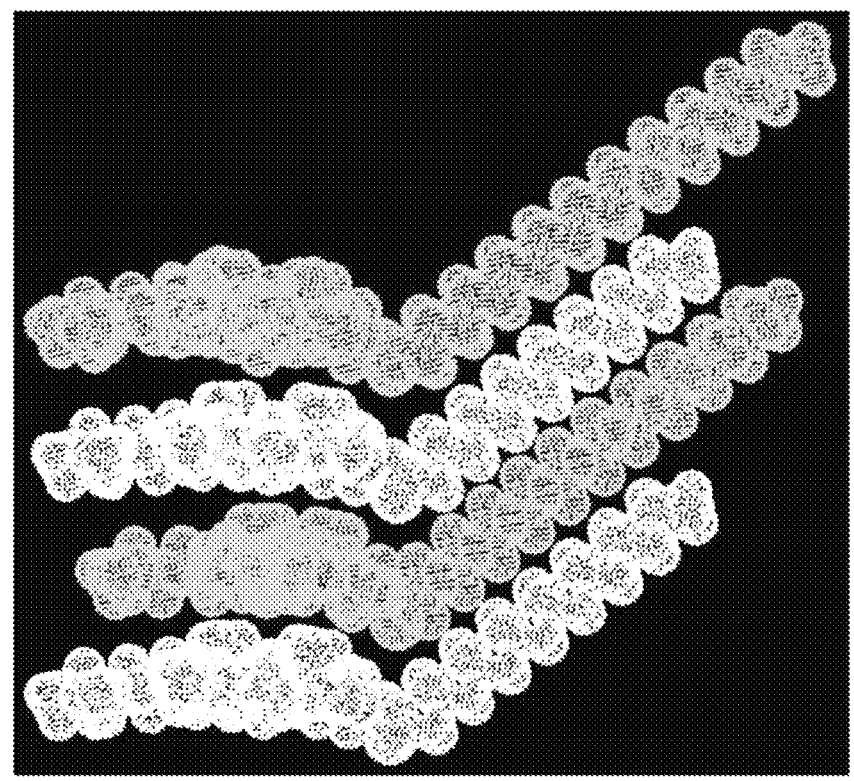
FIG. 78 shows the packing of Cholesteryl Palmitate and Cholesteryl Behenate.

The difference in location of the hydroxyl group may play a part in the packing structure as well. The 20A oxidized sterol has its hydroxyl group on the first carbon on the chain leaving the steroid nucleus. This places the hydroxyl group near the steroid nucleus and not out at the end of the tail coming off of the steroid nucleus. Due to the location of this hydroxyl group being near the steroid ring system, packing is not disrupted as much as if it were further on the tail. For CT and 7B, their hydroxyl groups are located on the steroid nucleus and will not produce the problems like the 25OH did. FIGS. 64 through 78 show the packing structures of these compounds. FIG. 63 depicts the skeletal structures of cholesterol and the oxidized sterols, illustrating the differences in location of the oxygen's location of attachment.

For the binary combinations of 25OH with CT, 20A, and 7B, DSC results demonstrate that they are all co-soluble. A closer inspection of the phase diagrams shows that the binary combination of 25OH and CT (See FIGS. 12A and 12B) produced a negative deviation from the ideal melt line which is not seen when looking at the binary combinations of the other two. The binary combinations of 25OH with 7B (FIGS. 14A and 14B) produce results that are nearly in line with the theoretical results of the ideal melt line. The results for the binary combination of 25OH and 20A (FIGS. 13A and 13B) are close in ideality, in the sense that they lie directly on top of the ideal melt line. Structures of the packed crystal solids probably differ due to the number of oxygens and their locations on the molecule. These oxidized cholesterol have their hydroxyl groups either on the steroid ring (as in the case of 7B and CT) or very near the steroid ring (as in the case of the 20A).

Viewing the phase diagrams for the binary combinations of CT with 7B and CT with 20A, the diagrams depict some positive deviations from the ideal line, but both binary combination systems are co-soluble. The positive deviations are also noted for the binary combinations of CT with 7-Keto. From this, the cholestane triol must play a larger part in the packing structure of the newly formed packed crystals even when it is found in small mole fractions compared to the other compound in the binary system. This could explain why the observed temperatures of the second melt of the binary system produced the higher results shown on the phase diagrams. Also, CT has an additional hydroxyl group, which would be able to hydrogen bond to the other oxidized cholesterol, causing the positive deviation from the ideal melt line.

The only binary combination of 7B that has not been previously discussed here is with 20A. The phase diagram for this binary combination illustrates that over all concentrations the samples are co-soluble. FIGS. 20A and 20B highlight that the experimental results lie just below the theoretical results.

The cholesteryl esters are divided into two groups depending on the structure of their tail section. There are the saturated cholesteryl esters, which have no degree of unsaturation aside from the carbonyl (C=O) at the end attached to the cholesterol molecule. The second classification is unsaturated, cholesteryl esters, which contain a minimum of one carbon—carbon double bond (C=C) in the tail section. Refer to Table 4 below for the discussion of the results and the break down of where each ester is classified.

Figure 21A:
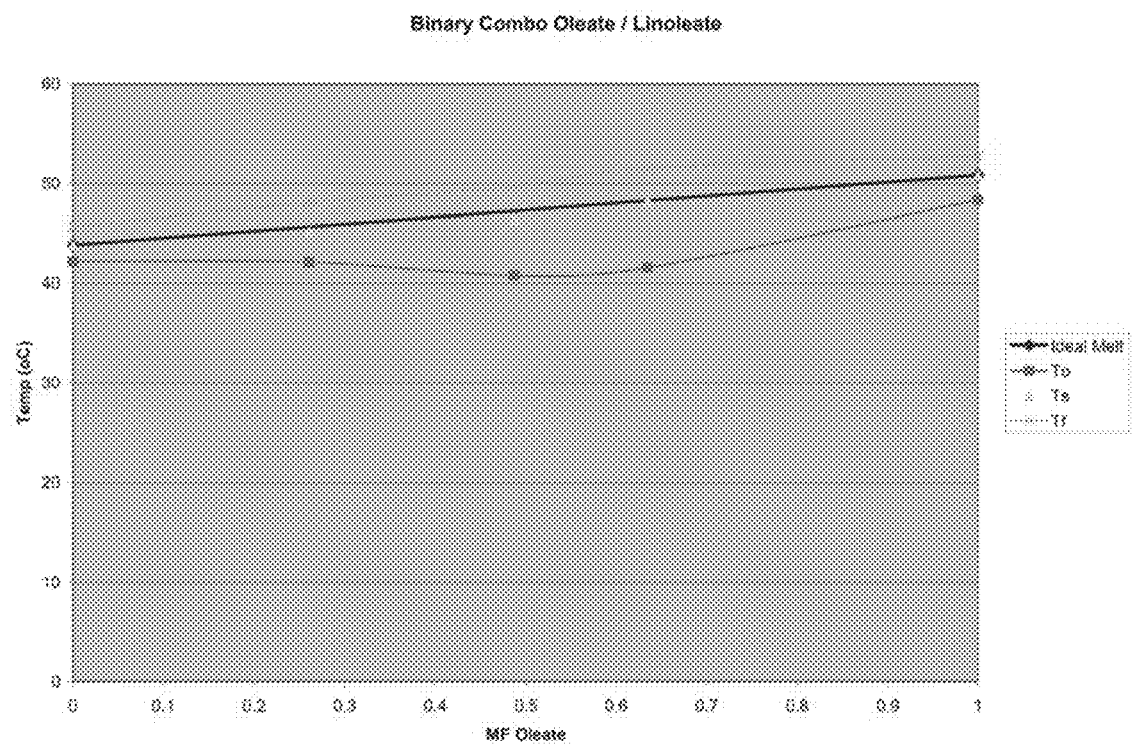
FIG. 21A is a phase diagram for Cholesteryl Oleate and Cholesteryl Linoleate.
Figure 21B:
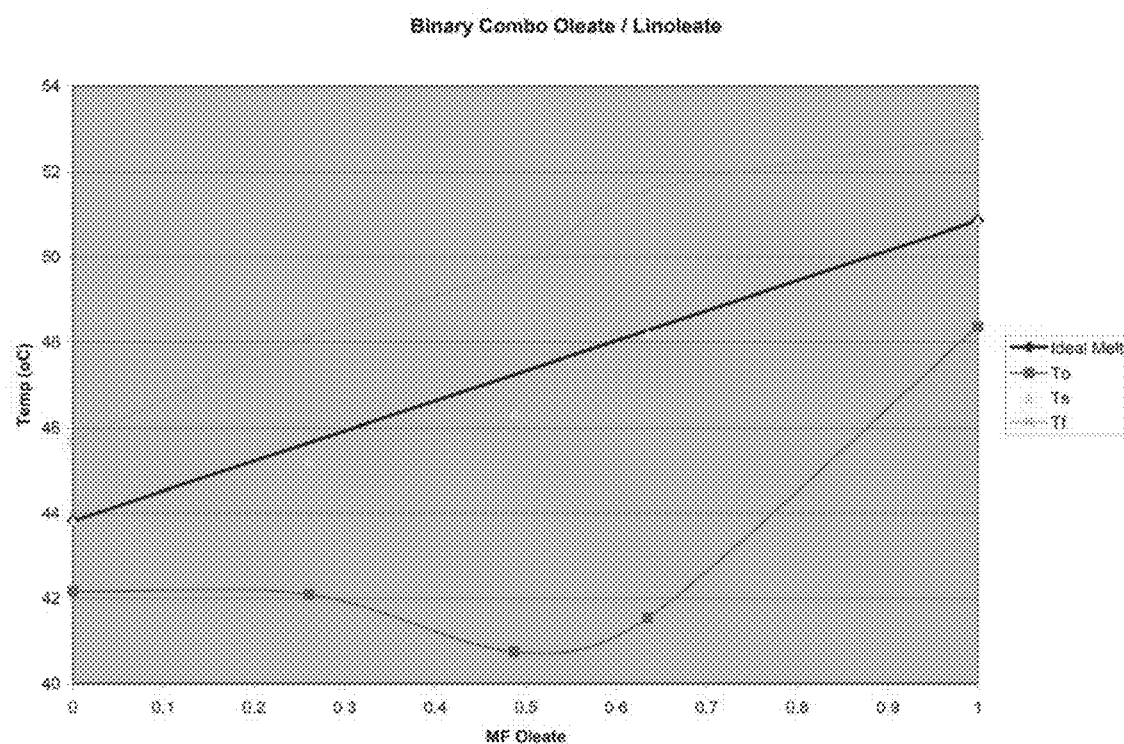
FIG. 21B is an expanded phase diagram of Cholesteryl Oleate and Cholesteryl Linoleate.

The phase diagrams of FIGS. 21A and 21B show that the binary combinations of the unsaturated cholesteryl esters of cholesteryl oleate (CO) and cholesteryl linoleate (CL) are co-soluble with each other. The phase diagrams also show that the $T_s$ temperatures lie almost directly on top the ideal melt line. Thus, the theoretical expectations coincide with the experimental results that are shown on the phase diagram. There is a minimum energy around 0.5 MF of CO for the beginning of the melting of the solid crystal.

Figure 22A:
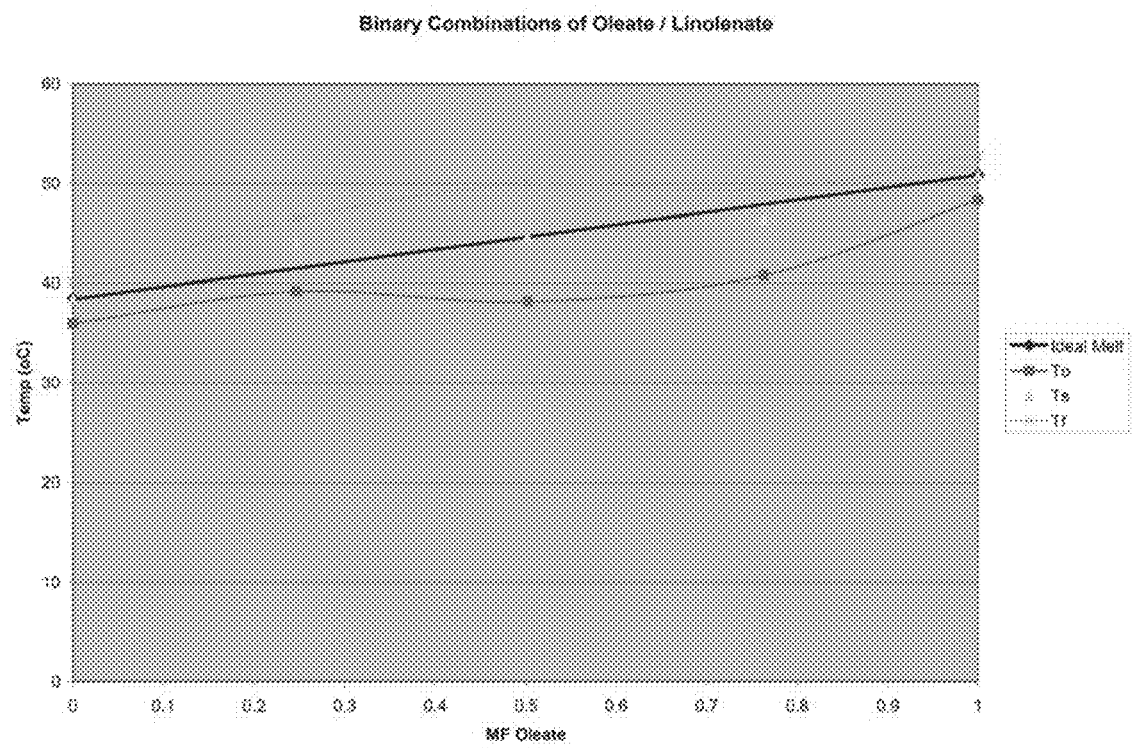
FIG. 22A is a phase diagram of Cholesteryl Oleate and Cholesteryl Linolenate.
Figure 22B:
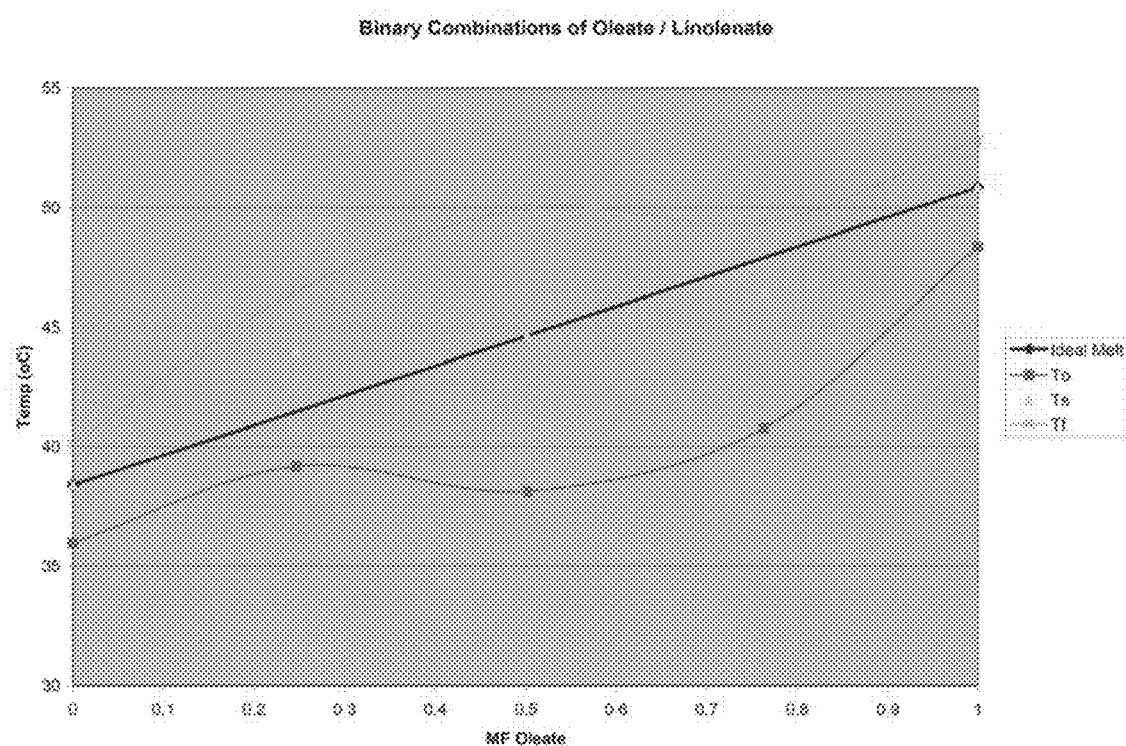
FIG. 22B is an expanded phase diagram of Cholesteryl Oleate and Cholesteryl Linolenate.

The phase diagrams in FIGS. 22A and 22B illustrate that the binary combinations of cholesteryl linolenate (CLn) and CO are co-solubility over all MF concentrations. The peak temperatures nearly coincide with the ideal melt line, so the experimental and theoretical values are relatively close. The solidus line has a minimum energy at 0.5 MF of CO for the range of 0.2-0.8 MF of CO. Aside from that, the solidus and liquidus lines are almost parallel to the ideal melt line.

Figure 23A:
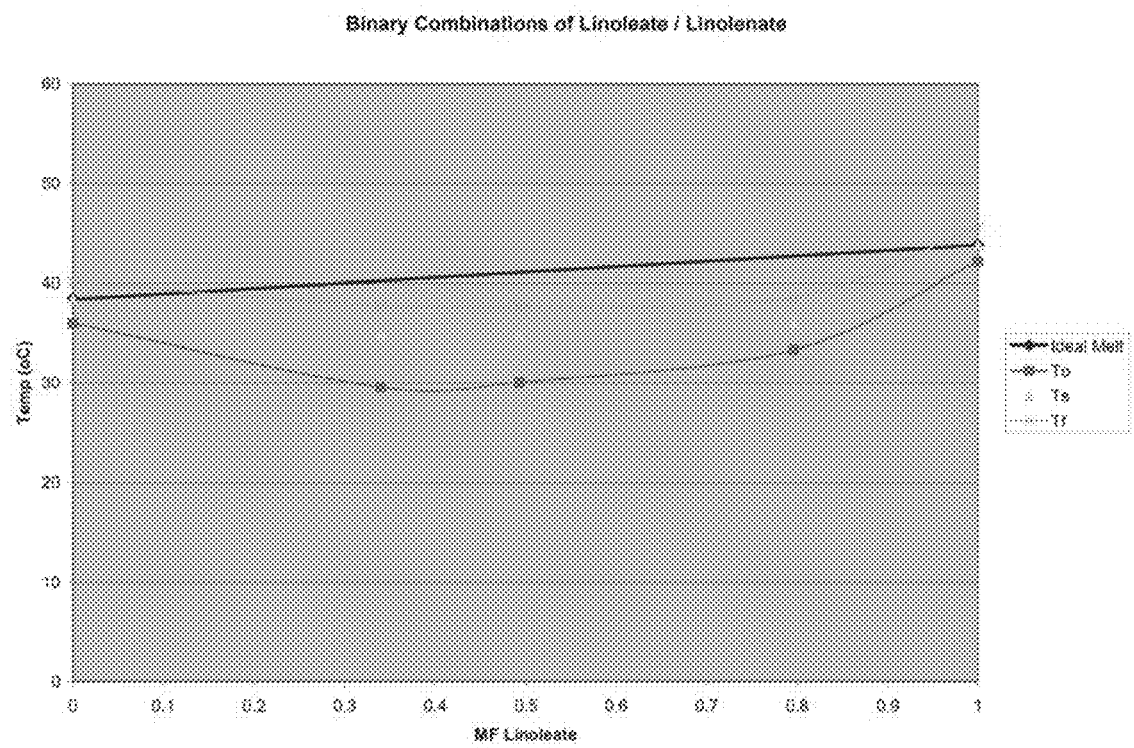
FIG. 23A is a phase diagram of Cholesteryl Linoleate and Cholesteryl Linolenate.
Figure 23B:
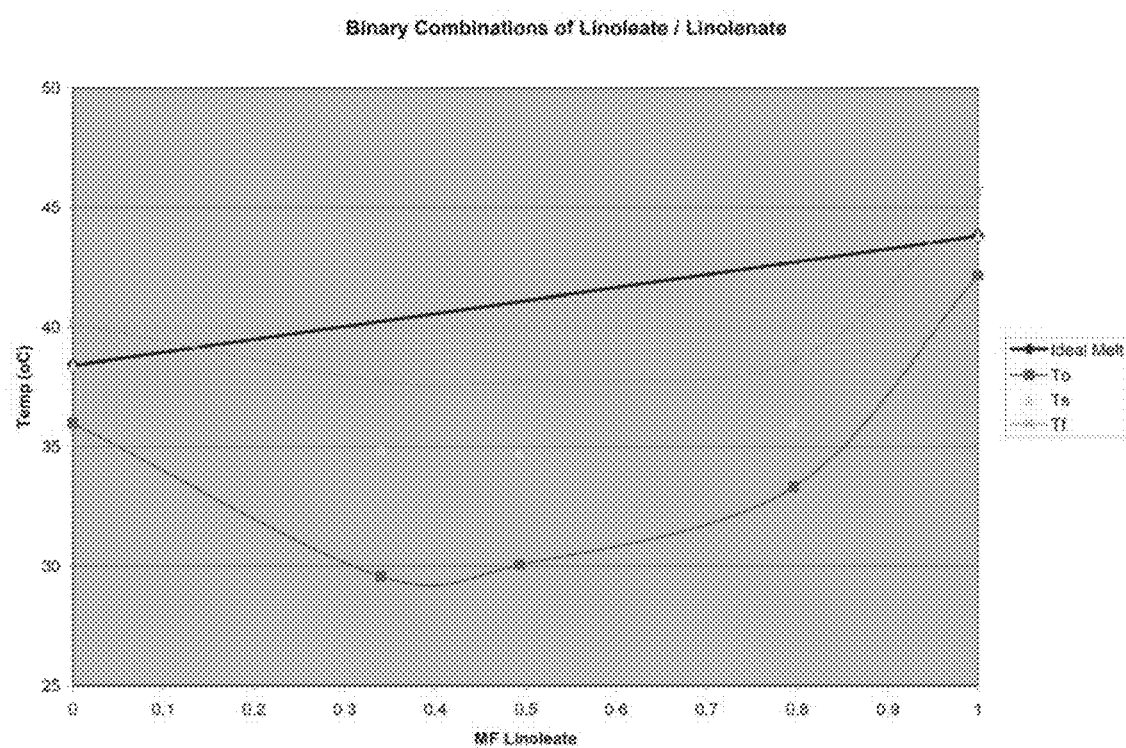
FIG. 23B is an expanded phase diagram of Cholesteryl Linoleate and Cholesteryl Linoleate.

FIGS. 23A and 23B depict the binary phase diagrams for CL and CLn, where a negative deviation from the ideal melt line occurs. The solidus line has an energy minimum around 0.3-0.5 MF of CL. After that point, both lines start increasing in the energy required to melt the solid as the MF of CL increases.

Figure 24A:
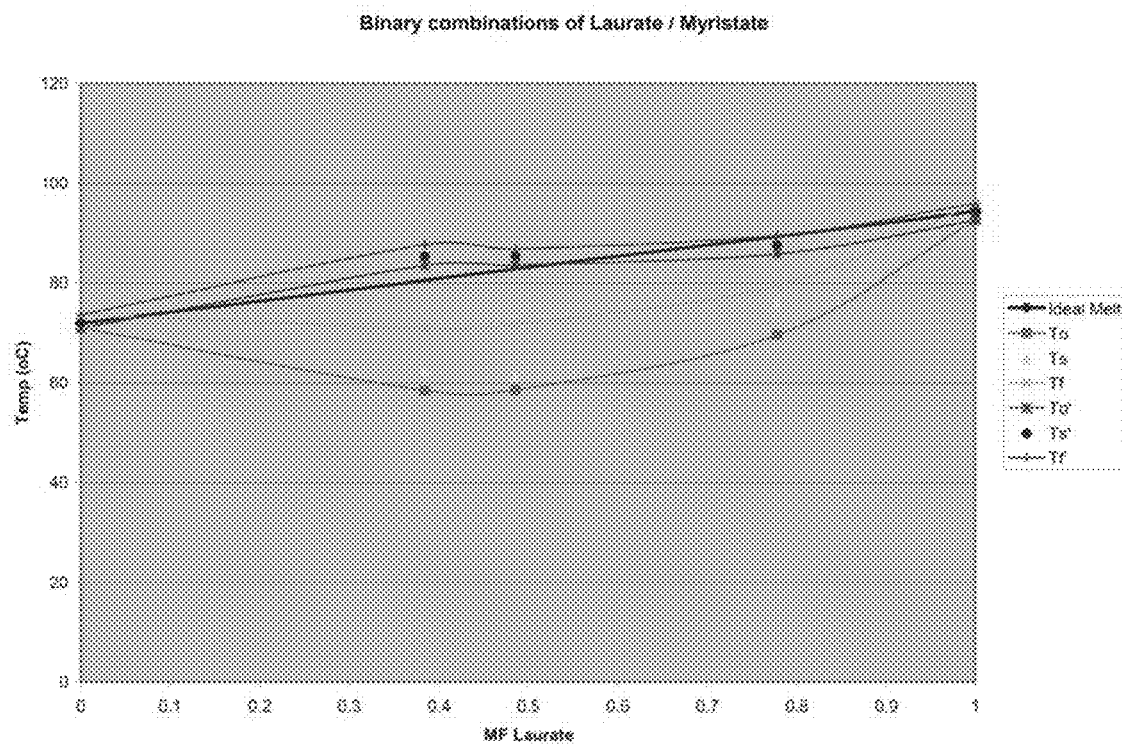
FIG. 24A is a phase diagram of Cholesteryl Laurate and Cholesteryl Myristate.
Figure 24B:
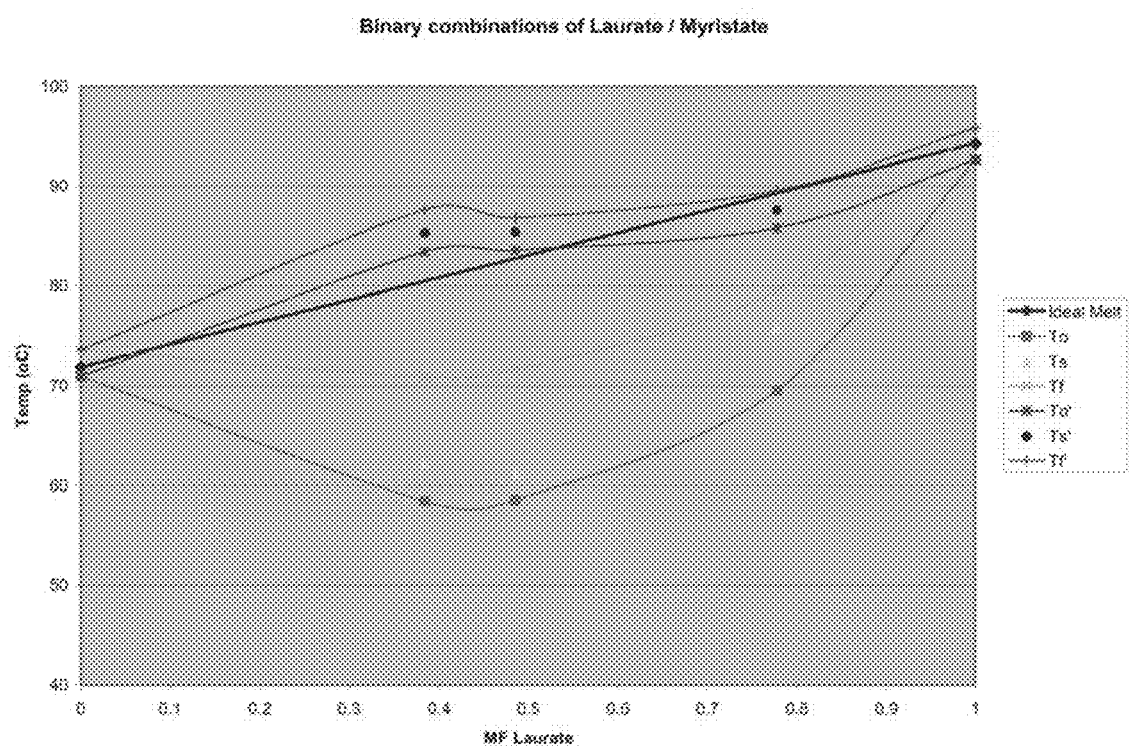
FIG. 24B is an expanded phase diagram of Cholesteryl Laurate and Cholesteryl Myristate.

The phase diagrams for the saturated esters are different from the ones for the unsaturated esters. The binary combinations of cholesteryl dodecanoate (CD) and cholesteryl myristate (CM) in FIGS. 24A and 24B are not co-soluble as can be seen in the phase diagrams. The two esters are close in co-solubility at the extremes of the phase diagram, where the structure was composed of predominantly one of the cholesteryl esters. This suggests that the packed crystal structure can tolerate small concentrations of the other cholesteryl ester. In the middle of the phase diagram, around 0.4-0.6 MF of CD an energy minimum is achieved where the lowest temperature is required to start melting the system and start forming the solid-liquid intermediate state.

Figure 25A:
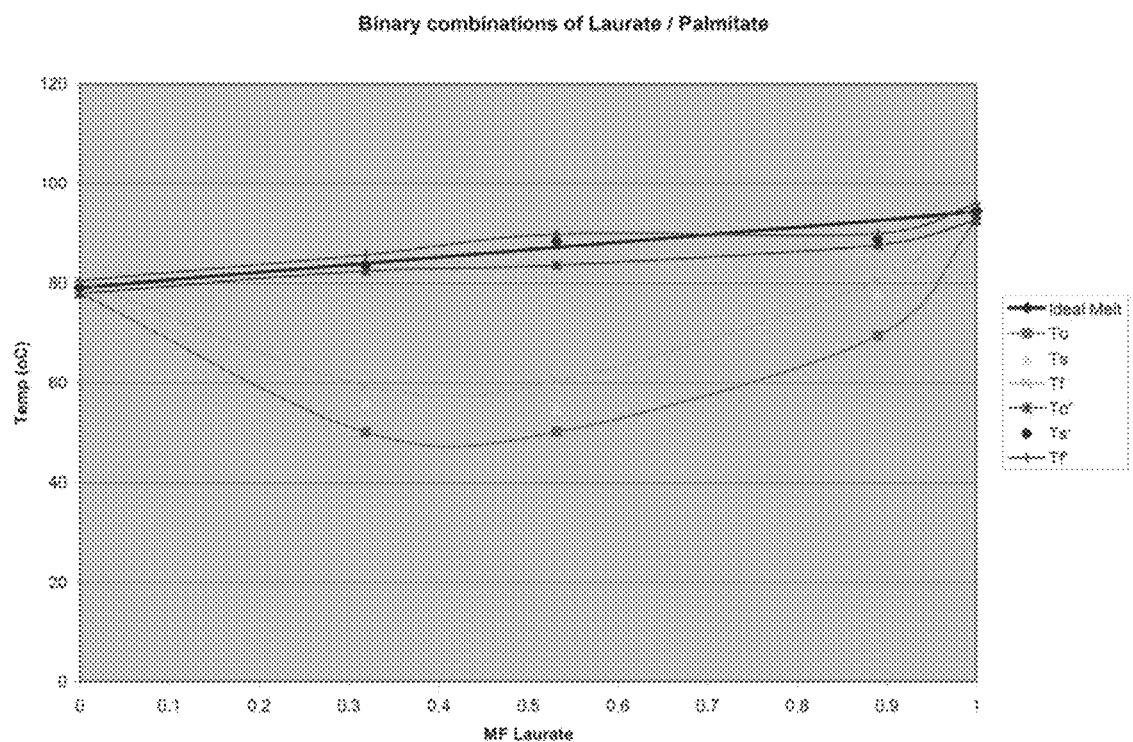
FIG. 25A is a phase diagram of Cholesteryl Laurate and Cholesteryl Palmitate.
Figure 26A:
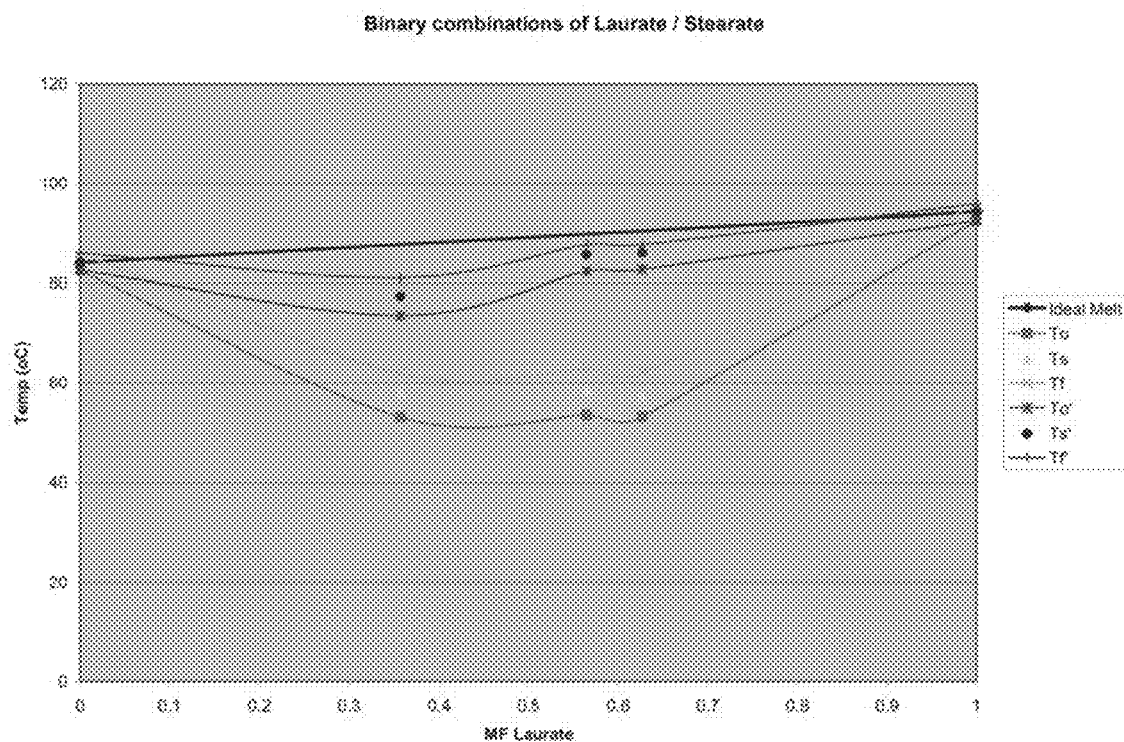
FIG. 26A is a phase diagram of Cholesteryl Laurate and Cholesteryl Stearate.
Figure 26B:
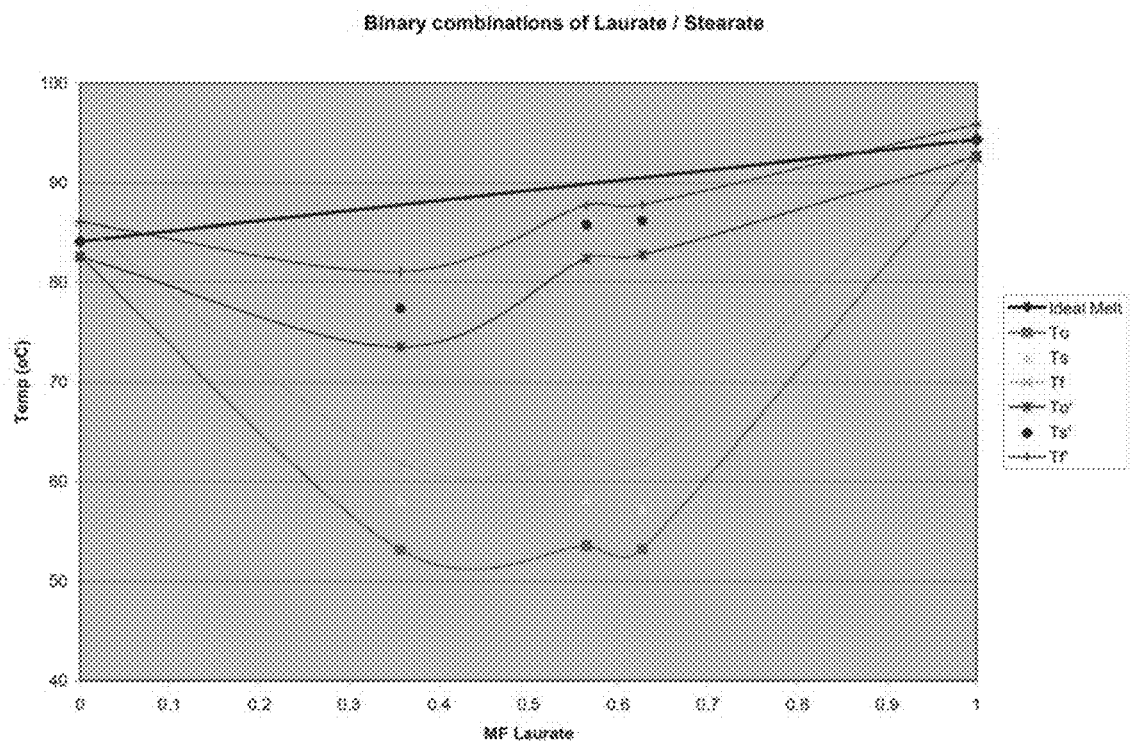
FIG. 26B is an expanded phase diagram of Cholesteryl Laurate and Cholesteryl Stearate.

The phase diagrams in FIGS. 25A and 26B show that CD and cholesteryl palmitate (CP) are not co-soluble at all. The phase diagrams show that the solidus line decreases to reach an energetic minimum at around 0.4 MF of CD before increasing again. The second series of data points that are graphed on the phase diagrams follows the ideal melt line very closely. The two sets of data are closest to each at the ends of the phase diagrams, and show the general deviation in the middle section. As a result of their inability to be co-soluble, a solid-liquid state exists between the solidus and liquidus line.

Figure 25B:
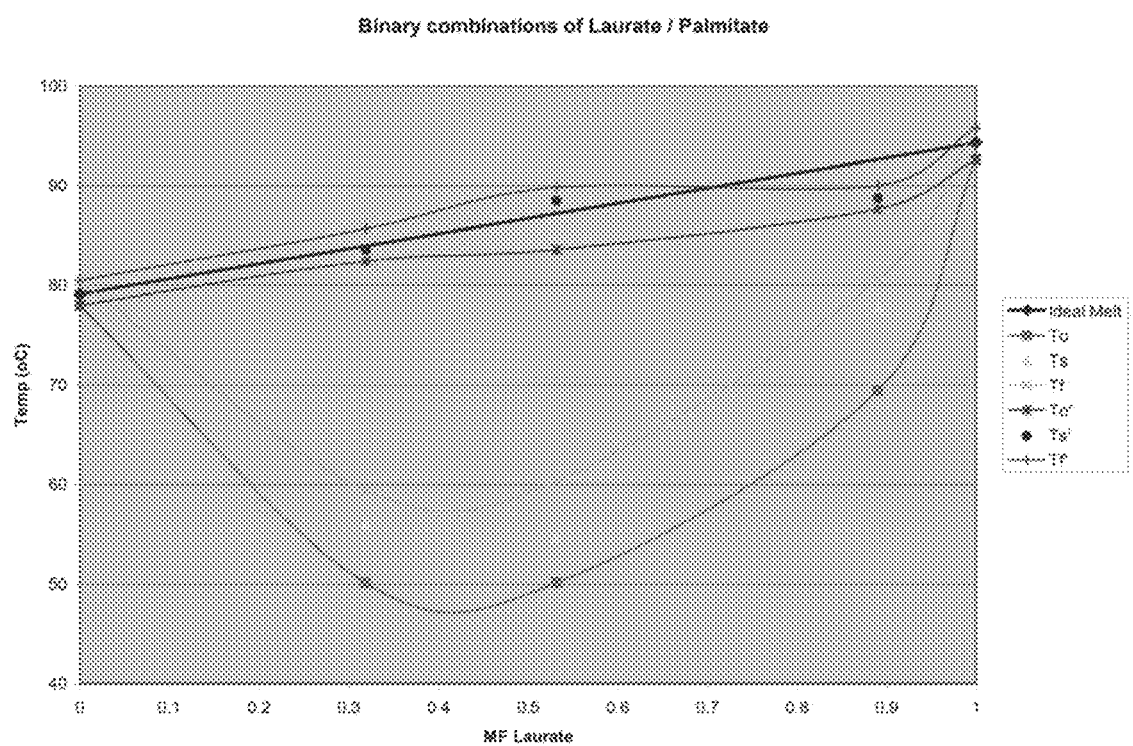
FIG. 25B is an expanded phase diagram of Cholesteryl Laurate and Cholesteryl Palmitate.

The phase diagrams for FIGS. 26A and 26B illustrate that the binary combinations for CD and cholesteryl stearate (CS) are not co-soluble over any concentration range. The solidus line has a minimum that is around 0.4-0.6 MF of CD, followed by increasing in energy again after the minimum. The second set of data points is located below the ideal melt curve, and is not as far apart as the data in FIGS. 25A and 25B show for the binary combinations of CD and CP. Due to the lack of co-solubility, as the MF of CD increases, the energy needed to move the system from the solid-liquid to all liquid increases since the area between the curves increases.

Figure 27A:
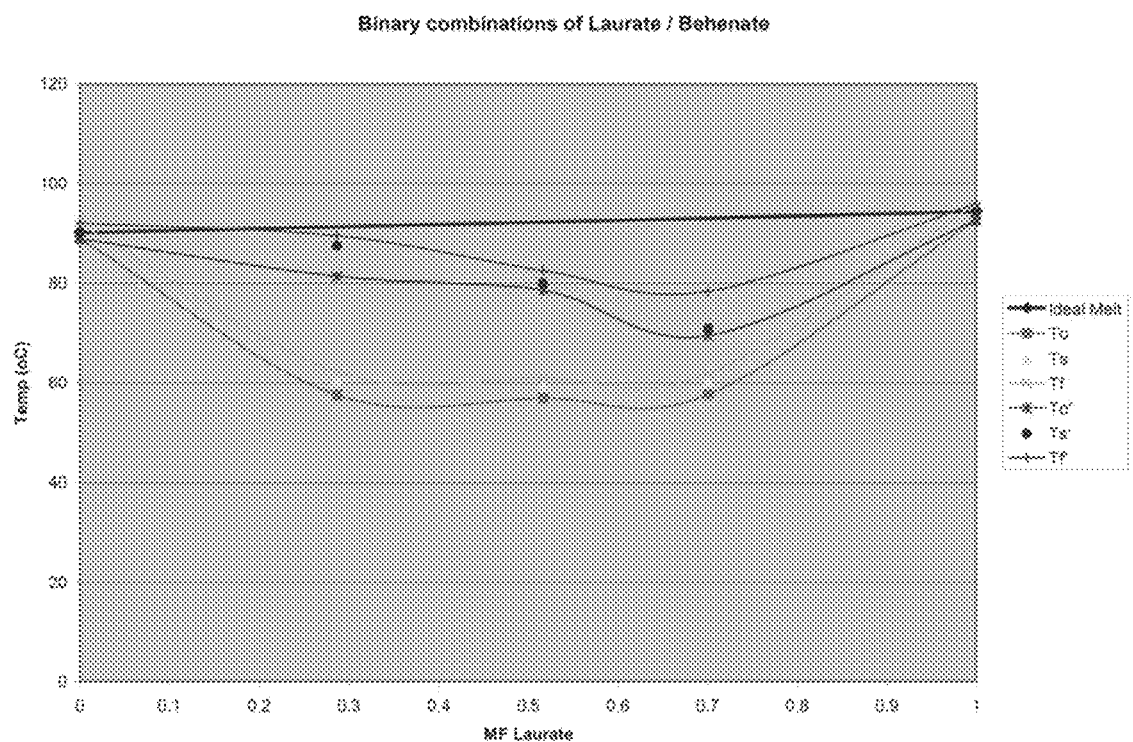
FIG. 27A is a phase diagram of Cholesteryl Lartrate and Cholesteryl Behenate.
Figure 27B:
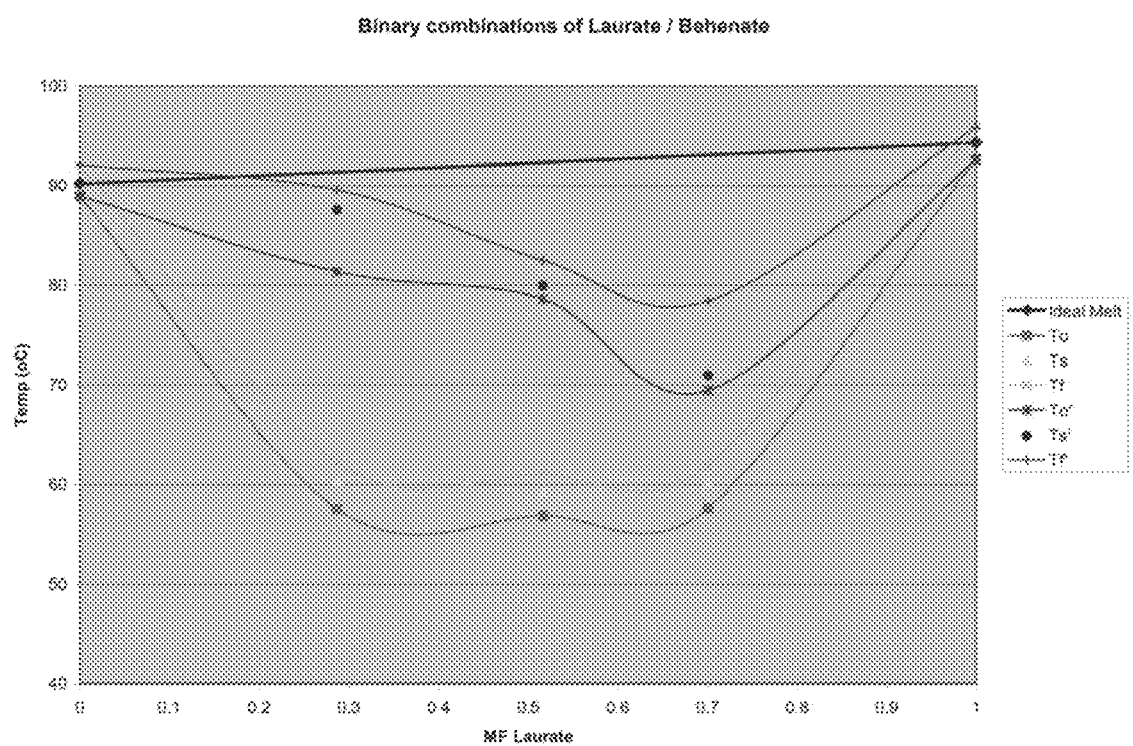
FIG. 27B is an expanded phase diagram of Cholesteryl Laurate and Cholesteryl Behenate.

The phase diagrams of FIGS. 27A and 27B show that CD and cholesteryl behenate (CB) are not co-soluble, since there are two separate points per MF. It is shown that as you move from 0 to 1 MF of CD the lack of co-solubility decreases since the two separate curves start to converge towards a common point.

Figure 28A:
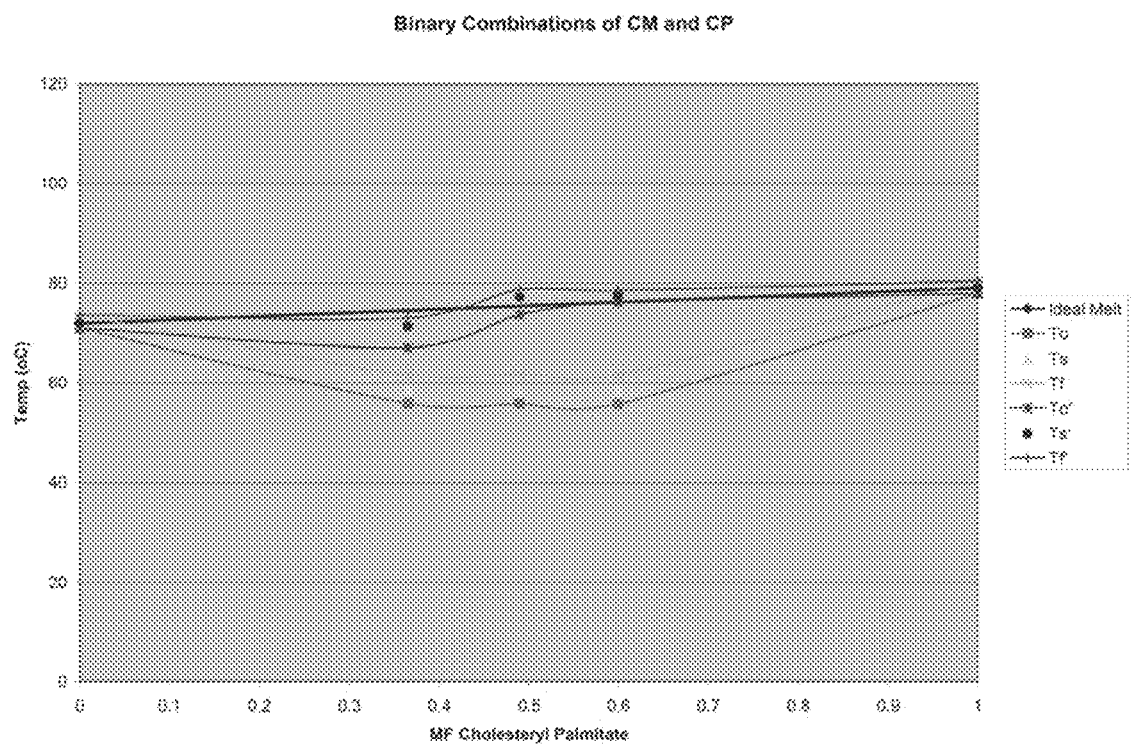
FIG. 28A is a phase diagram of Cholesteryl Myristate and Cholesteryl Palmitate.
Figure 28B:
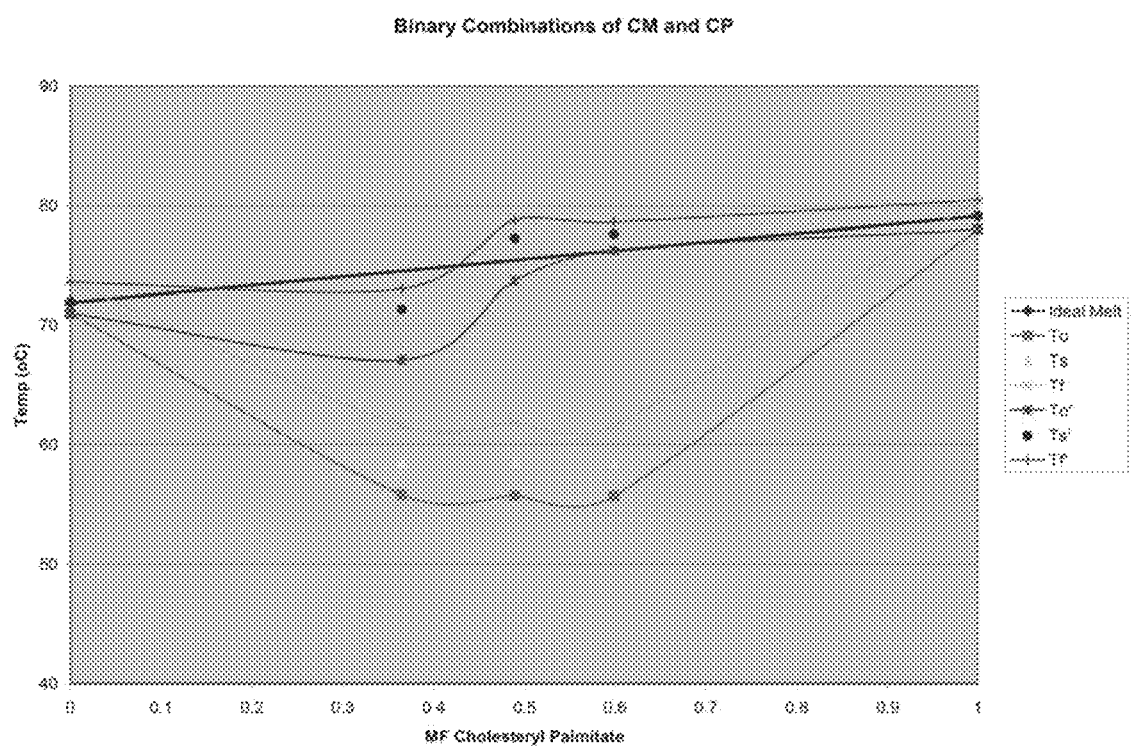
FIG. 28B is an expanded phase diagram of Cholestetyl Myristate and Cholesteryl Palmitate.

FIGS. 28A and 28B illustrates that the phase diagrams for the binary combination of CM and CP increases their lack of co-solubility as the MF of CP increases. The phase diagrams show this as the two sets of data points diverge from each other.

Figure 29A:
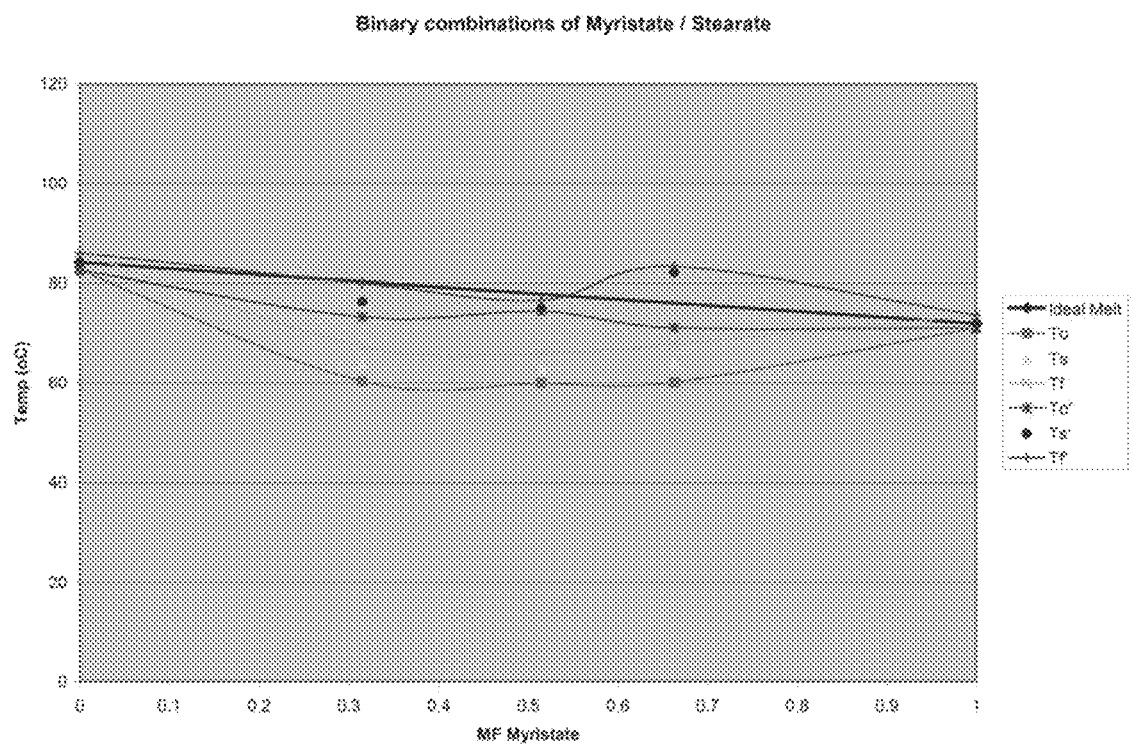
FIG. 29A is a phase diagram of Cholesteryl Myristate and Cholesteryl Stearate.
Figure 29B:
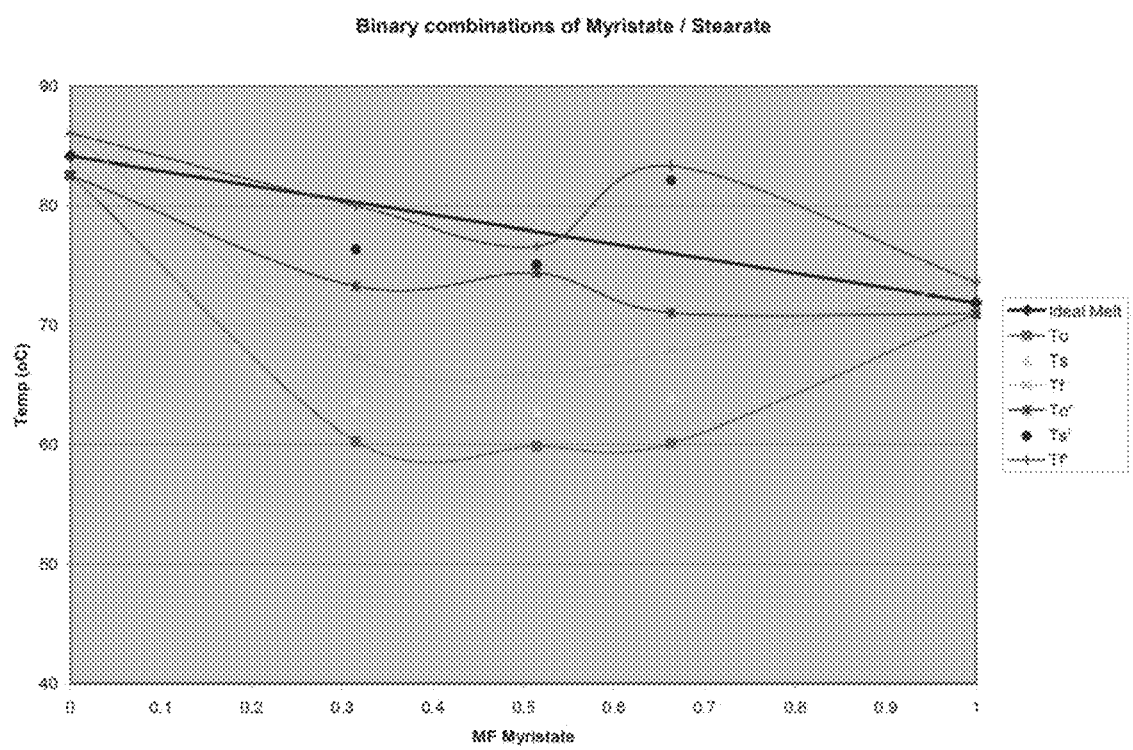
FIG. 29B is an expanded phase diagram of Cholesteryl Myristate and Cholesteryl Stearate.

The phase diagrams for FIGS. 29A and 29B show that the binary system of CM and CS tend to follow the ideal melt line, even though they do not lie on top of it. Also, the differences in the lack of co-solubility of the two are shown by the closeness of the data points for the two curves.

Figure 30A:
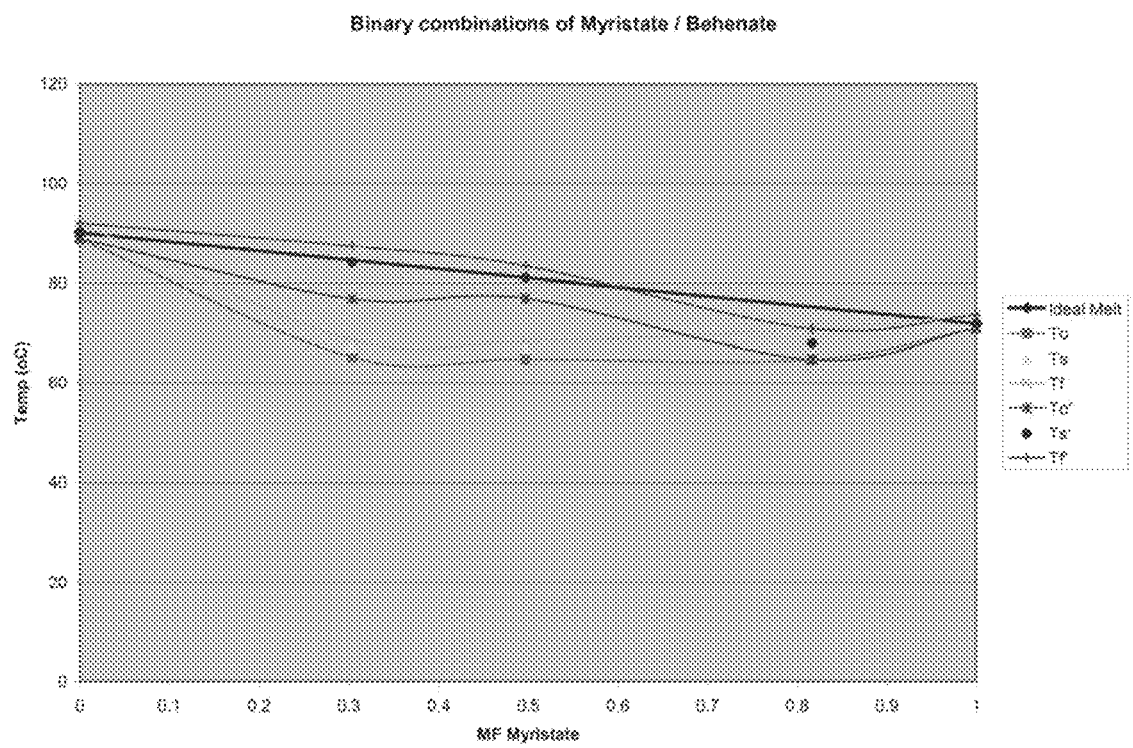
FIG. 30 is a phase diagram of Cholesteryl Myristate and Cholesteryl Behenate.
FIG. 30B is an expanded phase diagram of Cholesteryl Myristate and Cholesteryl Behenate.
Figure 30B:
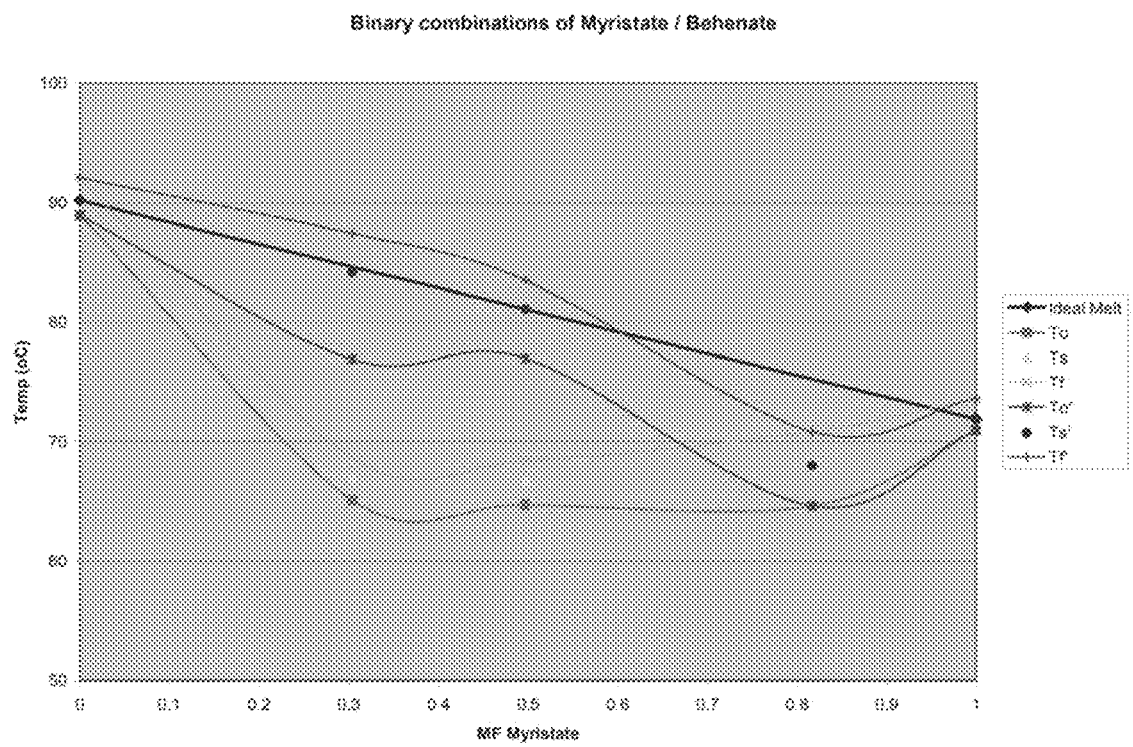

In FIGS. 30A and 30B, the phase diagrams illustrate that as the MF for CM increases the data points from the binary system of CM and CB will converge and become co-soluble with each other around 0.8-1 MF of CM. This was not seen in the other phase diagrams to this point.

Figure 31A:
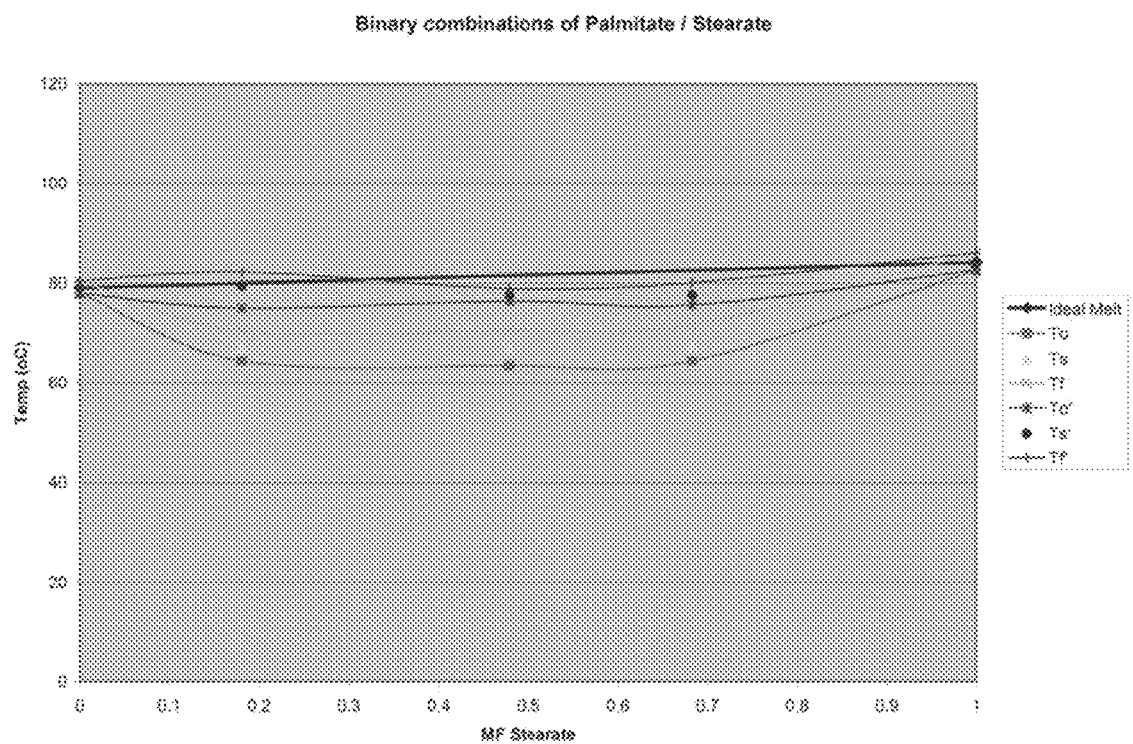
FIG. 31A is a phase diagram of Cholesteryl Palmitate and Cholesteryl Stearate.
Figure 31B:
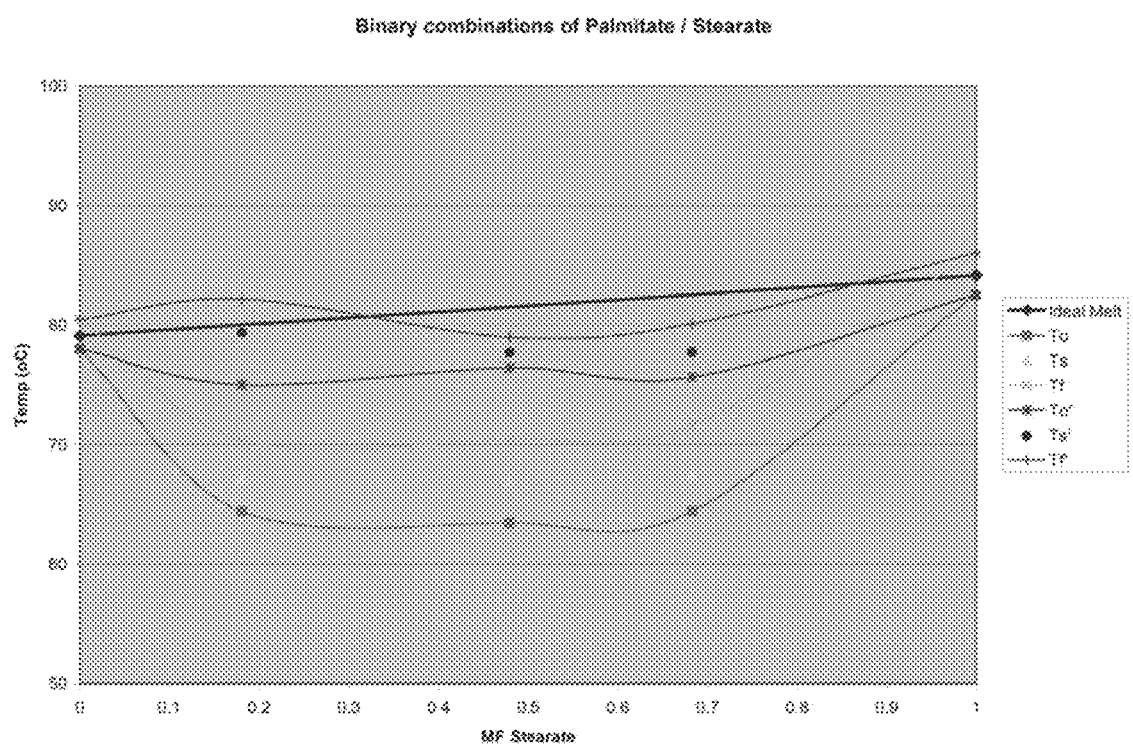
FIG. 31B is an expanded phase diagram of Cholesteryl Palmitate and Cholesteryl Stearate.

The phase diagrams in FIGS. 31A and 31B for the binary system of CP and CS show that there is a lack of co-solubility. However, moving from the middle concentrations towards the extremes, the lack of co-solubility decreases and the binary combinations become more soluble with each other. From this, the packing structure is tolerable to the small deviations in the different concentrations.

Figure 32A:
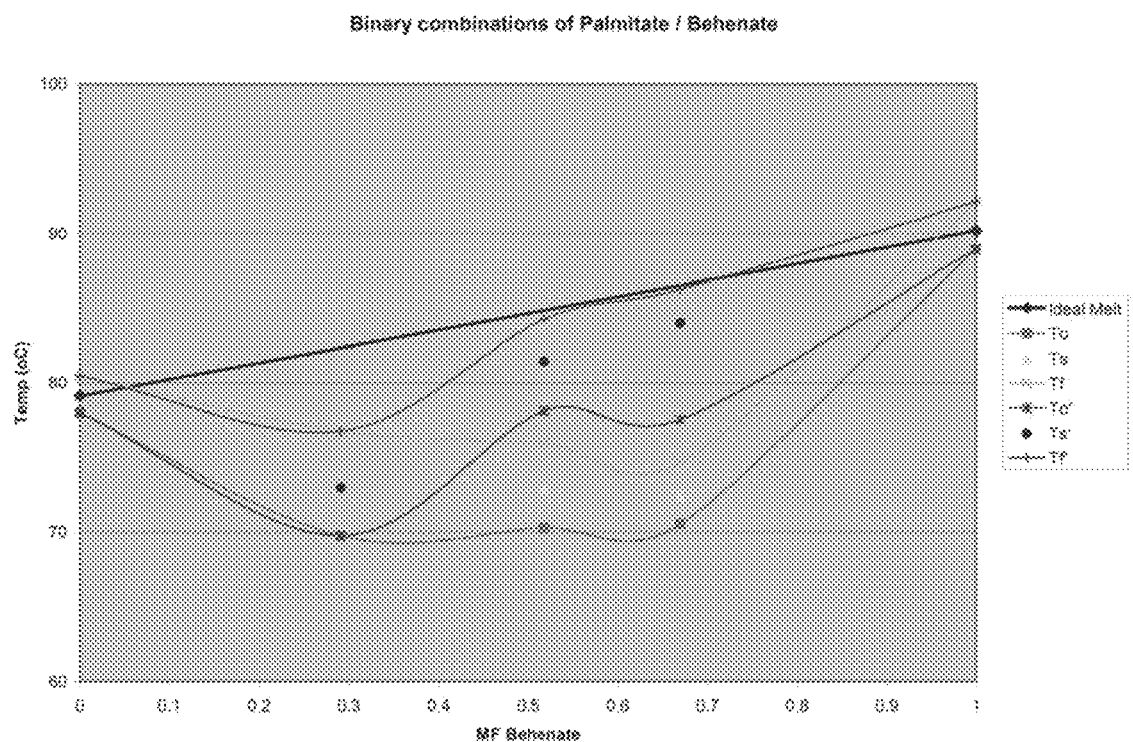
FIG. 32A is a phase diagram of Cholesteryl Palmitate and Cholesteryl Behenate.
Figure 32B:
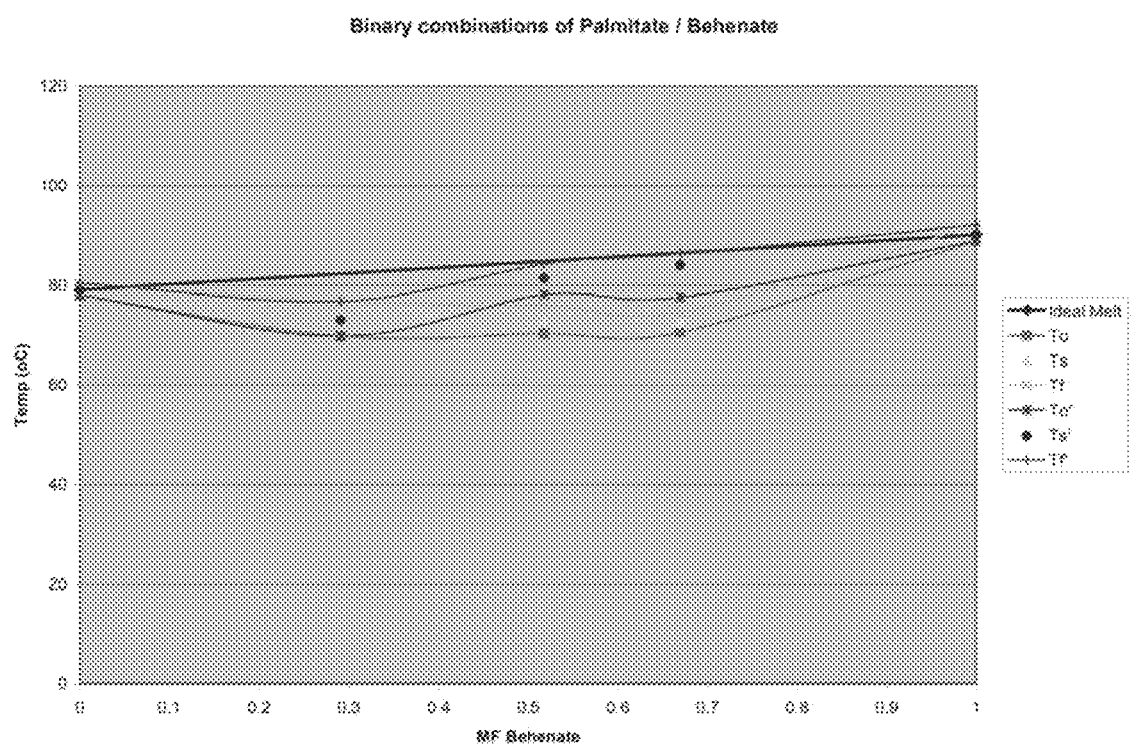
FIG. 32B is an expanded phase diagram of Cholesteryl Palmitate and Cholesteryl Behenate.

The phase diagrams for FIGS. 32A and 32B show that the binary combinations for CP and CB are rather co-soluble at low concentrations of CB compared to those of CP. Also, the binary system tends to go back towards co-solubility as the mole fraction of CB goes from 0.7-1 relative to CP.

Figure 33A:
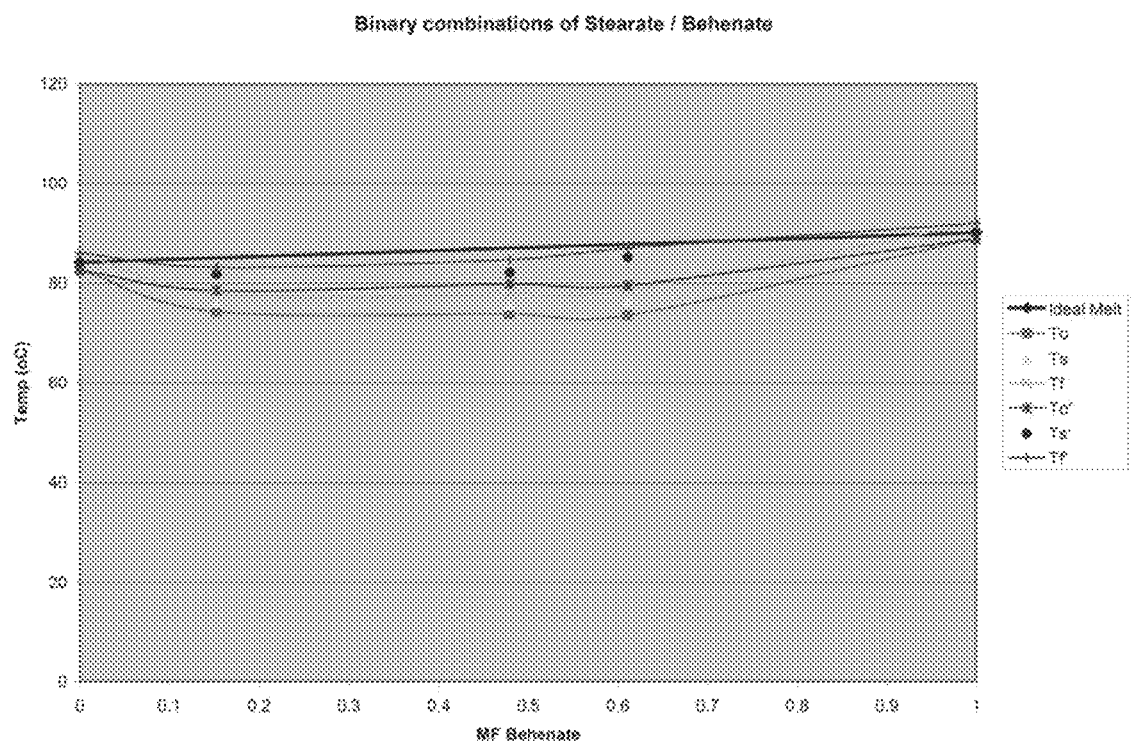
FIG. 33A is a phase diagram of Cholesteryl Stearate and Cholesteryl Behenate.
Figure 33B:
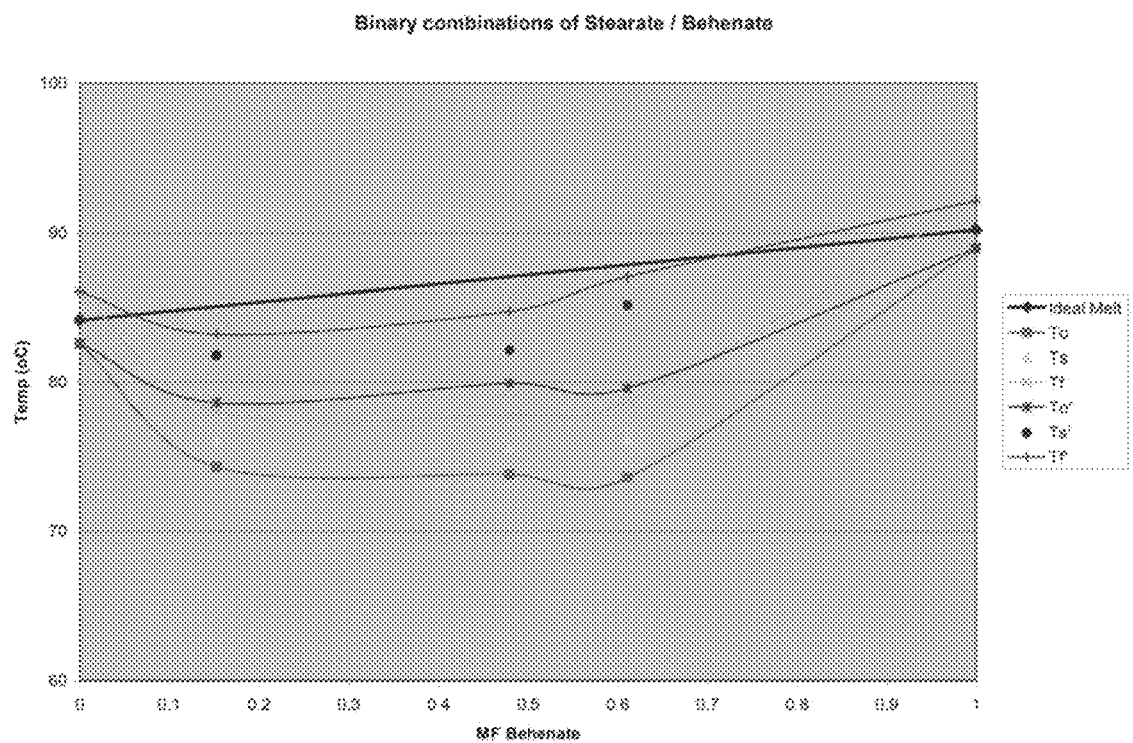
FIG. 33B is an expanded phase diagram of Cholesteryl Stearate and Cholesteryl Behenate.
Figure 34:
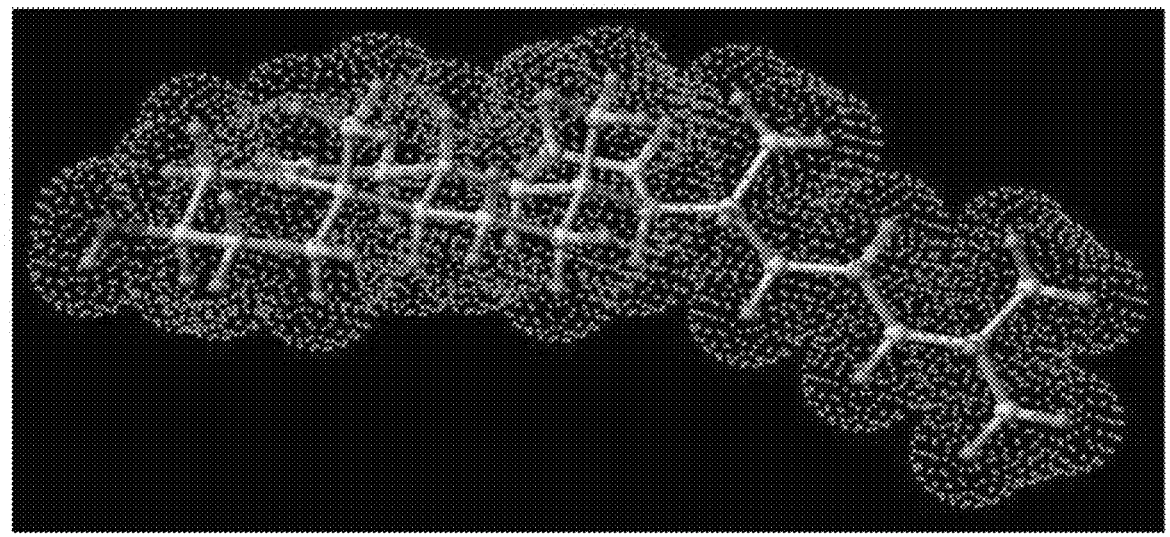
FIG. 34 is a dot surface model of Cholesterol.
Figure 35:
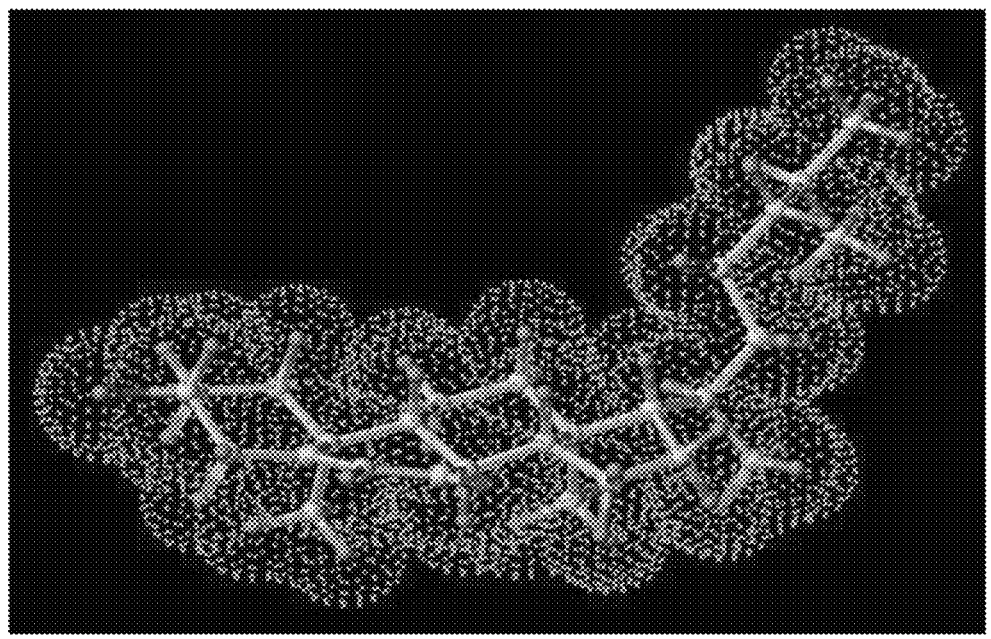
FIG. 35 is a dot surface model of 7-Ketocholesterol.
Figure 36:
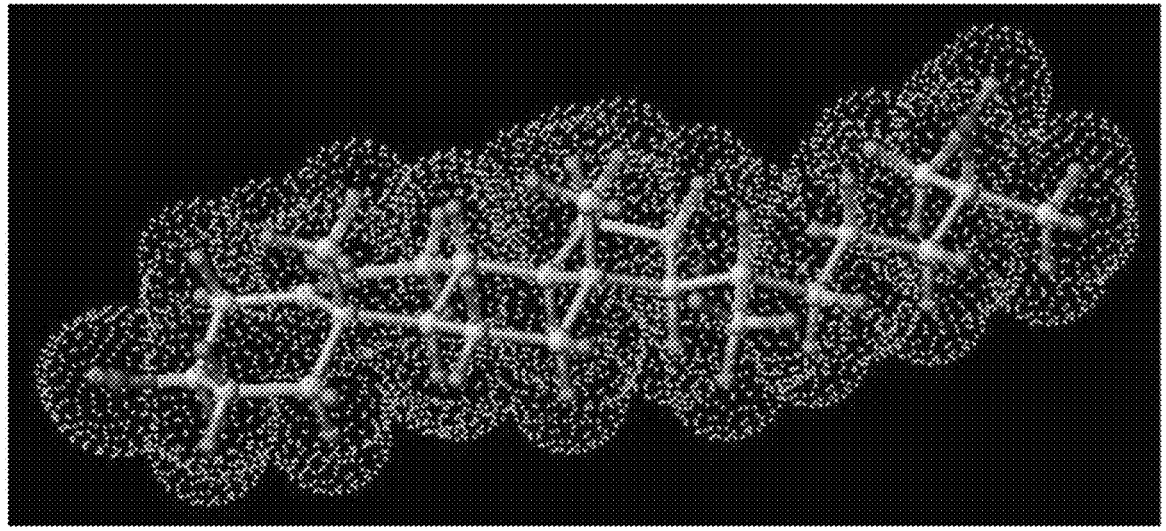
FIG. 36 is a dot surface model of 25-Hydroxycholesterol.
Figure 37:
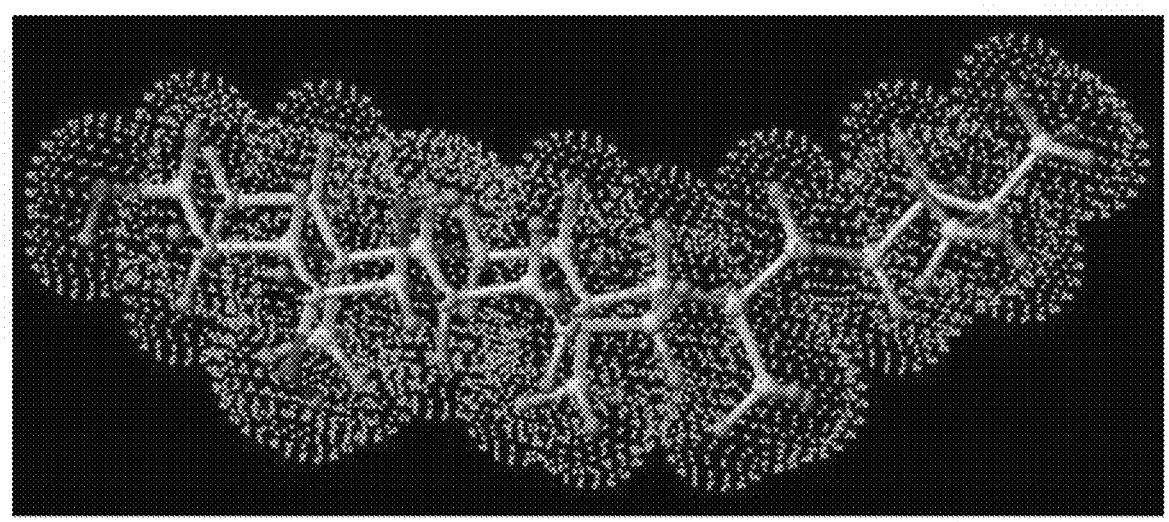
FIG. 37 is a dot surface model of Cholestane Triol.
Figure 38:
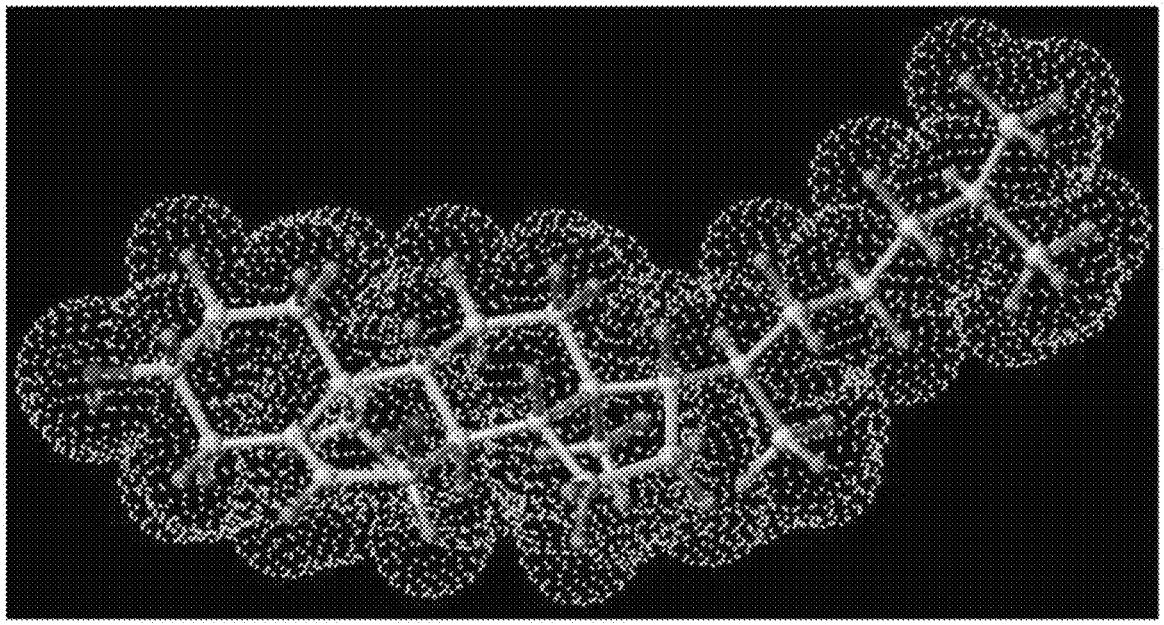
FIG. 38 is a dot surface model of 7B-Hydroxycholesterol.
Figure 39:
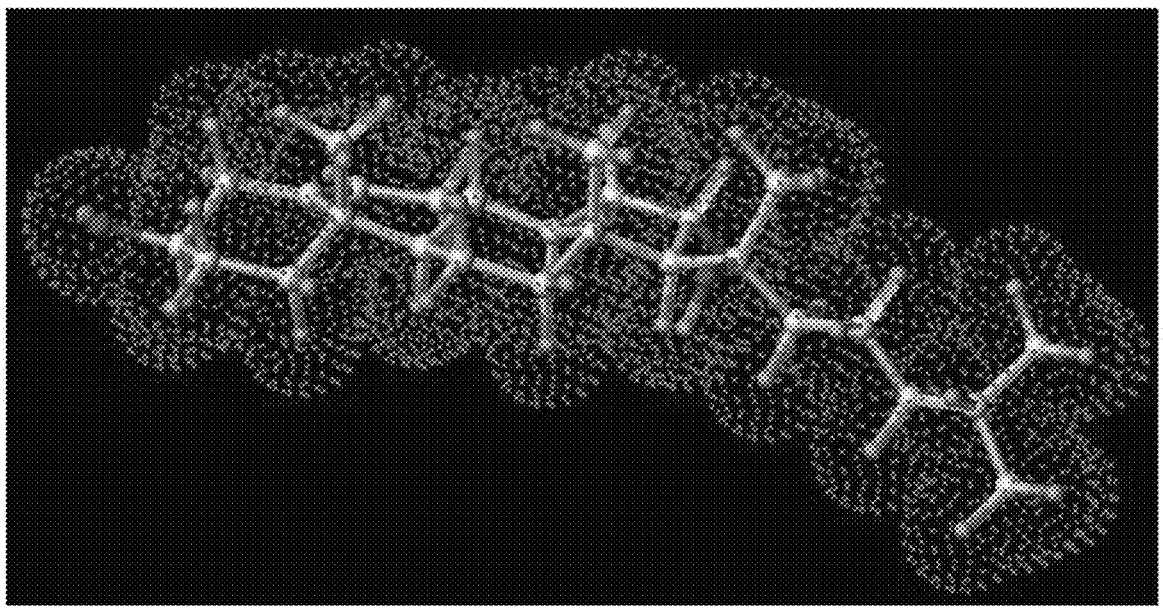
FIG. 39 is a dot surface model of 20A-Hydroxycholesterol.
Figure 40:
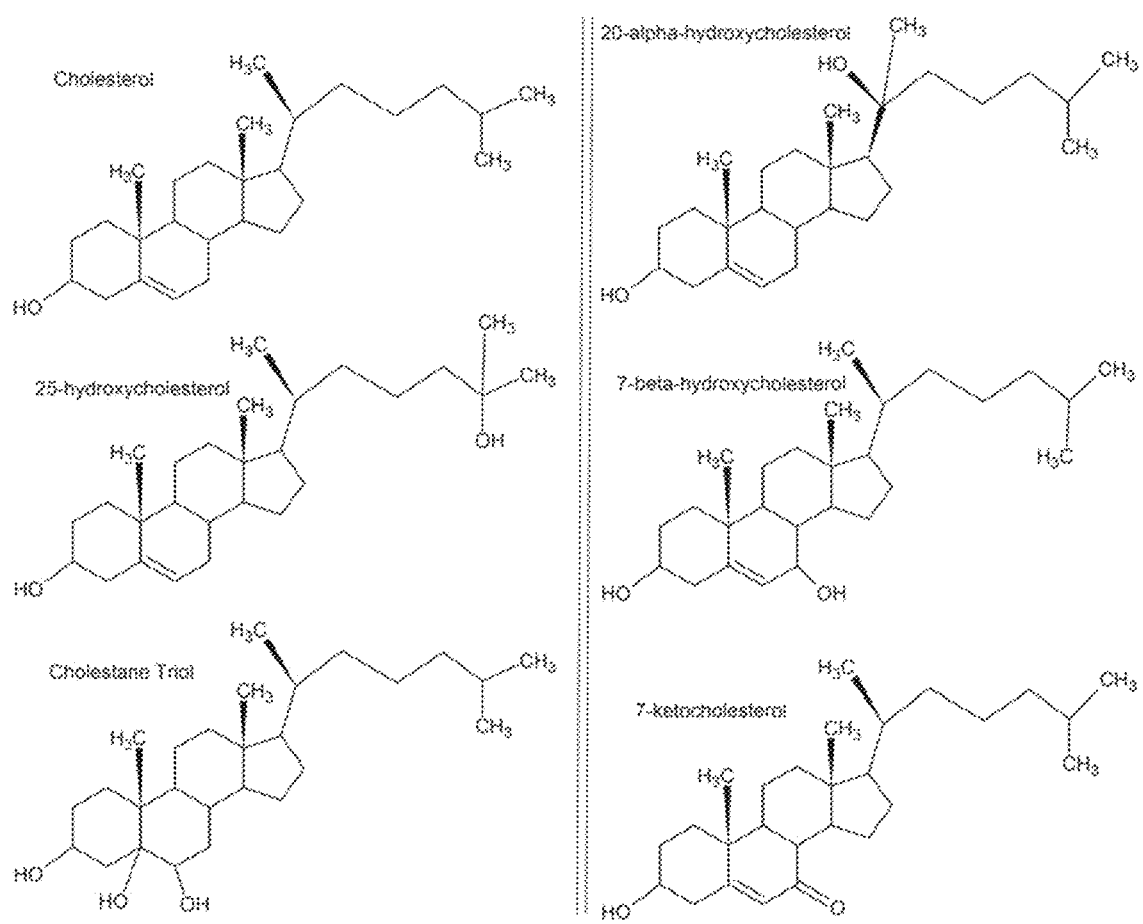
FIG. 40 shows line structures for Cholesterol and Selected Oxidized Derivatives.
Figure 41:
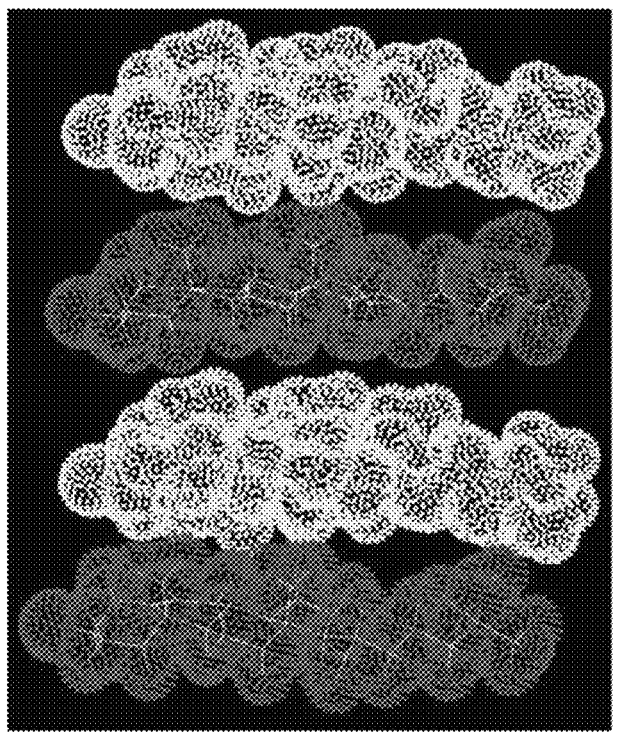
FIG. 41 shows the packing of Cholesterol and 25-Hydroxycholesterol.
Figure 42:
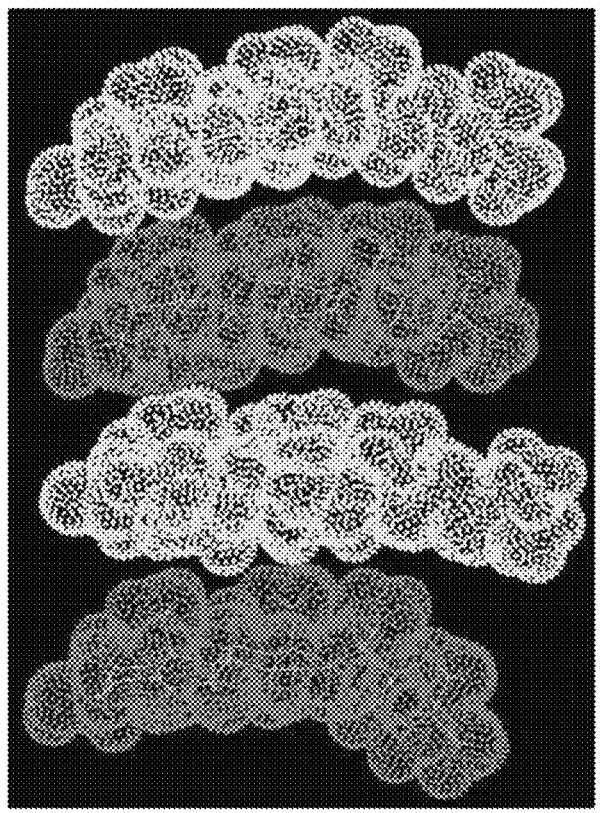
FIG. 42 shows the packing of Cholesterol and 7-Ketocholesterol.
Figure 43A:
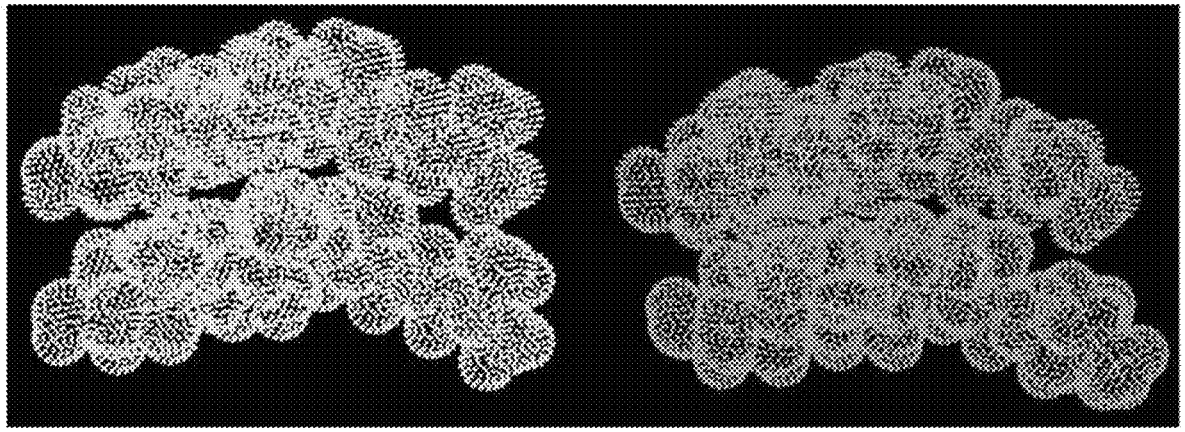
FIG. 43A shows the packing of Cholesterol and Cholestane Triol.
Figure 43B:
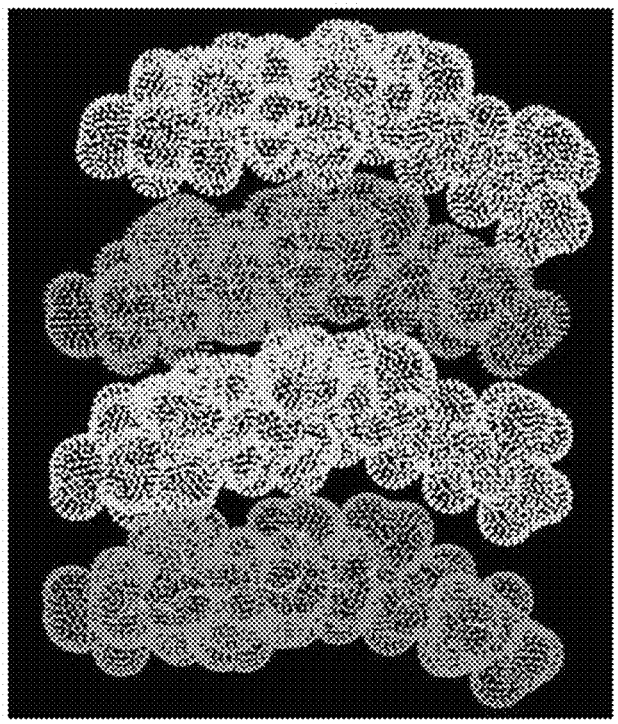
FIG. 43B shows an alternative packing of Cholesterol and Cholestane Triol.
Figure 44:
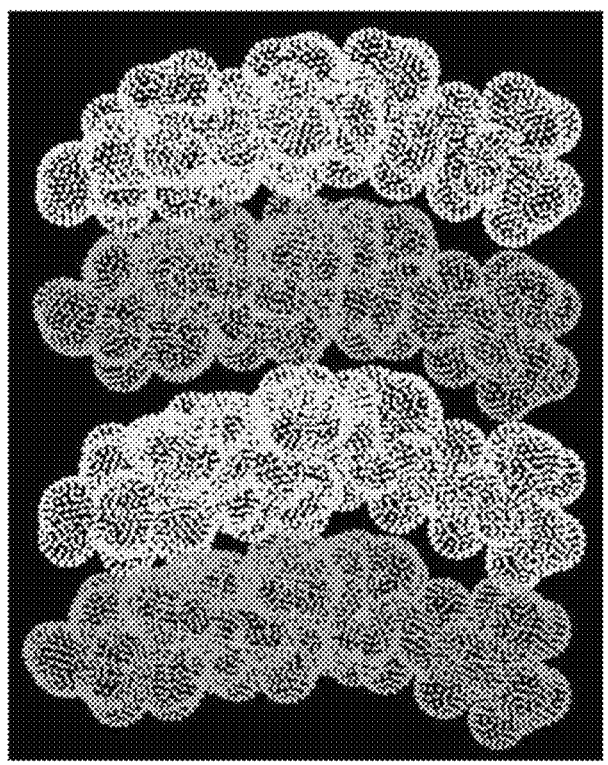
FIG. 44 shows the packing of Cholesterol and 20A-Hydroxycholesterol.
Figure 45:
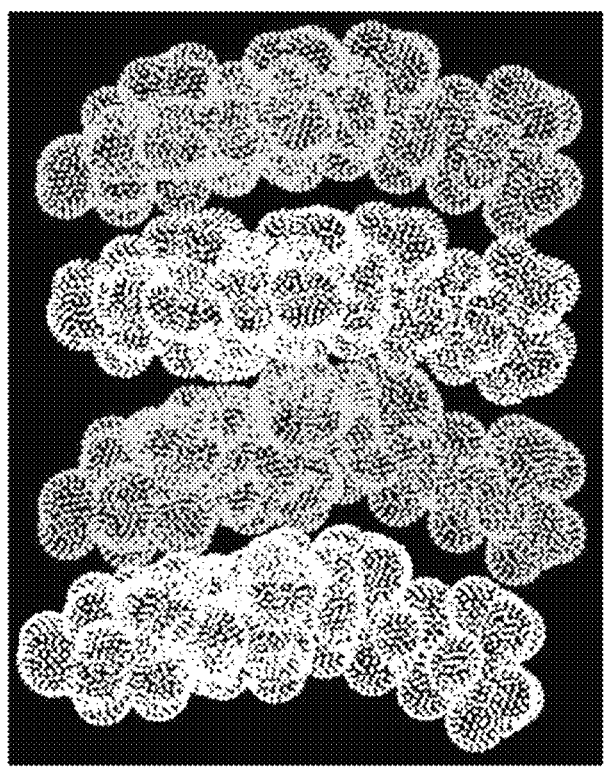
FIG. 45 shows the packing of Cholesterol and 7B-Hydroxycholesterol.
Figure 46:
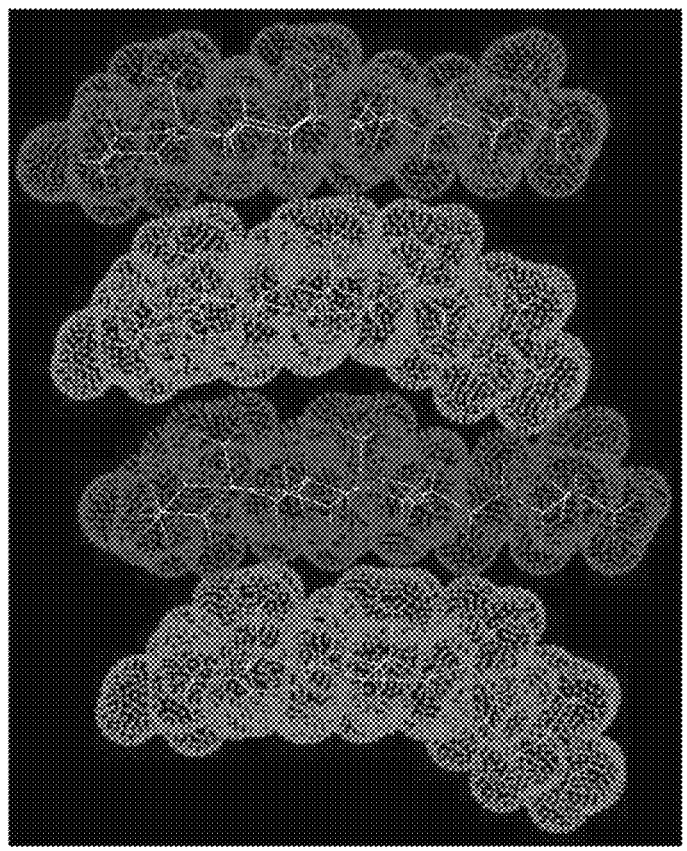
FIG. 46 shows the packing of 25-Hydroxycholesterol and 7-Ketocholesterol.
Figure 47:
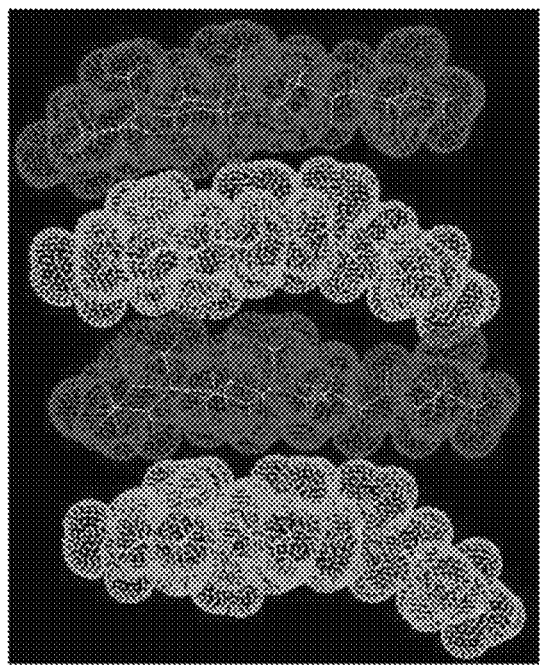
FIG. 47 shows the packing of 25-Hydroxycholesterol and Cholestane Triol.
Figure 48:
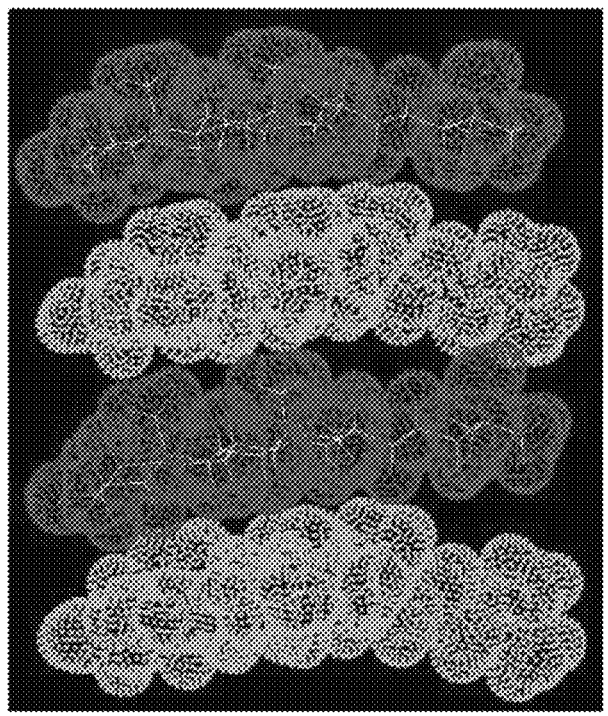
FIG. 48 shows the packing of 25-Hydroxycholesterol and 20A-Hydroxycholesterol.
Figure 49:
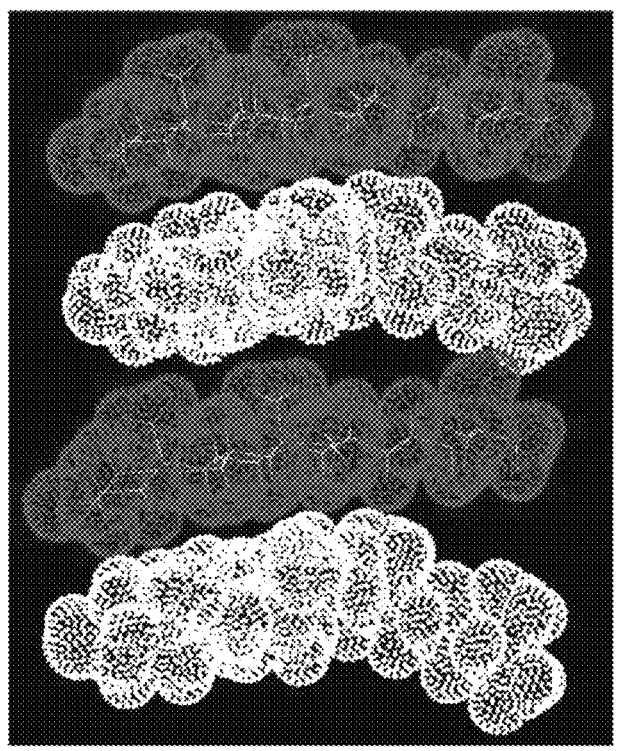
FIG. 49 shows the packing of 25-Hydroxycholesterol and 7B-Hydroxycholesterol.
Figure 50:
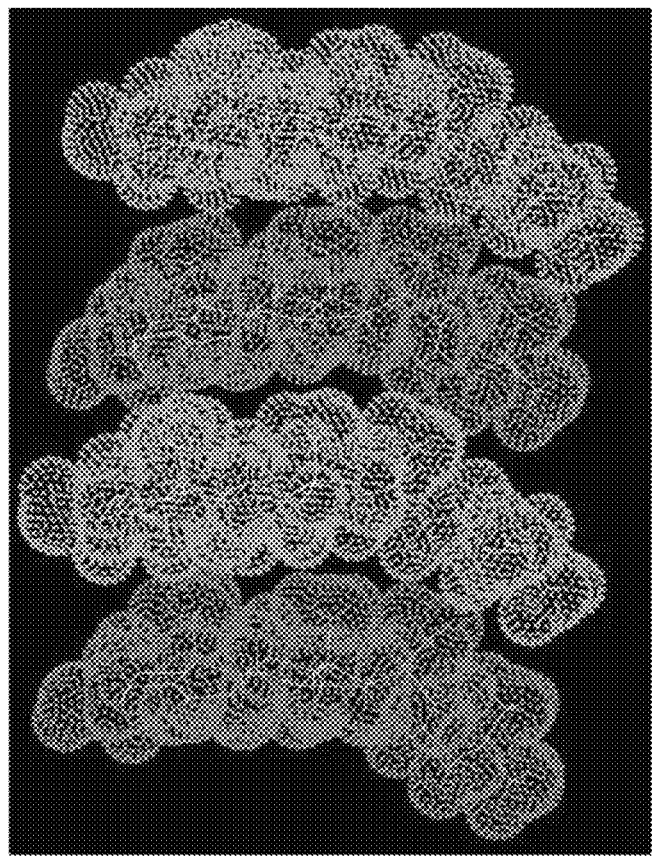
FIG. 50 shows the packing of Cholestane Triol and 7-Ketocholesterol.
Figure 51:
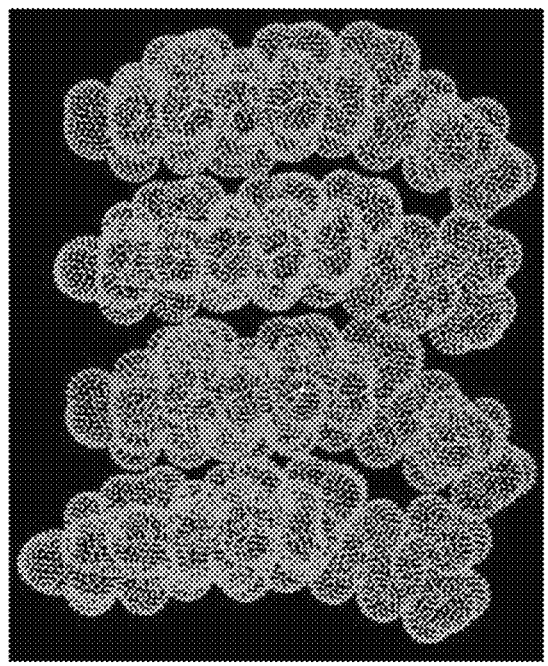
FIG. 51 shows the packing of Cholestane Triol and 20A-Hydroxycholesterol.
Figure 52:
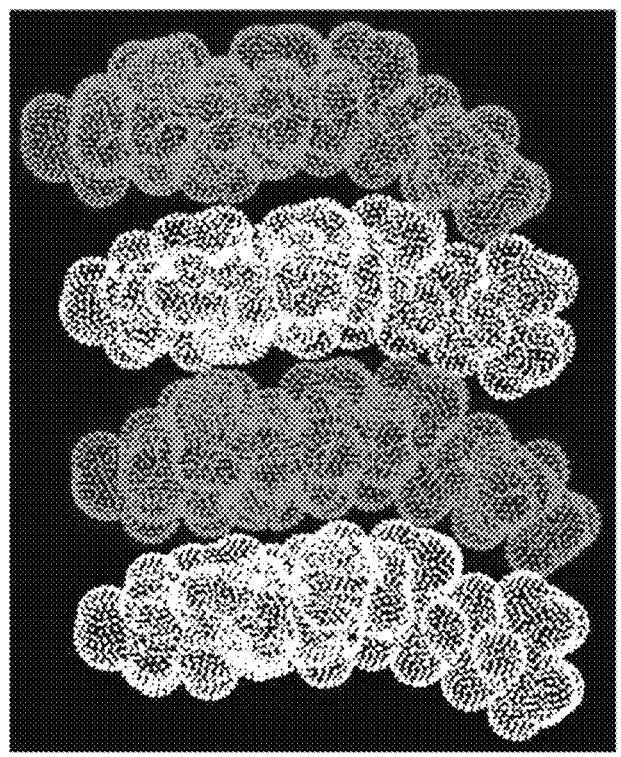
FIG. 52 shows the packing of Cholestane Triol and 7B-Hydroxycholesterol.
Figure 53:
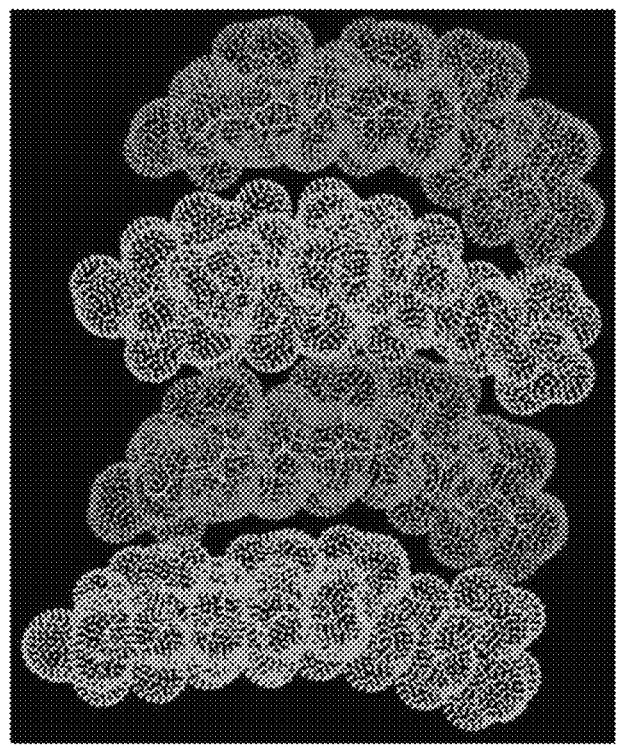
FIG. 53 shows the packing of 7-Ketocholesterol and 20A-Hydroxycholesterol.
Figure 54:
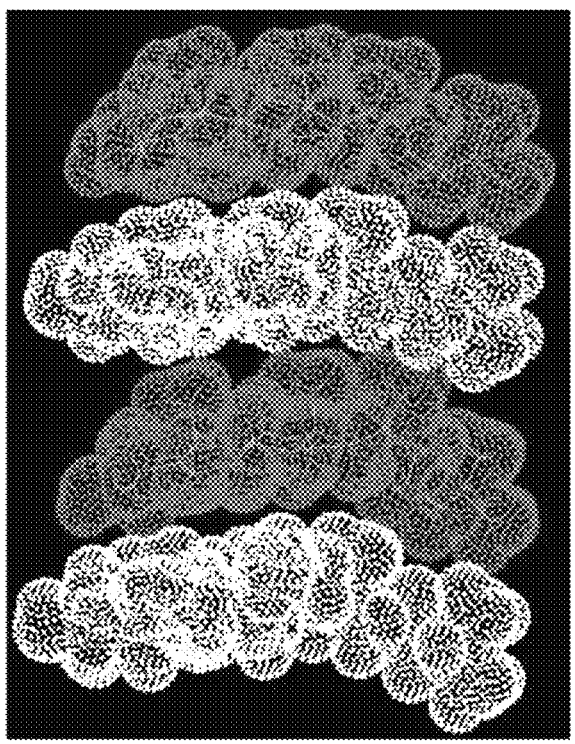
FIG. 54 shows the packing of 7-Ketocholesterol and 7B-Hydroxycholesterol.
Figure 55:
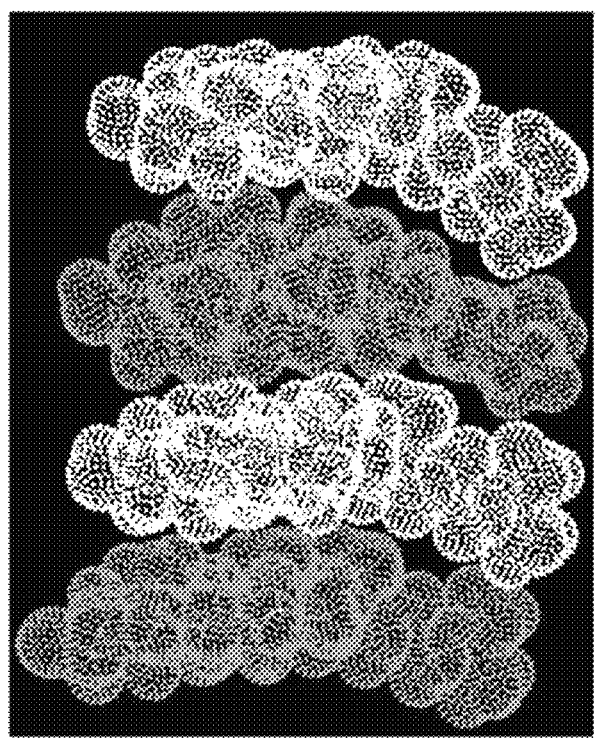
FIG. 55 shows the packing of 20A-Hydroxycholesterol and 7B-Hydroxycholesterol.
Figure 56:
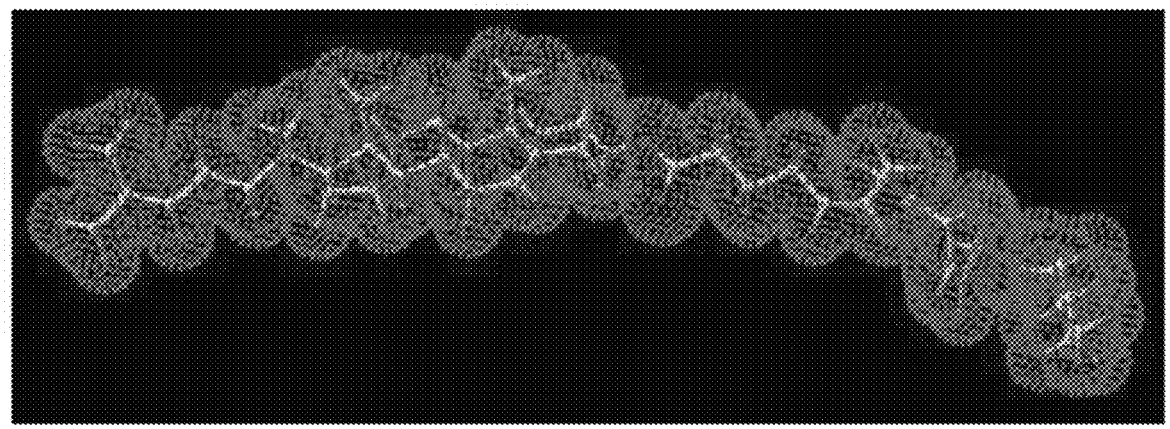
FIG. 56 is a dot surface model for Cholesteryl Arachidonate.
Figure 57:
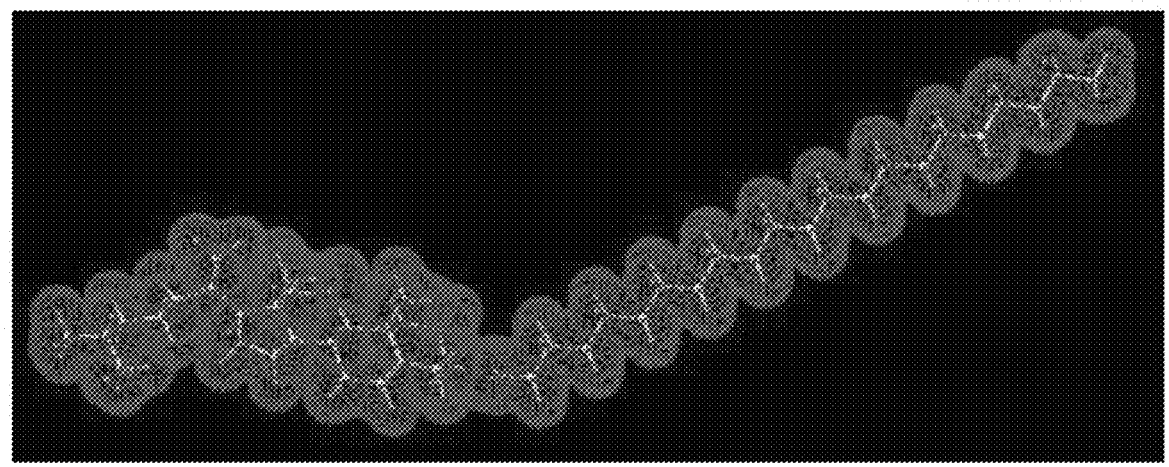
FIG. 57 is a dot surface model for Cholesteryl Behenate.
Figure 58:
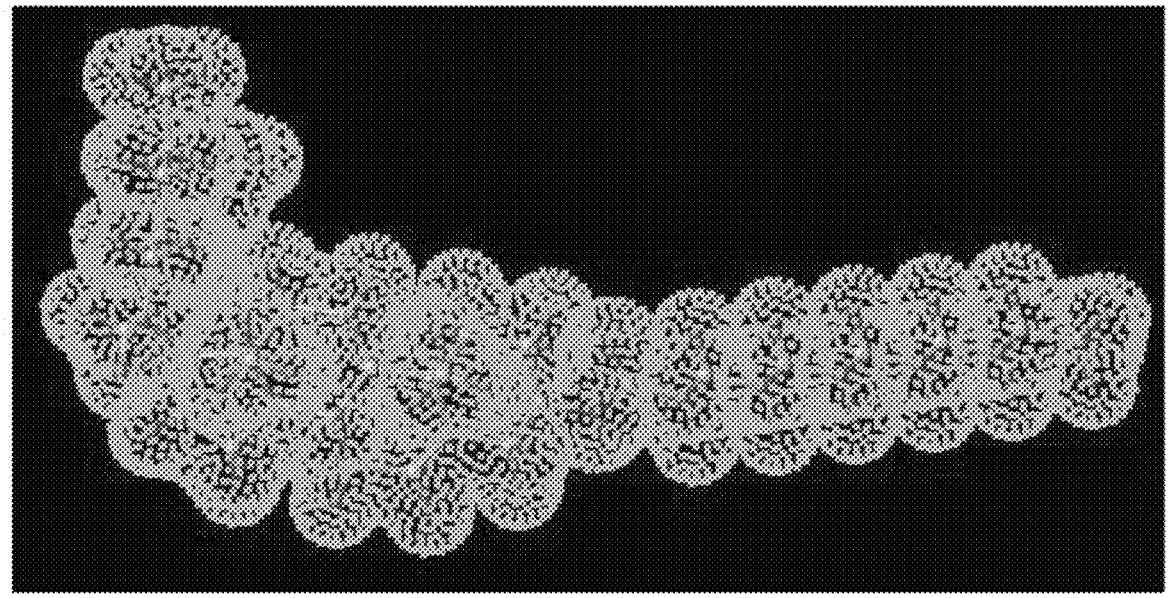
FIG. 58 is a dot surface model for Cholesteryl Dodecanoate (laurate)
Figure 59:
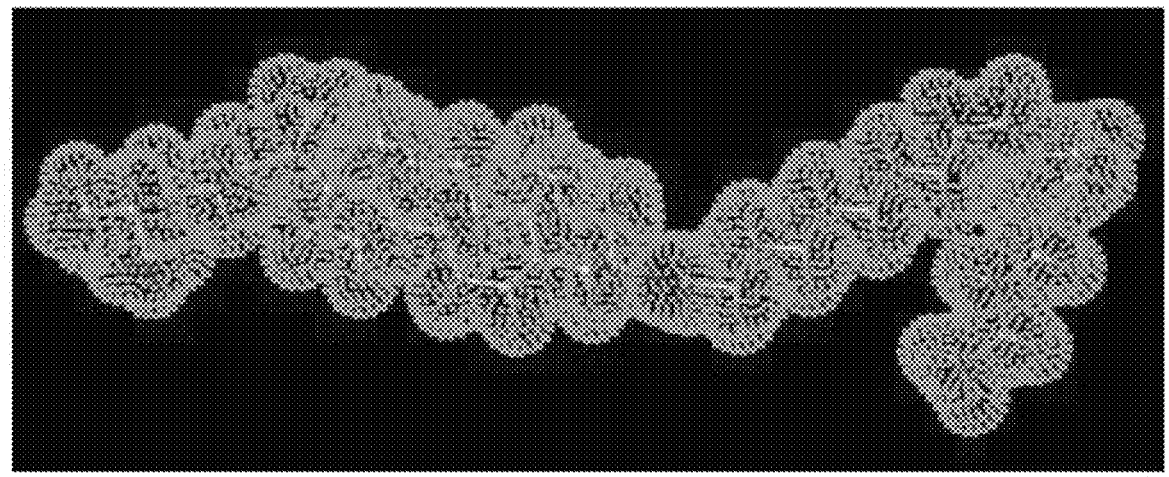
FIG. 59 is a dot surface model for Cholesteryl Linoleate.
Figure 60:
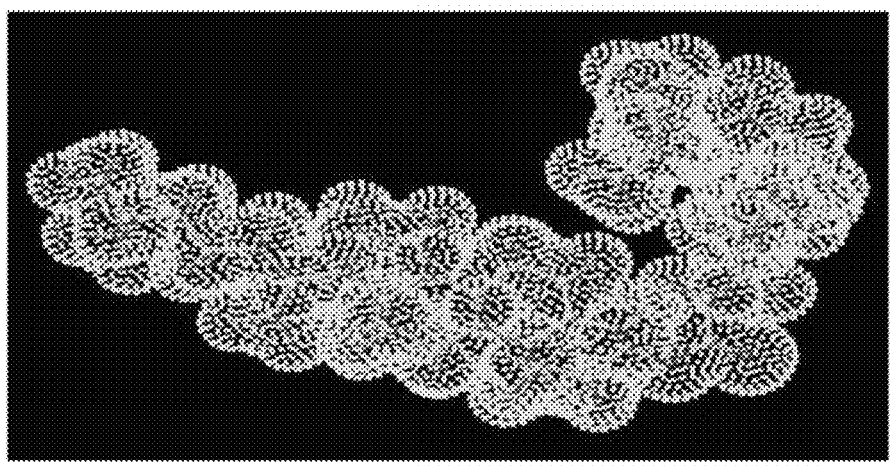
FIG. 60 is a dot surface model for Cholesteryl Linolenate.
Figure 61:
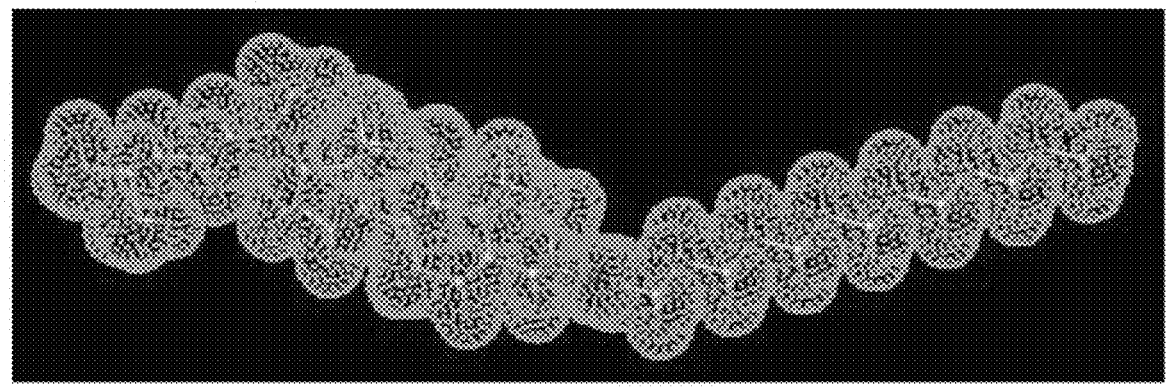
FIG. 61 is a dot surface model for Cholestetyl Myristate.
Figure 62:
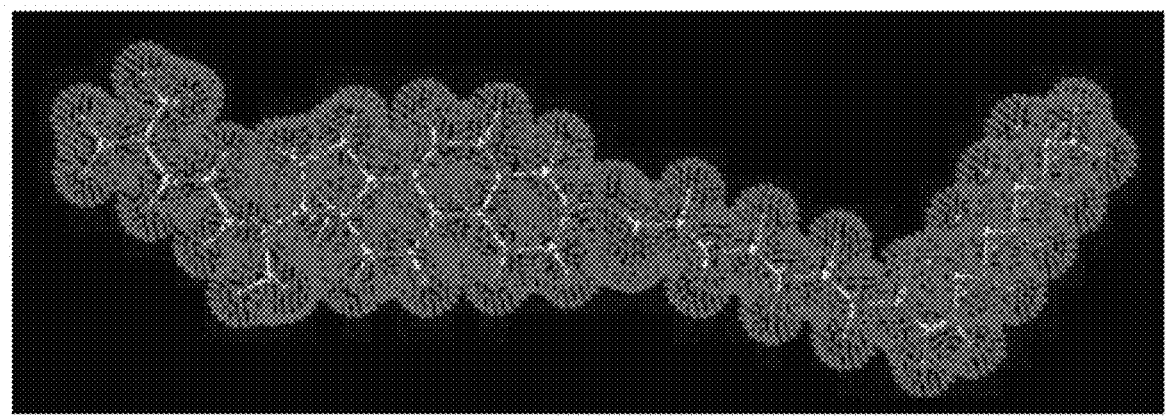
FIG. 62 is a dot surface model for Cholesteryl Oleate.

The phase diagrams for CS and CB in FIGS. 33A and 33B illustrate that at the extremes, the binary combinations tend to become co-soluble with each other. In the middle combinations, while they are not co-soluble, they are rather close to being co-soluble as the phase diagrams indicate by such a small distance between the two sets of data points.

The binary work with cholesteryl arachidonate (CA) was not pursued after several failed attempts occurred in re crystallization of the binary combinations. The melting point for CA is 24.73° C. according to Table 2 above. After the binary combinations of CA and cholesterol oleate (CO) were tried, it was found that there were no re-crystallization points from the DSC graphs. After re-heating the sample, there was no peak shown on the DSC graphs. Due to this, no further work was done with CA and the other unsaturated cholesteryl esters. However, there is the possibility for binary work with these cholesteryl esters if the capability to chill the samples in the DSC occurs. The ester tail of CA is in the cis-conformation, which is why the kinks form as opposed to more of a straight line that the trans-conformation would produce.

The binary work for cholesteryl linoleate (CL) showed that it was co-soluble with both CO and cholesteryl linolenate (CLn). CL contains two carbon-carbon double bonds in the fatty acid portion of the molecule, with bond of the double bonds being of the cis-conformation. Table 4 below shows the HDI of the ester in the fatty acid portion of the molecule. Due to this double bond, there are kinks that are developed and so the molecule can not pack as efficiently as if it had no carbon-carbon double bonds in the fatty acid tail as in the saturated cholesteryl esters. These two kinks that exist allow for empty voids to develop, reducing the packing ability of the molecule. The individual molecules for the different binary combinations studied here should pack together. The results that are shown in FIGS. 21A and 21B show that over all concentrations of the binary combinations of CO and CL are co-soluble. Note as well, the results for $T_s$ of the peak obtained from the DSC graphs lie very close to the ideal melt line for the samples. The binary work shows that for CL and CLn they are co-soluble over all concentrations, but do not lie on top of the ideal melt line. Here a negative deviation occurs, which suggests that the structures of the packed solid crystals are less stable than what would be predicted. This could be attributed, to more degrees of unsaturation present in the tail of CLn (3 C=C) than in CO (1 C=C).

The binary combinations for both CLn with CO (See FIGS. 22A and 22B) and CLn with CL (See FIGS. 21A and 21B) have phase diagrams that show they are co-soluble over all concentrations. Comparing the results obtained from the phase diagrams for CLn and CO we can see that the results are quite different than the phase diagrams for CLn and CL. The binary work with CO suggests that the structures of the packed crystal solids are more stable than that of CLn with CL. Comparing the structural differences between CL, CO, and CLn it can be seen that the main difference is in the number of C=C double bonds since otherwise the structures are the same. CLn contains 3 C=C of the cis-conformation, whereas CO contains only one C=C, of the cis-conformation in the fatty acid tail. One explanation for the ability of the two molecules to be more co-soluble with each other is that CO molecules have the ability to orient their tails in one direction due to the single carbon-carbon double bond, where as the CLn molecule can orient its tail in a different direction because of the 3 carbon-carbon double bonds. This void that would be created could then attribute to the reason that the binary system melts at a lower temperature due to the freedom of the tails of the esters to move around in that void.

CL and CLn both have the first two carbon-carbon double bonds in common, so the difference in packing structure may be attributed to the location of the third double bond for CLn being closer to the tail end, and thus affecting the crystal structure more. Due to this third C=C double bend being near the tail end, it may cause more open voids to be produced, which would lower the melting point, and can be seen by the phase diagrams for CL and CLn.

As can be seen in Table 3 below, CB has the longest fatty acid tail that was studied in binary combinations. Since CB has the longest tail, it possesses the problem of packing efficiently with the other saturated esters since there will be empty voids between the ends of the other tails and the end of the tail for CB. As the phase diagrams show for the binary combinations with CB, there is a lack of co-solubility with the other esters. This lack of co-solubility increases as you increase the difference in the number of methylene groups (—CH$_2$—) between the two components in the binary system. From this, it is predicted that the combinations of CB and CS are the most co-soluble with each other because they are the closest in fatty acid tail length, differing by only four methylene groups.

As is shown in the phase diagrams, the relationship between decreasing co-solubility and increasing the difference in the number of methylene groups between the two molecules holds for the entire series of CB. From the phase diagrams, it is also shown that the mole fractions of the CB in the system determined how closely the two compounds are to being co-soluble. The phase diagrams show that as you move from the mid MF range towards the extremes, the co-solubility increases. One explanation for observing only one set of melting points at the extremes of the phase diagrams could be due to the crystal structure tolerating the small amount of impurities, which would be the other cholesteryl ester in the particular binary combination.

As can be seen in Table 3 below, CD is the cholesteryl ester that contains the shortest fatty acid tail out of the group of saturated cholesteryl esters. Theoretical predictions would say that CD should be most co-soluble with other cholesteryl esters that are relatively close in size and structure as those of CD. From this, the series should go from most likely to be co-soluble to least likely to be co-soluble in the following order: CM>CP>CS>CB. This was constructed by looking at the differences in the length of the fatty acid tails. Our experimental predictions show that for the most pan our predicted trend is very close to the experimental results. Looking at individual phase diagrams, there are mole fractions that are more co-soluble than others, as can be seen in FIG. 27A. The differences in the tail length, which range from 2 to 10 methylene units for the CM and CB respectively, are what cause the lack of co-solubility. When you increase the number of methylene groups in the tail length relative to the other component, you introduce empty voids that can not be efficiently packed in the crystal structure.

Cholesteryl Myristate contains the second shortest fatty acid tail at 14 carbons, as seen in Table 3 below. As was discussed in the comments on CD, the binary combinations of CM with CD or CM with CP should be the most co-soluble since they only differ in tail length by 2 methylene groups. The phase diagrams do show that while they are not co-soluble with each other, they are closest to these two binary combinations. Comparing the other results of CM it can be seen that there is a relationship between increasing the difference in methylene groups and decrease in lack of co-solubility. This is just the opposite trend that was discussed in the previous section on CD. Experimental results show that in going from the largest difference to the smallest difference in the lack of co-solubility the following series is obtained: CP>CD>CS>CB. These results indicate that there is another factor aside from difference in methylene groups that is affecting this series.

Cholesteryl Palmitate contains 16 carbons in the fatty acid tail as shown in Table 3 below. Continuing the trend for the saturated cholesteryl esters, it is not entirely co-soluble with any other saturated cholesteryl esters that were studied. From the phase diagrams, the co-solubility for CP with the other esters runs from closest to being co-soluble to least co-soluble in the following series: CB>CS>CM>CD. The experimental series shows that the phase diagrams for the binary combinations of CP with CB (See FIGS. 32A and 32B) are the most co-soluble, where there is very little of the solid-liquid state as compared to the results for CP with CD (See FIGS. 25A and 25B). In the phase diagrams for CP and CD it is shown that there is a rather large solid-liquid phase that exists. These results run contrary to the theoretical predictions that would have the series of co-solubility being more along the following line: CM=CS>CD>CB, where CM and CS have the same difference in methylene groups so they are expected to produce results that would be similar to each other. The theoretical results predict that binary systems of CP with CB would be the least co-soluble since they have the largest difference in methylene units at 6 units.

Cholesteryl Stearate contains 18 carbons in the fatty acid tail of the cholesteryl ester. The different binary combinations for CS were able to produce differences in the number of methylene groups ranging from 2, 4, or 6 unit differences for CP, CM and CB, CD respectively. The difference in the packing structures from the tail lengths has the ability to contribute to the lack of co-solubility with the other saturated cholesteryl esters.

TABLE 3

Saturated Cholesteryl Esters' Intrinsic Properties

| Saturated Cholesteryl Ester | Carbon Tail Length | Formula |
|---|---|---|
| Cholesteryl Behenate | 22 | $C_{49}H_{88}O_2$ |
| Cholersteryl Dodecanoate (laurate) | 12 | $C_{39}H_{68}O_2$ |
| Cholesteryl Myristate | 14 | $C_{41}H_{72}O_2$ |
| Cholesteryl Palmitate | 16 | $C_{43}H_{76}O_2$ |
| Cholesteryl Stearate | 18 | $C_{45}H_{80}O_2$ |

The data in Table 4 below is, for the unsaturated cholesteryl esters. This data represents the degrees of unsaturation that an present in the fatty acid chain tail of the ester. The HDI of the tail is the Hydrogen Deficiency Index, which tells how many degrees of unsaturation there is in a chemical formula. The HDI was calculated by the following formula:

$$HDI = \frac{(2n+2) - (H)}{2}$$

n=number of carbons in the chemical formula

H=number of Hydrogens in the formula

This formula produced the HDI for the unsaturated cholesteryl esters. The number of carbons and hydrogens used were only for the fatty acid tail portion of the cholesteryl ester. In Table 4, there are two numbers separated by a semi-colon. This represents the number of C=C bonds and then also the number of C=O bonds in the tail of the fatty acid.

Table 5 below shows the difference in the tail length in terms of methylene units between the different binary combinations. Based on those differences, a theoretical ranking was developed that looked at the differences in methylene units only as the predictor for co-solubility. The binary combinations indicated in red are the ones that do not seem to fit in using the results of the experiments performed. For those predictions, another pan of the system would need to be taken into consideration. It has been suggested that two other possible considerations are crystal structures of the pure components and the second being the enantiotropic or monotropic behavior of individual components.

TABLE 4

Unsaturated Cholesteryl Esters' Intrinsic Properties

| Unsaturated Cholesteryl Ester | Carbon Tail Length | HDI of Tail C=C; C=O | Formula |
|---|---|---|---|
| Cholesteryl Arachidonate | 20 | 4; 1 | $C_{47}H_{76}O_2$ |
| Cholesteryl Linoleate | 18 | 2; 1 | $C_{45}H_{76}O_2$ |
| Cholesteryl Linolenate | 18 | 3; 1 | $C_{45}H_{74}O_2$ |
| Cholesteryl Oleate | 18 | 1; 1 | $C_{45}H_{78}O_2$ |

TABLE 5

Theory Predictions of Co-solubility for Saturated Cholesteryl Esters

| | Binary System | Tail Length Difference |
|---|---|---|
| Most Co-soluble | CD/CM | 2 |
| | CM/CP | 2 |
| | CP/CS | 2 |
| | CD/CP | 4 |
| | CM/CS | 4 |
| | CS/CB | 4 |
| | CD/CS | 6 |
| | CP/CB | 6 |
| | CM/CB | 8 |
| Least Co-soluble | CD/CB | 10 |

While all this research has produced a large volume of data which has been analyzed, there is still more research that can be done concerning the area of atherosclerotic plaque. First, the development of non-invasive procedures as a determination of overall arterial health is one goal of the future research. In order to reach that, there needs to be more done in studying simpler systems before moving on to study the complicated systems of atherosclerotic plaque. Future research will need to cover more DSC studies of binary, tertiary, and higher systems. Also, use of the 2-D NMR and molecular modeling program, SYBYL®, will be valuable in working hand-in-hand to develop the understanding of the complex atherosclerotic plaque systems.

A DSC study of binary systems such as unsaturated cholesteryl esters in combination with saturated cholesteryl esters is one possible starting point. Also, DSC studies of binary combinations of cholesterol, which is freely found in the body with the esters and then creating phase diagrams for them is one direction to examine. From there, the ground work will have been laid, and studies of tertiary systems can be carried out where the examination of combinations of cholesterol, oxidized cholesterol, and the cholesteryl esters can be studied in differing compositions to observe what differences and what similarities they have in common with the binary systems. Once the phase diagrams for the binary and tertiary systems are developed, an understanding of how molecules interact with each other in the packing system can be obtained. With the understanding gained from this foundation work, studies of complex systems of atherosclerotic plaque can begin with the DSC to see what thermodynamic information can be obtained.

Due to the complexity of atherosclerotic plaque, there exists the ability to do experimental work along with the possibility to per theoretic computational work. The experimental aspect would involve the use of the DSC as mentioned above in studying thermodynamic properties of the plaque. Use of the 2-D NMR would allow for structural determinations of the plaque as well. From the data, correlations between packing structure of the plaque and disease prediction could be developed. Computational research can be done that would develop molecular models that conform to the experimental data that is collected. With that correlation between experimental and computational work being completed, a methodology can be created to better predict atherosclerotic plaque disease without the need of invasive procedures.

FIG. 57 through 62 are the dot surface representations of cholesterol and the oxidized sterols. FIG. 63 is the molecular bond graphs for the cholesterol and oxidized sterols. Possible packing structures for cholesterol and the oxidized sterols are shown in FIGS. 64 through 78.

FIG. 79 is the dot surface representation for the cholesteryl esters.

TABLE 6

Data Points for the Pure Oxidized Cholesterol

| File Name | $T_o$ (° C.) | $T_s$ (° C.) | $T_f$ (° C.) | MF A | Sample Size (mg) |
|---|---|---|---|---|---|
| Cholesterol-runDDA | 147.10 | 149.12 | 151.44 | Cholesterol | 3.0 |
| 25-Hydroxy-smallpan-runDDd | 180.29 | 183.88 | 185.58 | 25-OH | 1.9 |
| 7-keto-runDDe | 168.38 | 171.58 | 173.60 | 7-Keto | 3.4 |
| Cholestane | 238.33 | 241.99 | 243.83 | CT | 4.1 |
| 20-alpha-cholesterol-slowerRun-DDg2 | 111.57 | 118.22 | 123.45 | 20A | 0.5 |
| 7-beta-cholesterol-runDDk | 149.79 | 156.14 | 157.82 | 7B | 1.0 |

TABLE 7

Mole Fraction Break Downs for Oxidized Cholesterols

| MF A | MF B | A = | B = | Mass A (mg) | Mass B (mg) | Total Mass (mg) |
|---|---|---|---|---|---|---|
| 0.595 | 0.405 | Cholesterol | 25-OH | 3.1 | 2.2 | 5.3 |
| 0.757 | 0.243 | Cholesterol | 25-OH | 4.5 | 1.5 | 6.0 |
| 0.273 | 0.727 | Cholesterol | 25-OH | 0.9 | 2.5 | 3.4 |
| 0.699 | 0.301 | Cholesterol | 25-OH | 2.9 | 1.3 | 4.2 |
| 0.536 | 0.464 | Cholesterol | 25-OH | 3.1 | 2.8 | 5.9 |
| 0.837 | 0.163 | Cholesterol | 7-Keto | 17.8 | 3.6 | 21.4 |
| 0.138 | 0.862 | Cholesterol | 7-Keto | 3.6 | 23.3 | 26.9 |
| 0.340 | 0.660 | Cholesterol | 7-Keto | 1.9 | 3.8 | 5.7 |
| 0.419 | 0.581 | Cholesterol | 7-Keto | 1.6 | 2.3 | 3.9 |
| 0.377 | 0.623 | Cholesterol | 7-Keto | 2.1 | 3.6 | 5.7 |
| 0.662 | 0.338 | Cholesterol | 7-Keto | 3.6 | 1.9 | 5.5 |
| 0.773 | 0.227 | Cholesterol | 7-Keto | 13.2 | 4.0 | 17.2 |
| 0.228 | 0.772 | Cholesterol | 7-Keto | 5.3 | 18.6 | 23.9 |
| 0.339 | 0.661 | Cholesterol | 7-Keto | 4.8 | 9.7 | 14.5 |
| 0.500 | 0.500 | Cholesterol | Triol | 4.5 | 4.9 | 9.4 |
| 0.457 | 0.543 | Cholesterol | Triol | 4.1 | 5.3 | 9.4 |
| 0.543 | 0.457 | Cholesterol | Triol | 5.8 | 5.3 | 11.1 |
| 0.312 | 0.688 | Cholesterol | Triol | 3.8 | 9.1 | 12.9 |
| 0.742 | 0.258 | Cholesterol | Triol | 3.7 | 1.4 | 5.1 |
| 0.396 | 0.604 | Cholesterol | Triol | 5.3 | 8.8 | 14.1 |
| 0.144 | 0.856 | Cholesterol | Triol | 1.3 | 8.4 | 9.7 |
| 0.158 | 0.842 | Cholesterol | Triol | 2.5 | 14.5 | 17.0 |
| 0.286 | 0.714 | Cholesterol | 20A | 1.0 | 2.6 | 3.6 |
| 0.496 | 0.504 | Cholesterol | 20A | 1.7 | 1.8 | 3.5 |
| 0.732 | 0.268 | Cholesterol | 20A | 2.1 | 0.8 | 2.9 |
| 0.447 | 0.553 | Cholesterol | 20A | 0.7 | 0.9 | 1.6 |
| 0.454 | 0.546 | Cholesterol | 20A | 1.2 | 1.5 | 2.7 |
| 0.610 | 0.390 | Cholesterol | 20A | 1.5 | 1.0 | 2.5 |
| 0.525 | 0.475 | Cholesterol | 7B | 1.7 | 1.6 | 3.3 |
| 0.748 | 0.252 | Cholesterol | 7B | 2.0 | 0.7 | 2.7 |
| 0.316 | 0.684 | Cholesterol | 7B | 0.8 | 1.8 | 2.6 |
| 0.537 | 0.463 | 25OH | Triol | 1.0 | 0.9 | 1.9 |
| 0.284 | 0.716 | 25OH | Triol | 1.1 | 2.9 | 4.0 |
| 0.752 | 0.248 | 25OH | Triol | 3.2 | 1.1 | 4.3 |
| 0.654 | 0.346 | 25OH | 7-Keto | 3.6 | 1.9 | 5.5 |
| 0.228 | 0.772 | 25OH | 7-Keto | 1.1 | 3.7 | 4.8 |

TABLE 7-continued

Mole Fraction Break Downs for Oxidized Cholesterols

| MF A | MF B | A = | B = | Mass A (mg) | Mass B (mg) | Total Mass (mg) |
|---|---|---|---|---|---|---|
| 0.481 | 0.519 | 25OH | 7-Keto | 2.7 | 2.9 | 5.6 |
| 0.140 | 0.860 | 25OH | 7-Keto | 2.1 | 12.8 | 14.9 |
| 0.608 | 0.392 | 25OH | 7-Keto | 5.3 | 3.4 | 8.7 |
| 0.517 | 0.483 | 25OH | 20A | 1.5 | 1.4 | 2.9 |
| 0.250 | 0.750 | 25OH | 20A | 0.2 | 0.6 | 0.8 |
| 0.733 | 0.267 | 25OH | 20A | 1.1 | 0.4 | 1.5 |
| 0.467 | 0.533 | 25OH | 7B | 0.7 | 0.8 | 1.5 |
| 0.655 | 0.345 | 25OH | 7B | 3.8 | 2.0 | 5.8 |
| 0.154 | 0.846 | 25OH | 7B | 0.4 | 2.2 | 2.6 |
| 0.773 | 0.227 | 25OH | 7B | 5.8 | 1.7 | 7.5 |
| 0.217 | 0.783 | 25OH | 7B | 1.0 | 3.6 | 4.6 |
| 0.802 | 0.198 | 7-Keto | Triol | 10.0 | 2.6 | 12.6 |
| 0.312 | 0.688 | 7-Keto | Triol | 2.5 | 5.8 | 8.3 |
| 0.512 | 0.488 | 7-Keto | Triol | 1.9 | 1.9 | 3.8 |
| 0.247 | 0.753 | 7-Keto | Triol | 1.5 | 4.8 | 6.3 |
| 0.489 | 0.511 | Triol | 20A | 1.3 | 1.3 | 2.6 |
| 0.761 | 0.239 | Triol | 20A | 1.0 | 0.3 | 1.3 |
| 0.390 | 0.610 | Triol | 20A | 0.6 | 0.9 | 1.5 |
| 0.242 | 0.758 | Triol | 20A | 0.6 | 1.8 | 2.4 |
| 0.291 | 0.709 | Triol | 7B | 0.9 | 2.1 | 3.0 |
| 0.489 | 0.511 | Triol | 7B | 1.8 | 1.8 | 3.6 |
| 0.870 | 0.130 | Triol | 7B | 2.1 | 0.3 | 2.4 |
| 0.489 | 0.511 | Triol | 7B | 1.1 | 1.1 | 2.2 |
| 0.642 | 0.358 | Triol | 7B | 3.0 | 1.6 | 4.6 |
| 0.463 | 0.537 | 7-Keto | 20A | 1.7 | 0.5 | 2.2 |
| 0.728 | 0.272 | 7-Keto | 20A | 0.8 | 0.3 | 1.1 |
| 0.228 | 0.772 | 7-Keto | 20A | 0.6 | 0.7 | 1.3 |
| 0.307 | 0.693 | 7-Keto | 20A | 1.5 | 3.4 | 4.9 |
| 0.201 | 0.799 | 7-Keto | 7B | 0.2 | 0.8 | 1.0 |
| 0.728 | 0.272 | 7-Keto | 7B | 1.6 | 0.6 | 2.2 |
| 0.501 | 0.499 | 7-Keto | 7B | 0.6 | 0.6 | 1.2 |
| 0.334 | 0.666 | 7-Keto | 7B | 1.6 | 3.2 | 4.8 |
| 0.300 | 0.700 | 20A | 7B | 0.6 | 1.4 | 2.0 |
| 0.429 | 0.571 | 20A | 7B | 0.9 | 1.2 | 2.1 |
| 0.519 | 0.481 | 20A | 7B | 1.4 | 1.3 | 2.7 |
| 0.733 | 0.267 | 20A | 7B | 1.1 | 0.4 | 1.5 |
| 0.480 | 0.520 | 20A | 7B | 1.2 | 1.3 | 2.5 |

TABLE 8

Mole Fraction Break Down for the Saturated Cholesteryl Esters

Saturated Cholesteryl Esters

| MF A | MF B | A = | B = | Mass A (mg) | Mass B (mg) | Total Mass (mg) |
|---|---|---|---|---|---|---|
| 0.778 | 0.222 | Laurate | Myristate | 15.4 | 4.6 | 20.0 |
| 0.384 | 0.616 | Laurate | Myristate | 7.9 | 13.3 | 21.2 |
| 0.485 | 0.515 | Laurate | Myristate | 4.4 | 4.9 | 9.3 |
| 0.319 | 0.681 | Laurate | Palmitate | 3.5 | 8.2 | 11.7 |
| 0.890 | 0.110 | Laurate | Palmitate | 8.8 | 1.2 | 10.0 |
| 0.532 | 0.468 | Laurate | Palmitate | 12.5 | 12.1 | 24.6 |
| 0.627 | 0.373 | Laurate | Stearate | 8.5 | 5.8 | 14.3 |
| 0.565 | 0.435 | Laurate | Stearate | 11.1 | 9.8 | 20.9 |
| 0.357 | 0.643 | Laurate | Stearate | 2.8 | 5.8 | 8.6 |
| 0.287 | 0.713 | Laurate | Behenate | 3.0 | 9.3 | 12.3 |
| 0.517 | 0.483 | Laurate | Behenate | 1.2 | 1.4 | 2.6 |
| 0.701 | 0.299 | Laurate | Behenate | 3.2 | 1.7 | 4.9 |
| 0.635 | 0.365 | Myristate | Palmitate | 7.3 | 4.4 | 11.7 |
| 0.401 | 0.599 | Myristate | Palmitate | 4.1 | 6.4 | 10.5 |
| 0.511 | 0.489 | Myristate | Palmitate | 6.2 | 6.2 | 12.4 |
| 0.663 | 0.337 | Myristate | Stearate | 7.9 | 4.4 | 12.3 |
| 0.515 | 0.485 | Myristate | Stearate | 3.1 | 3.2 | 6.3 |
| 0.315 | 0.685 | Myristate | Stearate | 2.1 | 5.0 | 7.1 |
| 0.739 | 0.261 | Myristate | Stearate | 4.4 | 1.7 | 6.1 |
| 0.497 | 0.503 | Myristate | Behenate | 1.5 | 1.8 | 3.3 |
| 0.304 | 0.696 | Myristate | Behenate | 1.4 | 3.8 | 5.2 |
| 0.817 | 0.183 | Myristate | Behenate | 6.0 | 1.6 | 7.6 |
| 0.317 | 0.683 | Palmitate | Stearate | 4.0 | 9.0 | 13.0 |
| 0.819 | 0.181 | Palmitate | Stearate | 15.6 | 3.6 | 19.2 |

TABLE 8-continued

Mole Fraction Break Down for the Saturated Cholesteryl Esters

Saturated Cholesteryl Esters

| MF A | MF B | A = | B = | Mass A (mg) | Mass B (mg) | Total Mass (mg) |
|---|---|---|---|---|---|---|
| 0.521 | 0.479 | Palmitate | Stearate | 5.0 | 4.8 | 9.8 |
| 0.709 | 0.291 | Palmitate | Behenate | 4.5 | 2.1 | 6.6 |
| 0.330 | 0.670 | Palmitate | Behenate | 2.0 | 4.6 | 6.6 |
| 0.482 | 0.518 | Palmitate | Behenate | 4.1 | 5.0 | 9.1 |
| 0.389 | 0.611 | Stearate | Behenate | 3.4 | 5.8 | 9.2 |
| 0.521 | 0.479 | Stearate | Behenate | 2.5 | 2.5 | 5.0 |
| 0.847 | 0.153 | Stearate | Behenate | 5.6 | 1.1 | 6.7 |

TABLE 9

Mole Fraction Break Down for Unsaturated Cholesteryl Esters

Unsaturated Cholesteryl Esters

| MF A | MF B | A = | B = | Mass A (mg) | Mass B (mg) | Total Mass (mg) |
|---|---|---|---|---|---|---|
| 0.635 | 0.365 | Oleate | Linoleate | 15.5 | 8.9 | 24.4 |
| 0.487 | 0.513 | Oleate | Linoleate | 7.9 | 8.3 | 16.2 |
| 0.261 | 0.739 | Oleate | Linoleate | 5.0 | 14.1 | 19.1 |
| 0.763 | 0.237 | Oleate | Linolenate | 14.6 | 4.5 | 19.1 |
| 0.502 | 0.498 | Oleate | Linolenate | 7.6 | 7.5 | 15.1 |
| 0.247 | 0.753 | Oleate | Linolenate | 6.6 | 20.0 | 26.6 |
| 0.796 | 0.204 | Linoleate | Linolenate | 14.9 | 3.8 | 18.7 |
| 0.493 | 0.507 | Linoleate | Linolenate | 8.0 | 8.2 | 16.2 |
| 0.340 | 0.660 | Linoleate | Linolenate | 8.1 | 15.7 | 23.8 |

TABLE 10

Sample Masses for the Pure Cholesteryl Esters

| $T_o$ (° C.) | $T_s$ (° C.) | $T_f$ (° C.) | Cholesteryl Esters MF A | Sample Size (mg) |
|---|---|---|---|---|
| 21.48 | 24.73 | 26.48 | Arachidonate | 11.3 |
| 88.95 | 90.19 | 92.10 | Behenate | 3.8 |
| 92.63 | 94.31 | 95.87 | Laurate | 7.5 |
| 42.17 | 43.82 | 45.68 | Linoleate | 3.8 |
| 35.98 | 38.40 | 40.14 | Linolenate | 9.9 |
| 70.97 | 71.89 | 73.60 | Myristate | 4.4 |
| 48.37 | 50.85 | 52.83 | Oleate | 7.6 |
| 78.02 | 79.11 | 80.47 | Palmitate | 1.8 |
| 82.55 | 84.13 | 86.05 | Stearate | 2.0 |

The Differential Scanning calorimeter (DSC) was used to obtain the data points that created the phase diagrams. The Pyris 6 DSC from Perkin Elmer that was used has the ability to study the thermal properties of samples that can range from 15° C. to 450° C. The instrument can heat, cool, or hold a sample at a specific temperature of the users choosing. The heating and cooling rates range from 0.1° C./minute to 100.0° C./minute depending on what is desired.

The four main components of the DSC system are pictured in FIG. 98. They are the computer, the chiller unit, the Pyris 6 DSC and the carrier gas. The computer allows for the storage and manipulation of the data that is obtained from the samples placed it the DSC. The chiller unit alloys for the regulation of the temperature by use of the nitrogen carrier gas. The DSC is where the sample is placed, and melts the sample. Inside the lids of the DSC there are two thermocouples where the aluminum pans are placed. The right thermocouple is for the empty reference pan and the left thermocouple is for the aluminum pan that contains the sample to be analyzed.

The DSC is calibrated by two known standards, and fitting a polynomial curve to their temperatures. Indium and Zinc were used in our calibration. The calibrations last until the instrument is moved from one location to a new location.

From the data graphs, the onset, peak, and final temperature can be obtained using the software packaged with the instrument. Other tools are available that allow the user to obtain different results, such as heat of formation of a compound.

The construction of myristolate/laurate cholestosomes by the reverse phase evaporation method (REM), as demonstrated by DSC melt, confirms one of the predictions of the molecular modeling studies. To determine if the vesicles are able to enhance delivery of a substance into living cells, the REM was used to prepare cholestosomes in the presence of fluorescein isothiocyanate (FITC). After solvent evaporation, the lipid film was resuspended in an aqueous solution of 0.5M FITC. MCF7 cells were exposed to 100 uL of the FITC-containing cholestosome (ChF) preparation or a 100 ul of a control 0.5M FITC solution overnight in complete medium. The following morning cells were washed three times with PBS, given fresh media and examined by fluorescence microscopy. MCF7 cells exposed to ChF exhibit high levels of fluorescence in comparison to cells exposed to the FITC solution (Compare the Left Column of Rows A to B). The presence of the punctuate green fluorescent spots (See Left Panel in Row A) suggests that the FITC is indeed encapsulated within the lipid vesicles. These results demonstrate the ability of cholestosomes to enhance the delivery of a substance into living cells, in vitro, after short-term exposure. To determine if a longer term exposure to cholestosomes has any affect on cell growth or viability, MCF7 cells were exposed different amounts of cholestosomes (either empty or FITC-encapsulating) for 48 h then counted and assessed for viability by trypan blue exclusion. The results demonstrated no significant differences in growth or viability in cells exposed to either empty cholestosomes or ChF. These results provide proof of principle for the ability of myristolate/laurate cholestosomes to be constructed, encapsulate a substance and deliver that substance into living cells.

Thus, it is seen that the objects of the present invention are efficiently obtained, although modifications and changes to the invention should be readily apparent to those having ordinary skill in the art, which modifications are intended to be within the spirit and scope of the invention as claimed. It also is understood that the foregoing description is illustrative of the present invention and should not be considered as limiting. Therefore, other embodiments of the present invention are possible without departing from the spirit and scope of the present invention.

What I claim is:

1. A chemical composition comprising a population of cholestosome vesicles, each vesicle comprising a hollow aqueous compartment capable of being loaded with a chemical compound and an exterior layer enclosing said hollow compartment consisting essentially of a mixture of at least two different non-ionic cholesteryl fatty acid ester molecules selected from the group consisting of cholesteryl myristate, cholesteryl laurate, cholesteryl dodeconate, cholesteryl palmitate, cholesteryl arachidonate, cholesteryl behenate, cholesteryl linoleate, cholesteryl linolenate, cholesteryl oleate and cholesteryl stearate wherein said vesicle is spherical or oval in shape.

2. The chemical composition of claim 1 wherein said vesicle is spherical in shape.

3. The chemical composition of claim 1 wherein a wall of said vesicle is selected from the group consisting of a monolayer and a bilayer.

4. The chemical composition of claim 1 wherein said mixture consists essentially of two different cholesteryl fatty acid ester molecules.

5. The chemical composition of claim 1 wherein said vesicle ranges from 1 nm to 1 micron in diameter.

6. The chemical composition of claim 1 wherein said vesicle is less than 400 nm in its shortest diameter.

7. The chemical composition of claim 1 further comprising a polyethylene glycol coat of mixed polymer size on the surface of said vesicles.

8. A method of delivering a drug to cells comprising the steps of:
   a) forming a plurality of cholestosome vesicles comprising a hollow aqueous compartment loaded with at least one drug, wherein said cholestosome vesicles comprise an exterior layer consisting essentially of a mixture of at least two non-ionic cholesteryl fatty acid ester molecules selected from a mixture of the group consisting of cholesteryl myristate, cholesteryl laurate, cholesteryl dodeconate, cholesteryl palmitate, cholesteryl arachidonate, cholesteryl behenate, cholesteryl linoleate, cholesteryl linolenate, cholesteryl oleate and cholesteryl stearate; and,
   b) utilizing said cholestosome vesicles to introduce said drug into the cells by depositing said cholestosome vesicles external to said cells.

9. The method according to claim 8 wherein said drug is introduced into said cell.

10. A method of manufacturing a plurality of cholestosome vesicles comprising the steps of:
    a) mixing a layer forming cholestosome composition consisting essentially of a mixture of at least two non-ionic cholesteryl fatty acid ester molecules selected from the group consisting of cholesteryl myristate, cholesteryl laurate, cholesteryl dodeconate, cholesteryl palmitate, cholesteryl arachidonate, cholesteryl behenate, cholesteryl linoleate, cholesteryl linolenate, cholesteryl oleate and cholesteryl stearate in a non-polar solvent to form a solution;
    b) mixing said solution of step a) with a polar solvent containing at least one drug until said at least two cholesteryl ester molecules, said at least one drug, said non-polar solvent and said polar solvent form a homogenous dispersion; and,
    c) evaporating said non-polar solvent leaving said cholestosome vesicles in said polar solvent, wherein each of said cholestosome vesicles comprises an exterior layer consisting essentially of said mixture of at least two non-ionic cholesteryl fatty acid ester molecules and a hollow compartment containing said at least one drug.

11. The method according to claim 10 wherein said non-polar solvent is an ether and said polar solvent is water.

* * * * *